US009115351B2

(12) United States Patent
Ferrari et al.

(10) Patent No.: US 9,115,351 B2
(45) Date of Patent: Aug. 25, 2015

(54) PROTEASES WITH MODIFIED PRO REGIONS

(71) Applicant: Danisco US Inc., Palo Alto, CA (US)

(72) Inventors: Eugenio Ferrari, San Bruno, CA (US); Carol Fioresi, Redwood City, CA (US); Anita van Kimmenade, San Bruno, CA (US)

(73) Assignee: DANISCO US INC., Palo Alto, CA (US)

( * ) Notice: Subject to any disclaimer, the term of this patent is extended or adjusted under 35 U.S.C. 154(b) by 0 days.

(21) Appl. No.: 13/963,184

(22) Filed: Aug. 9, 2013

(65) Prior Publication Data

US 2014/0045268 A1    Feb. 13, 2014

Related U.S. Application Data

(63) Continuation of application No. 12/761,275, filed on Apr. 15, 2010, now Pat. No. 8,530,218.

(60) Provisional application No. 61/177,899, filed on May 13, 2009, provisional application No. 61/172,587, filed on Apr. 24, 2009.

(51) Int. Cl.
| | | |
|---|---|---|
| *C12N 9/00* | (2006.01) | |
| *C12N 9/54* | (2006.01) | |
| *C12N 1/20* | (2006.01) | |
| *C12N 15/00* | (2006.01) | |
| *C07H 21/04* | (2006.01) | |
| *C12N 15/75* | (2006.01) | |

(52) U.S. Cl.
CPC . *C12N 9/54* (2013.01); *C12N 15/75* (2013.01)

(58) Field of Classification Search
None
See application file for complete search history.

(56) References Cited

U.S. PATENT DOCUMENTS

| | | | |
|---|---|---|---|
| 4,302,544 A | 11/1981 | Young et al. | |
| 4,450,235 A | 5/1984 | Dean et al. | |
| 5,217,878 A | 6/1993 | Van Eekelen et al. | |
| 5,264,366 A | 11/1993 | Ferrari et al. | |
| RE34,606 E | 5/1994 | Estell et al. | |
| 6,376,450 B1 | 4/2002 | Ghosh et al. | |
| 7,413,877 B2 | 8/2008 | Collier et al. | |
| 8,530,218 B2 * | 9/2013 | Ferrari et al. | 435/221 |
| 8,779,112 B2 * | 7/2014 | Ferrari et al. | 536/23.2 |
| 2009/0075332 A1 * | 3/2009 | Ferrari et al. | 435/69.1 |

FOREIGN PATENT DOCUMENTS

| | | |
|---|---|---|
| EP | 0134048 | 3/1985 |
| WO | WO99/34011 | 7/1999 |
| WO | WO2008/112258 | 9/2008 |
| WO | WO2008/141281 | 11/2008 |
| WO | WO2009/023271 | 2/2009 |
| WO | WO2008/112258 A2 * | 9/2014 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Altschul, et al., "Basic Local Alignment Search Tool", J. Mol. Biol., 215:403-410 (1990).
Arigoni, et al., "The SpoIIE Phosphatase, the sporulation septum and the establishment of forespore-specific transcription in *Bacillus subtilis*: a reassessment", Mol. Microbiol. 31(5):1407-1415 (1999).
Babe et al., "Heterologous expression of human granzyme K in *Bacillus subtilis* and characterization of its hydrolytic activity *in vitro*", Biotechnology and Applied Biochemistry (1998) 27, (117-124) (Printed in Great Britain).
Bittker, et al., "Nucleic acid evolution and minimization by nonhomologous random recombination", Nature Biotechnology 20(10):1024-1029 (2002).
Bittker, et al., "Directed Evolution of Protein Enzymes Using Nonhomologous Random Recombination", Proc. Natl. Acad. Sci. U S A., 101(18):7011-7016 (2004).
Caldwell, et al., "Correlation between *Bacillus subtilis scoC* Phenotype and Gene Expression Determined Using Microarrays for Transcriptome Analysis", Journal of Bacteriology, 183(24):7329-7340 (2001).
Chang, et al., "High Frequency Transformation of *Bacillus subtilis* Protoplasts by Plasmid DNA", Mol. Gen. Genet., 168:111-115 (1979).
Chica et al. Curr Opin Biotechnol 16(4):378-384, Aug. 2005.
Christianson, et al., "Peptide Mapping of Subtilisins as a Practical Tool for Locating Protein Sequence Errors during Extensive Protein Engineering Projects", Anal. Biochem., 223:119 -129 (1994).
Coco, et al., "Growth Factor Engineering by Degenerate Homoduplex Gene Family Recombination", Nat. Biotechnol. 20(12):1246-1250 (2002).
Contente et al., "Marker Rescue Transformation by Linear Plasmid DNA in *Bacillus subtilis*", Plasmid 2:555-571 (1979).
Del Mar, et al., "A Sensitive New Substrate for Chymotrypsin", Anal. Biochem., 99:316-320 (1979).
Estell, et al., "Engineering an Enzyme by Site-directed Mutagenesis to Be Resistant to Chemical Oxidation" Journal of Biological Chemistry, 260(11):6518-6521 (1985).

(Continued)

*Primary Examiner* — Christian Fronda
(74) *Attorney, Agent, or Firm* — Danisco US Inc.

(57) ABSTRACT

The present invention provides methods and compositions for the production of mature proteases in bacterial host cells. The compositions include modified polynucleotides that encode modified proteases, which have at least one mutation in the pro region; the modified serine proteases encoded by the modified polynucleotides; expression cassettes, DNA constructs, and vectors comprising the modified polynucleotides that encode the modified proteases; and the bacterial host cells transformed with the vectors of the invention. The methods include methods for enhancing the production of mature proteases in bacterial host cells e.g. *Bacillus* sp. host cells. The produced proteases find use in the industrial production of enzymes, suitable for use in various industries, including but not limited to the cleaning, animal feed and textile processing industry.

19 Claims, 8 Drawing Sheets

(56) References Cited

OTHER PUBLICATIONS

Fahnestock, et al., "Expression of the Staphylococcal Protein A Gene in *Bacillus subtilis* by Gene Fusions Utilizing the Promoter from a *Bacillus amyloliquefaciens* α-Amylase Gene", J. Bacteriol., 165(3):796-804 (1986).
Ferrari, et al., "Construction and Properties of an Integrable Plasmid for *Bacillus subtilis*", J. Bacteriol. 154(3):1513-1515 (1983).
Ferrari, et al., "Genetics," in Hardwood et al, (eds.), *Bacillus*, Plenum Publishing Corp., pp. 57-72 (1989).
Fisher et al., "Introduction of plasmid pC194 into *Bacillus thuringiensis* by protoplast transformation and plasmid transfer", Arch. Microbiol., 139:213-217 (1981).
Gaytán, et al., "Orthogonal combinatorial mutagenesis: a condon-level combinatorial mutagenesis method useful for low multiplicity and amino acid-scanning protocols", Nucleic Acids Res., 29(3):e9 (2001).
Gaytán, et al., "Novel ceftazidime-resistance β-lactamases generated by a condon-based mutagenesis method and selection", Nucleic Acids Res., 30(16):e84 (2002).
Glaser, et al., "Antibody engineering by codon-based mutagenesis in a filamentous phage vector system", J. Immunol. 149: 3903-3913 (1992).
Haima et al., "Novel plasmid marker rescue transformation system for molecular cloning in *Bacillus subtilis* enabling direct selection of recombinants", Mol. Gen. Genet., 223:185-191 (1990).
Henikoff, et al., "Amino acid substitution matrices from protein blocks", *Proc. Natl. Acad. Sci. USA*, 89:10915-10919 (1992).
Hoch, et al., "Chromosomal Location of Pleiotropic Negative Sporulation Mutations in *Bacillus Subtilis*", Genetics, 73:215-228 (1973).
Hoch, et al., "Transformation and Transduction in Recombination-defective Mutants of *Bacillus subtilis*", J. Bacteriol., 93(6):1925-1937 (1967).
Holubova, et al., "Transfer of Liposome-Encapsulated Plasmid DNA to *Bacillus subtilis* Protoplasts and Calcium-Treated *Escherichia coli* Cells", Folia Microbiol., 30:97-100 (1985).
Hsia et al., "Active-Site Titration of Serine Proteases Using a Fluoride Ion Selective Electrode and Sulfonyl Fluoride Inhibitors", Anal Biochem., 242:221-227 (1996).
Kalisz, "Microbial Proteinases," In: Fiechter (ed.), Advances in Biochemical Engineering/Biotechnology, (1988).
Karlin, et al., "Applications and statistics for multiple high-scoring segments in molecular sequences", Proc. Nat'l. Acad. Sci. USA, 90:5873-5787 (1993).
Kroll, et al., "A Multifunctional Prokaryotic Protein Expression System: Overproduction, Affinity Purification, and Selective Detection", DNA Cell Biol., 12(5):441-453 (1993).
Lutz et al., "Creating multiple-crossover DNA libraries independent of sequence identity", Prod. Nat. Acad. Sci. USA, (20):11248-11253 (2001).
Maddox et al., "Elevated Serum Levels in Human Pregnancy of a Molecule Immunochemically Similar to Eosinophil Granule Major Basic Protein", J. Exp. Med., 158:1211-1226 (1983).
Mann et al., "Transformation of *Bacillus spp.*: an Examination of the Transformation of *Bacillus* Protoplasts by Plasmids pUB110 and pHV33", Current Microbiology, 13:191-195 (1986).
McDonald, et al., "Plasmid Transformation of *Bacillus sphaericus* 1593", J. Gen. Microbiol., 130:203-208 (1984).
Msadek, et al., "Signal Transduction Pathway Controlling Synthesis of a Class of Degradative Enzymes in *Bacillus subtilis*: Expression of the Regulatory Genes and Analysis of Mutations in *degS* and *degU*", J. Bacteriol., 172:824-834 (1990).
Nagarjan V., "Protein Secretion in *Bacillus subtilis* and other Gram-Positive Bacteria" Ch. 49, p. 713-726 (1993).
Ness, et al., "Synthetic shuffling expands functional protein diversity by allowing amino acids to recombine independently", Nature Biotechnology, 20(12):1251-1255 (2002).
Olmos, et al., "Effects of the sinR and degU32 (Hy) mutations on the regulation of the aprE gene in *Bacillus subtilis*", Mol. Gen. Genet., 253:562-567 (1997).
Ostermeier, et al., "Incremental Truncation as a Strategy in the Engineering of Novel Biocatalysts", Bioorganic & Medicinal Chemistry, (7)2139-2144 (1999).
Osuna, et al., "Protein evolution by codon-based random deletions", Nucleic Acids Res. 32(17):e136 (2004).
Palmeros, et al., "A family of removable cassettes designed to obtain antibiotic-resistance-free genomic modifications of *Escherichia coli* and other bacteria", Gene 247:255-264 (2000).
Palva, et al., "Molecular cloning of α-amylase gene from *Bacillus amyloliquefaciens* and its expression", Gene 19:81-87 (1982).
Perego, et al., "The oligopeptide transport system of *Bacillus subtiis* plays a role in the initiation of sporulation", Mol. Microbiol., 5(1):173-185 (1991).
Perego, M. (1993) Integrational Vectors for Genetic Manipulations in *Bacillus subtilis*, p. 615-624.
Porath, J., "Immobilized Metal Ion Affinity Chromatography", Protein Expression and Purification 3:263-281 (1992).
Power, et al., "Secretion and autoproteolytic maturation of subtilisin", Proc. Natl. Acad. Sci. USA 83:3096-3100 (1986).
Rawlings, et al., MEROPS: the peptidase database, Nucleic Acids Res, 34 Database issue:D270-272, (2006).
Rawlings, et al., "Evolutionary families of peptidases" Biochem. J., 290:205-218 (1993).
Ruan, et al., "Rapid Folding of Calcium-Free Substilisin by a Stabilized Pro-Domain Mutant", Biochemistry, 38(26):8562-8571 (1999).
Saunders et al., "Use of Chromosomal Integration in the Establishment and Expression of, a *Staphylococcus aureus* β-Lactamase, Gene, in *Bacillus subtilis*", J. Bacteriol., 157(3):718-726 (1984).
Sen et al. Appl Biocehm Biotechnol 143(3):212-223, Dec. 2007.
Sieber, et al., "Libraries of Hybrid Proteins from distantly related sequences", Nature Biotechnology 19(5):456-60 (2001).
Smith, et al., "Protoplast Transformation in Coryneform Bacteria and Introduction of an α-Amylase Gene from *Bacillus amyloliquefaciens* into *Brevibacterium lactofermentum*", Applied and Environmental Microbiology, 51(3):634-639 (1986).
Sondek, et al., "A General Strategy for Random Insertion and Substitution Mutagenesis: Substoichiometric Coupling of Trinucleotide Phosphoramidites", Proc. Natl. Acad. Sci. U S A 89(8):3581-3585 (1992).
Stahl, et al., "Replacement of the *Bacillus subtilis* Subtilisin Structural Gene with an In Vitro-Derived Deletion Mutation", J. Bacteriol., 158(2):411-418 (1984).
Stemmer W.P., "DNA shuffling by random fragmentation and reassembly: In vitro recombination for molecular evolution", Proc. Natl. Acad. Sci. U S A. 91:10747-10751 (1994).
Vorobjeya, et al., "Transformation of *Bacillus Megaterium* Protoplasts by Plasmid DNA", FEMS Microbiol. Lett., 7:261-263 (1980).
Wang, et al., "Engineering the Independent Folding of the Subtilisin BPN' Pro-Domain: Correlation of Pro-Domain Stability with the Rate of Subtilisin Folding", Biochemistry 37:3165-3171 (1998);.
Ward, O.P., "Proteinases," in Fogarty (ed.)., Microbial Enzymes and Biotechnology, Applied Science, London, pp. 251-317 (1983).
Weinrauch, et al., "Plasmid Marker Rescue Transformation in *Bacillus subtilis*", J. Bacteriol., 154(3):1077-1087 (1983).
Weinrauch, et al., "Plasmid Marker Rescue Transformation Proceeds by Breakage-Reunion in *Bacillus subtilis*", J. Bacteriol., 169(3):1205-1211 (1987).
Wells, et al., "Cloning, sequencing, and secretion of *Bacillus amyloliquefaciens* subtilisin in *Bacillus subtilis*", Nucleic Acids Res. 11(22):7911-7925 (1983).
Yáñez, et al., "Combinatorial codon-based amino acid substitutions", Nucleic Acids Res., 32(20):e158 (2004).
Zha, et al., "Assembly of Designed Oligonucleotides as an Efficient Method for Gene Recombination: A New Tool in Directed Evolution", Chembiochem. 4:34-39 (2003).
International Search Report and the Written Opinion from the International Searching Authority for International Application No. PCT/US2010/031269 mailed Jul. 2, 2010.

\* cited by examiner

```
           1                                                  50
    (1)    AQSVPWGISRVQAPAAHNRGLTGSGVKVAVLDTGISTHPDLNIRGGASFV
    (1)    AQSVPWGISRVQAPAAHNRGLTGSGVKVAVLDTGISTHPDLNIRGGASFV
    (1)    AQSVPWGISRVQAPAAHNRGLTGSGVKVAVLDTGISTHPDLNIRGGASFV
    (1)    AQSVPWGISRVQAPAAHNRGLTGSGVKVAVLDTGISTHPDLNIRGGASFV
    (1)    AQSVPWGISRVQAPAAHNRGLTGSGVKVAVLDTGISTHPDLNIRGGASFV
    (1)    AQSVPWGISRVQAPAAHNRGLTGSGVKVAVLDTGISTHPDLNIRGGASFV
    (1)    AQSVPWGISRVQAPAAHNRGLTGSGVKVAVLDTGISTHPDLNIRGGASFV
    (1)    AQSVPWGISRVQAPAAHNRGLTGSGVKVAVLDTGISTHPDLNIRGGASFV
    (1)    AQSVPWGISRVQAPAAHNRGLTGSGVKVAVLDTGISTHPDLNIRGGASFV 51                                                 100
   (51)    PGEPSTQDGNGHGTHVAGTIAALNNSIGVLGVAPSAELYAVKVLGASGSG
   (51)    PGEPSTQDGNGHGTHVAGTIAALDNSIGVLGVAPSAELYAVKVLGASGSG
   (51)    PGEPSTQDGNGHGTHVAGTIAALNNSIGVLGVAPNAELYAVKVLGASGSG
   (51)    PGEPSTQDGNGHGTHVAGTIAALNNSIGVLGVAPNAELYAVKVLGASGSG
   (51)    PGEPSTQDGNGHGTHVAGTIAALNNSIGVLGVAPNAELYAVKVLGASGMG
   (51)    PGEPSTQDGNGHGTHVAGTIAALNNSIGVLGVAPNAELYAVKVLGASGGG
   (51)    PGEPSTQDGNGHGTHVAGTIAALDNSIGVLGVAPRAELYAVKVLGASGSG
   (51)    PGEPSTQDGNGHGTHVAGTIAALDNSIGVLGVAPRAELYAVKVLGASGSG
   (51)    PGEPSTQDGNGHGTHVAGTIAALDNSIGVLGVAPRAELYAVKVLGASGSG
                                 *           *         *

101                                                150
  (101)    SVSSIAQGLEWAGNNGMHVANLSLGSPSPSATLEQAVNSATSRGVLVVAA
  (101)    AISSIAQGLEWAGNNGMHVANLSLGSPSPSATLEQAVNSATSRGVLVVAA
  (101)    SVSSIAQGLEWAGNNGMHVANLSLGSPSPSATLEQAVNSATSRGVLVVAA
  (101)    SVSSIAQGLEWAGNNVMHVANLSLGLQAPSATLEQAVNSATSRGVLVVAA
  (101)    SVSSIAQGLEWAGNNVMHVANLSLGLQAPSATLEQAVNSATSRGVLVVAA
  (101)    SNSSIAQGLEWAGNNGMHVANLSLGSPSPSATLEQAVNSATSRGVLVVAA
  (101)    SVSSIAQGLEWAGNNRMHVANLSLGLQAPSATLEQAVNSATSRGVLVVAA
  (101)    SVSSIAQGLEWAGNNRMHVANLSLGLQAPSATLEQAVNSATSRGVLVVAA
  (101)    SVSSIAQGLEWAGNNGMHVANLSLGLQAPSATLEQAVNSATSRGVLVVAA
           **           *       ***

151                                                200
  (151)    SGNSGAGSISYPARYANAMAVGATDQNNNRASFSQYGAGLDIVAPGVNVQ
  (151)    SGNSGAGSISYPARYANAMAVGATDQNNNRASFSQYGAGLDIVAPGVNVQ
  (151)    SGNSGAGSISYPARYANAMAVGATDQNNNRASFSQYGAGLDIVAPGVNVQ
  (151)    SGNSGAGSISYPARYANAMAVGATDQNNNRASFSQYGAGLDIVAPGVNVQ
  (151)    SGNSGAGSISYPARYANAMAVGATDQNNNRASFSQYGAGLDIVAPGVNVQ
  (151)    SGNSGAGSISYPARYANAMAVGATDQNNNRASFSQYGAGLDIVAPGVNVQ
  (151)    SGNSGAGSISYPARYANAMAVGATDQNNNRASFSQYGAGLDIVAPGVNVQ
  (151)    SGNSGAGSISYPARYANAMAVGATDQNNNRADFSQYGAGLDIVAPGVNVQ
  (151)    SGNSGAGSISYPARYANAMAVGATDQNNNRADFSQYGAGLDIVAPGVNVQ
                                         *

201                                                250
  (201)    STYPGSTYASLNGTSMATPHVAGAAALVKQKNPSWSNVQIRNHLKNTATS
  (201)    STYPGSTYASLNGTSMATPHVAGAAALVKQKNPSWSNVQIRNHLKNTATS
  (201)    STYPGSTYASLNGTSMATPHVAGAAALVKQKNPSWSNVQIRNHLKNTATS
  (201)    STYPGSTYASLNGTSMATPHVAGAAALVKQKNPSWSNVQIRNHLKNTATS
  (201)    STYPGSTYASLNGTSMATPHVAGAAALVKQKNPSWSNVQIRNHLKNTATS
  (201)    STYPGSTYASLNGTSMATPHVAGAAALVKQKNPSWSNVQIRNHLKNTATS
  (201)    STYPGSTYASLNGTSMATPHVAGAAALVKQKNPSWSNVQIRNHLKNTATS
  (201)    STYPGSTYASLNGTSMATPHVAGAAALVKQKNPSWSNRQIRNHLKNTATS
  (201)    STYPGSTYASLNGTSMATPHVAGAAALVKQKNPSWSNVQIRRHLKNTATS
                                                *  *

251         269                        % Identity
  (251)    LGSTNLYGSGLVNAEAATR (SEQ ID NO:9)       100
  (251)    LGSTNLYGSGLVNAEAATR (SEQ ID NO:11)       98.9
  (251)    LGSTNLYGSGLVNAEAATR (SEQ ID NO:13)       99.7
  (251)    LGSTNLYGSGLVNAEAATR (SEQ ID NO:15)       98.2
  (251)    LGSTNLYGSGLVNAEAATR (SEQ ID NO:17)       97.8
  (251)    LGSTNLYGSGLVNAEAATR (SEQ ID NO:19)       98.9
  (251)    LGSTNLYGSGLVNAEAATR (SEQ ID NO:21)       97.8
  (251)    LGSTNLYGSGLVNAEAATR (SEQ ID NO:23)       97.1
  (251)    LGSTNLYGSGLVNAEAATR (SEQ ID NO:25)       97.1
```

FIGURE 1

```
GG36_B_lentus_267048              AQSVPWGISRVQAPAAHNRGLTGSGVKVAVLDTGI-STHPDLNIRGGASF
P41362_Bacillus_clausii           AQSVPWGISRVQAPAAHNRGLTGSGVKVAVLDTGI-STHPDLNIRGGASF
P27693_Bacillus_alcalophilus      AQSVPWGISRVQAPAAHNRGLTGSGVKVAVLDTGI-STHPDLNIRGGASF
P20724_Bacillus_sp_YAB            -QTVPWGINRVQAPIAQSRGFTGTGVRVAVLDTGI-STHPDLNIRGGASF
BAA25184_Bacillus_sp              -QTVPWGINRVQAPIAQSRGFTGTGVRVAVLDTGI-SNHADLRIRGGASF
YP_174261_B_clausii_KSM-K16       AQSVPWGISRVQAPAAHNRGLTGSGVKVAVLDTGI-STHPDLNIRGGASF
BAA06157_Bacillus_sp_G-825-6      NQVTPWGITRVQAPTAWTRGYTGTGVRVAVLDTGI-STHPDLNIRGGVSF
BAF34115_A_transvaalensis         AQSTPWGVTRVQAPNVWNRGFTGSGVRVAVLDTGIHSSSHEDLTVSGGYS-
                                    ***;.******  . ** **;:***********   *    ; **

GG36_B_lentus_267048              VPGEPSTQDGNGHGTHVAGTIAALNNSIGVLGVAPSAELYAVKVLGASGS
P41362_Bacillus_clausii           VPGEPSTQDGNGHGTHVAGTIAALNNSIGVLGVAPSAELYAVKVLGASGS
P27693_Bacillus_alcalophilus      VPGEPSTQDGNGHGTHVAGTIAALNNSIGVLGVAPSAELYAVKVLGASGS
P20724_Bacillus_sp_YAB            VPGEPNISDGNGHGTQVAGTIAALNNSIGVLGVAPNAELYAVKVLGASGS
BAA25184_Bacillus_sp              VPGEPNISDGNGHGTQVAGTIAALNNSIGVLGVAPNVDLYGVKVLGASGS
YP_174261_B_clausii_KSM-K16       VPGEPSTQDGNGHGTHVAGTIAALNNSIGVLGVAPNVDLYGVKVLGASGS
BAA06157_Bacillus_sp_G-825-6      VPGEPSYQDGNGHGTHVAGTIAALNNSIGVVGVAPNAELYAVKVLGASGS
BAF34115_A_transvaalensis         VFGDSPYNDVQGHGTHVAGTIAARNNSVGVIGVAYNAQLYAVKVLNNQGS
                                  * *: .   *  * :******;******** ***.:**      .  .**

GG36_B_lentus_267048              GSVSSIAQGLEWAGNNGMHVANLSLGSPSPSATLEQAVNSATSRGVLVVA
P41362_Bacillus_clausii           GSVSSIAQGLEWAGNNGMHVANLSLGSPSPSATLEQAVNSATSRGVLVVA
P27693_Bacillus_alcalophilus      GSVSSIAQGLEWAGNNGMHVANLSLGSPSPSATLEQAVNSATSRGVLVVA
P20724_Bacillus_sp_YAB            GSISGIAQGLQWAANNGMEHIANMSLGSSAGSATMEQAVNQATASGVLVVA
BAA25184_Bacillus_sp              GSISGIAQGLQWAANNGMHIANMSLGSSAGSATMEQAVNQATASGVLVVA
YP_174261_B_clausii_KSM-K16       GSVSSIAQGLEWAGNNGMHVANLSLGSPSPSATLEQAVNSATSRGVLVVA
BAA06157_Bacillus_sp_G-825-6      GSVSSIAQGLQWTAQNNIHVANLSLGSPVGSQTLELAVNQATNAGVLVVA
BAF34115_A_transvaalensis         GTLAGIAQGIEWARQNNMHVINMSLGGTSGSTTLQNAVNAAYNAGILVVA
                                  *:::.****::**: :*:.:**: *:***..           *** *  ** .****
```

FIGURE 3A

```
GG36_B_lentus_267048         ASGNSG--AGS---ISYPARYANAMAVGATDQNNNRASFSQYGAGLDIVA
P41362_Bacillus_clausii      ASGNSG--AGS---ISYPARYANAMAVGATDQNNNRASFSQYGAGLDIVA
P27693_Bacillus_alcalophilus ASGNSG--AGS---ISYPARYANAMAVGATDQNNNRASFSQYGAGLDIVA
P20724_Bacillus_sp_YAB       ASGNSG--AGN---VGFPARYANAMAVGATDQNNNRATFSQYGAGLDIVA
BAA25184_Bacillus_sp         ASGNSG--AGN---VGFPARYANAMAVGATDQNNNRASFSQYGAGLDIVA
YP_174261_B_clausii_KSM-K16  ASGNSG--AGS---ISYPARYANAMAVGATDQNNNRASFSQYGAGLDIVA
BAA06157_Bacillus_sp_G-825-6 ATGNNG--SGT---VSYPARYANALAVGATDQNNNRASFSQYGTGLNIVA
BAF34115_A_transvaalensis    AAGNSGNSAGTGDNVGFPARYPNAMAVAATTSGNVRASFSSTGPAVEIAA
                             *:***. :*.    . .:****.**:****.**  . **:***. *.*

GG36_B_lentus_267048         PGVNVQSTYPGSTYASLNGTSMATPHVAGAAAALVKQKNPSWSNVQIRNHL  (SEQ ID NO:9)
P41362_Bacillus_clausii      PGVNVQSTYPGSTYASLNGTSMATPHVAGAAAALVKQKNPSWSNVQIRNHL  (SEQ ID NO:9)
P27693_Bacillus_alcalophilus PGVNVQSTYPGSTYASLNGTSMATPHVAGAAAALVKQKNPSWSNVQIRNHL  (SEQ ID NO:47)
P20724_Bacillus_sp_YAB       PGVGVQSTVPGNYASFNGTSMATPHVAGVAALVKQKNPSWSNVQIRNHL   (SEQ ID NO:48)
BAA25184_Bacillus_sp         PGVGVQSTVPGNYSSFNGTSMATPHVAGVAALVKQKNPSWSNVQIRNHL   (SEQ ID NO:49)
YP_174261_B_clausii_KSM-K16  PGVNVQSTYPGSTYASLNGTSMATPHVAGVAALVKQKNPSWSNVQIRNHL  (SEQ ID NO:50)
BAA06157_Bacillus_sp_G-825-6 PGVGIQSTYPGNRYASLSGTSMATPHVAGVAALVKQKNPSWSNTQIRQHL  (SEQ ID NO:51)
BAF34115_A_transvaalensis    PGQDINSTYPTNTYRSLNGTSMAAPHVAGVAALLKSARPAVTAAGIRNAM  (SEQ ID NO:52)
                             ** .::***.*    *: *****.*****: .*** . . **: .

%IDENTITY
GG36_B_lentus_267048         KNTATSLGSTNLYGSGLVNAEAATR                              100
P41362_Bacillus_clausii      KNTATSLGSTNLYGSGLVNAEAATR                              100
P27693_Bacillus_alcalophilus KNTATSLGSTNLYGSGLVNAEAATR                              99.7
P20724_Bacillus_sp_YAB       KNTATNLGNTTQFGSGLVNAEAATR                              82.1
BAA25184_Bacillus_sp         KNTATNLGNTNQFGSGLVNAEAATR                              82.9
YP_174261_B_clausii_KSM-K16  KNTATGLGNTNLYGSGLVNAEAATR                              98.9
BAA06157_Bacillus_sp_G-825-6 TSTATSLGNSNQFGSGLVNAEAATR                              81.5
BAF34115_A_transvaalensis    NSTALNLGNSNWYGNGLVRANNALD                              61.2
                             .:** .**.:: .:*.***.:: *
```

```
      501                                                                                          600
(501) CGCAATGGCAGTCGGAGCTCGGAGCTTACTGACCAAAACAACAACAACCGCGCCAGCTTTTCACAGTATGGCGCAGGGCTTGACATTGTCGCACCAGGTGTAAACGTGCAG
(501) CGCAATGGCAGTCGGAGCTCGGAGCTTACTGACCAAAACAACAACAACCGCGCCAGCTTTTCACAGTATGGCGCAGGGCTTGACATTGTCGCACCAGGTGTAAACGTGCAG
(501) CGCAATGGCAGTCGGAGCTCGGAGCTTACTGACCAAAACAACAACAACCGCGCCAGCTTTTCACAGTATGGCGCAGGGCTTGACATTGTCGCACCAGGTGTAAACGTGCAG
(501) CGCAATGGCAGTCGGAGCTCGGAGCTTACTGACCAAAACAACAACAACCGCGCCAGCTTTTCACAGTATGGCGCAGGGCTTGACATTGTCGCACCAGGTGTAAACGTGCAG
(501) CGCAATGGCAGTCGGAGCTCGGAGCTTACTGACCAAAACAACAACAACCGCGCCAGCTTTTCACAGTATGGCGCAGGGCTTGACATTGTCGCACCAGGTGTAAACGTGCAG
(501) CGCAATGGCAGTCGGAGCTCGGAGCTTACTGACCAAAACAACAACAACCGCGCCAGCTTTTCACAGTATGGCGCAGGGCTTGACATTGTCGCACCAGGTGTAAACGTGCAG
(501) CGCAATGGCAGTCGGAGCTCGGAGCTTACTGACCAAAACAACAACAACCGCGCCAGCTTTTCACAGTATGGCGCAGGGCTTGACATTGTCGCACCAGGTGTAAACGTGCAG
(501) CGCAATGGCAGTCGGAGCTCGGAGCTTACTGACCAAAACAACAACAACCGCGCCAGCTTTTCACAGTATGGCGCAGGGCTTGACATTGTCGCACCAGGTGTAAACGTGCAG
(501) CGCAATGGCAGTCGGAGCTCGGAGCTTACTGACTGACCAAAACAACAACCGCGCCGATTTTTCACGATTGCCAGGGCTTGACATTGTCGCACCAGGTGTAAACGTGCAG
(501) CGCAATGGCAGTCGGAGCTCGGAGCTTACTGACCAAAACAACAACCAACCGCGCCGATTTTCCACCAGTATGCCCAGGGCTTGACATTGTCGCACCAGGTGTAAACGTGCAG 601                                                                                          700
(601) AGCACATACCCAGGTTCAACGTATGCCAGCTTAAACGTTAAACGTTAAGCTTGCAGGTGCAGCTGAAGTGCAGCAGCAGCCCTTGTTAAACAAAAGAACCCAT
(601) AGCACATACCCAGGTTCAACGTATGCCAGCTTAAACGTTAAACGTTAAGCTTGCAGGTGCAGCTGAAGTGCAGCAGCAGCCCTTGTTAAACAAAAGAACCCAT
(601) AGCACATACCCAGGTTCAACGTATGCCAGCTTAAACGTTAAACGTTAAGCTTGCAGGTGCAGCTGAAGTGCAGCAGCAGCCCTTGTTAAACAAAAGAACCCAT
(601) AGCACATACCCAGGTTCAACGTATGCCAGCTTAAACGTTAAACGTTAAGCTTGCAGGTGCAGCTGAAGTGCAGCAGCAGCCCTTGTTAAACAAAAGAACCCAT
(601) AGCACATACCCAGGTTCAACGTATGCCAGCTTAAACGTTAAACGTTAAGCTTGCAGGTGCAGCTGAAGTGCAGCAGCAGCCCTTGTTAAACAAAAGAACCCAT
(601) AGCACATACCCAGGTTCAACGTATGCCAGCTTAAACGTTAAACGTTAAGCTTGCAGGTGCAGCTGAAGTGCAGCAGCAGCCCTTGTTAAACAAAAGAACCCAT
(601) AGCACATACCCAGGTTCAACGTATGCCAGCTTAAACGTTAAACGTTAAGCTTGCAGGTGCAGCTGAAGTGCAGCAGCAGCCCTTGTTAAACAAAAGAACCCAT
(601) AGCACATACCCAGGTTCAACGTATGCCAGCTTAAACGTTAAACGTTAAGCTTGCAGGTGCAGCTGAAGTGCAGCAGCAGCCCTTGTTAAACAAAAGAACCCAT
(601) AGCACATACCCAGGTTCAACGTATGCCAGCTTAAACGTTAAACGTTAAGCTTGCAGGTGCAGCTGAAGTGCAGCAGCAGCCCTTGTTAAACAAAAGAACCCAT
(601) AGCACATACCCAGGTTCAACGTATGCCAGCTTAAACGTTAAACGTTAAGCTTGCAGGTGCAGCTGAAGTGCAGCAGCAGCCCTTGTTAAACAAAAGAACCCAT 701                                                                                          800
(701) CTTGGTCCAATGTACAAATCGCAATCATCTAAAGAATACGGCAACGAGCTTAGGAACGCACGAACTTGTATGGAAGCACGAACTTGTCAATGCAGAAGCTGC
(701) CTTGGTCCAATGTACAAATCGCAATCATCTAAAGAATACGGCAACGAGCTTAGGAACGCACGAACTTGTATGGAAGCACGAACTTGTCAATGCAGAAGCTGC
(701) CTTGGTCCAATGTACAAATCGCAATCATCTAAAGAATACGGCAACGAGCTTAGGAACGCACGAACTTGTATGGAAGCACGAACTTGTCAATGCAGAAGCGGC
(701) CTTGGTCCAATGTACAAATCGCAATCATCTAAAGAATACGGCAACGAGCTTAGGAACGCACGAACTTGTATGGAAGCACGAACTTGTCAATGCAGAAGCGGC
(701) CTTGGTCCAATGTACAAATCGCAATCATCTAAAGAATACGGCAACGAGCTTAGGAACGCACGAACTTGTATGGAAGCACGAACTTGTCAATGCAGAAGCGGC
(701) CTTGGTCCAATGTACAAATCGCAATCATCTAAAGAATACGGCAACGAGCTTAGGAACGCACGAACTTGTATGGAAGCACGAACTTGTCAATGCAGAAGCGGC
(701) CTTGGTCCAATGTACAAATCGCAATCATCTAAAGAATACGGCAACGAGCTTAGGAACGCACGAACTTGTATGGAAGCACGAACTTGTCAATGCAGAAGCTGC
(701) CTTGGTCCAATGTCGCAAATCGCAATCATCTAAAGAATACGGCAACGAGCTTAGGAACGCACGAACTTGTATGGAAGCACGAACTTGTCAATGCAGAAGCTGC
(701) CTTGGTCCAATGTACAAATCGTCAAATCGCAATCATCTAAAGAATACGGCAACGAGCTTAGGAACGCACGAACTTGTATGGAAGCACGAACTTGTCAATGCAGAAGCTGC
(701) CTTGGTCCAATGTACAAATCGTACAAATCCGCAGACATCTAAAAGAATACGGCAACGAGCTTAGGAACGCACGAACTTGTATGGAAGCACGAACTTGTCAATGCAGAAGCTGC 801
(801) AACTCGT (SEQ ID NO:8)
(801) AACTCGT (SEQ ID NO:10)
(801) AACACGC (SEQ ID NO:12)
(801) AACACGT (SEQ ID NO:14)
(801) AACACGT (SEQ ID NO:16)
(801) AACACGT (SEQ ID NO:18)
(801) AACTCGT (SEQ ID NO:20)
(801) AACTCGT (SEQ ID NO:22)
(801) AACTCGT (SEQ ID NO:24)
```

FIGURE 5B

PROTEASES WITH MODIFIED PRO REGIONS

FIELD OF THE INVENTION

The present invention provides methods and compositions for the production of mature proteases in bacterial host cells. The compositions include modified polynucleotides that encode modified proteases, which have at least one mutation in the pro region; the modified serine proteases encoded by the modified polynucleotides; expression cassettes, DNA constructs, and vectors comprising the modified polynucleotides that encode the modified proteases; and the bacterial host cells transformed with the vectors of the invention. The methods include methods for enhancing the production of mature proteases in bacterial host cells e.g. *Bacillus* sp. host cells. The produced proteases find use in the industrial production of enzymes, suitable for use in various industries, including but not limited to the cleaning, animal feed and textile processing industry.

BACKGROUND

Microorganisms, such as the Gram-positive microorganism that are members of the genus *Bacillus*, have been used for large-scale industrial fermentation due, in part, to their ability to secrete their fermentation products into their culture media. Secreted proteins are exported across a cell membrane and a cell wall, and then are subsequently released into the external media.

Indeed, secretion of heterologous polypeptides is a widely used technique in industry. Typically, cells are transformed with a nucleic acid encoding a heterologous polypeptide of interest to be expressed and secreted to produce large quantities of desired polypeptides. Expression and secretion of desired polypeptides has been controlled through genetic manipulation of the polynucleotides that encode the desired proteins. Despite various advances in protein production methods, there remains a need in the art to provide more efficient methods for extracellular protein secretion with the aim to enhance the production of enzymes such as proteases, which find use in the use in various industries, including but not limited to the cleaning, animal feed and textile processing industry.

SUMMARY OF THE INVENTION

The present invention provides methods and compositions for the production of mature proteases in bacterial host cells. The compositions include modified polynucleotides that encode modified proteases, which have at least one mutation in the pro region; the modified serine proteases encoded by the modified polynucleotides; expression cassettes, DNA constructs, and vectors comprising the modified polynucleotides that encode the modified proteases; and the bacterial host cells transformed with the vectors of the invention. The methods include methods for enhancing the production of mature proteases in bacterial host cells e.g. *Bacillus* sp. host cells. The produced proteases find use in the industrial production of enzymes, suitable for use in various industries, including but not limited to the cleaning, animal feed and textile processing industry.

In one embodiment, the invention provides an isolated modified polynucleotide that encodes a modified protease. The isolated modified polynucleotide comprises a first polynucleotide that encodes a signal peptide, which is operably linked to a second polynucleotide that encodes the pro region set forth in SEQ ID NO:7, which comprises a combination of substitutions of at least two amino acids at positions chosen from positions 6, 30 and 32 of the pro region. In turn, the second polynucleotide is operably linked to a third polynucleotide that encodes the mature region of a protease that is at least about 60% identical to the mature protease of SEQ ID NO: 9. Preferably, the substitutions enhance the production of the mature protease by a *Bacillus* sp. host e.g. *Bacillus subtilis*.

In another embodiment, the isolated modified polynucleotide comprises a first polynucleotide that encodes a signal peptide, which is operably linked to a second polynucleotide that encodes the pro region set forth in SEQ ID NO:7, which comprises a combination of substitutions of at least two amino acids at positions chosen from positions 6, 30 and 32 of the pro region. In turn, the second polynucleotide is operably linked to a third polynucleotide that encodes the mature region of a wild-type or variant alkaline serine protease derived from *Bacillus clausii* or *Bacillus lentus* that is at least about 60% identical to the mature protease of SEQ ID NO: 9. Preferably, the substitutions enhance the production of the mature protease by a *Bacillus* sp. host e.g. *Bacillus subtilis*.

In another embodiment, the isolated modified polynucleotide comprises a first polynucleotide that encodes a signal peptide, which is operably linked to a second polynucleotide that encodes the pro region set forth in SEQ ID NO:7, which comprises a combination of substitutions of at least two amino acids at positions chosen from positions 6, 30 and 32 of the pro region. In turn, the second polynucleotide is operably linked to a third polynucleotide that encodes the mature region of a protease chosen from SEQ ID NOS:9, 11, 13, 15, 17, 19, and 21. Preferably, the substitutions enhance the production of the mature protease by a *Bacillus* sp. host e.g. *Bacillus subtilis*.

In another embodiment, the invention provides an isolated modified polynucleotide that encodes a modified protease. The isolated modified polynucleotide comprises a first polynucleotide that encodes a signal peptide chosen from SEQ ID NOS:3 and 5, which is operably linked to a second polynucleotide that encodes the pro region set forth in SEQ ID NO:7, which comprises a combination of substitutions of at least two amino acids at positions chosen from positions 6, 30 and 32 of the pro region. In turn, the second polynucleotide is operably linked to a third polynucleotide that encodes the mature region of a protease that is at least about 60% identical to the mature protease of SEQ ID NO: 9. Preferably, the substitutions enhance the production of the mature protease by a *Bacillus* sp. host e.g. *Bacillus subtilis*.

In another embodiment, the isolated modified polynucleotide comprises a first polynucleotide that encodes a signal peptide chosen from SEQ ID NOS:3 and 5, which is operably linked to a second polynucleotide that encodes the pro region set forth in SEQ ID NO:7, which comprises a combination of substitutions of at least two amino acids at positions chosen from positions 6, 30 and 32 of the pro region. In turn, the second polynucleotide is operably linked to a third polynucleotide that encodes the mature region of a wild-type or variant alkaline serine protease derived from *Bacillus clausii* or *Bacillus lentus* that is at least about 60% identical to the mature protease of SEQ ID NO: 9. Preferably, the substitutions enhance the production of the mature protease by a *Bacillus* sp. host e.g. *Bacillus subtilis*.

In another embodiment, the isolated modified polynucleotide comprises a first polynucleotide that encodes a signal peptide chosen from SEQ ID NOS:3 and 5, which is operably linked to a second polynucleotide that encodes the pro region set forth in SEQ ID NO:7, which comprises a combination of substitutions of at least two amino acids at positions chosen from positions 6, 30 and 32 of the pro region. In turn, the second polynucleotide is operably linked to a third polynucleotide that encodes the mature region of a protease chosen from SEQ ID NOS:9, 11, 13, 15, 17, 19, and 21. Preferably, the substitutions enhance the production of the mature protease by a *Bacillus* sp. host e.g. *Bacillus subtilis*.

In another embodiment, the isolated modified polynucleotide comprises a first polynucleotide that encodes a signal peptide, which is operably linked to a second polynucleotide that encodes the pro region set forth in SEQ ID NO:7, which comprises a combination of substitutions of at least two amino acids chosen from E6X-E30G, E6X-E30S, E6X-A32K, E30X-A32K, E30G-A32X, E30S-A32X and E6G-E30G-A32X. In turn, the second polynucleotide is operably linked to a third polynucleotide that encodes the mature region of a protease that is at least about 60% identical to the mature protease of SEQ ID NO: 9. Preferably, the substitutions enhance the production of the mature protease by a *Bacillus* sp. host e.g. *Bacillus subtilis*.

In another embodiment, the isolated modified polynucleotide comprises a first polynucleotide that encodes a signal peptide, which is operably linked to a second polynucleotide that encodes the pro region set forth in SEQ ID NO:7, which comprises a combination of substitutions of at least two amino acids chosen from E6X-E30G, E6X-E30S, E6X-A32K, E30X-A32K, E30G-A32X, E30S-A32X and E6G-E30G-A32X. In turn, the second polynucleotide is operably linked to a third polynucleotide that encodes the mature region of a wild-type or variant alkaline serine protease derived from *Bacillus clausii* or *Bacillus lentus* that is at least about 60% identical to the mature protease of SEQ ID NO: 9. Preferably, the substitutions enhance the production of the mature protease by a *Bacillus* sp. host e.g. *Bacillus subtilis*.

In another embodiment, the isolated modified polynucleotide comprises a first polynucleotide that encodes a signal peptide, which is operably linked to a second polynucleotide that encodes the pro region set forth in SEQ ID NO:7, which comprises a combination of substitutions of at least two amino acids chosen from E6X-E30G, E6X-E30S, E6X-A32K, E30X-A32K, E30G-A32X, E30S-A32X and E6G-E30G-A32X. In turn, the second polynucleotide is operably linked to a third polynucleotide that encodes the mature region of a protease chosen from SEQ ID NOS:9, 11, 13, 15, 17, 19, and 21. Preferably, the substitutions enhance the production of the mature protease by a *Bacillus* sp. host e.g. *Bacillus subtilis*.

In another embodiment, the invention provides an isolated modified polynucleotide that encodes a modified protease. The isolated modified polynucleotide comprises a first polynucleotide that encodes a signal peptide chosen from SEQ ID NOS:3 and 5, which is operably linked to a second polynucleotide that encodes the pro region set forth in SEQ ID NO:7, which comprises a combination of substitutions of at least two amino acids chosen from E6X-E30G, E6X-E30S, E6X-A32K, E30X-A32K, E30G-A32X, E30S-A32X and E6G-E30G-A32X. In turn, the second polynucleotide is operably linked to a third polynucleotide that encodes the mature region of a protease that is at least about 60% identical to the mature protease of SEQ ID NO: 9. Preferably, the substitutions enhance the production of the mature protease by a *Bacillus* sp. host e.g. *Bacillus subtilis*.

In another embodiment, the isolated modified polynucleotide comprises a first polynucleotide that encodes a signal peptide chosen from SEQ ID NOS:3 and 5, which is operably linked to a second polynucleotide that encodes the pro region set forth in SEQ ID NO:7, which comprises a combination of substitutions of at least two amino acids chosen from E6X-E30G, E6X-E30S, E6X-A32K, E30X-A32K, E30G-A32X, E30S-A32X and E6G-E30G-A32X. In turn, the second polynucleotide is operably linked to a third polynucleotide that encodes the mature region of a wild-type or variant alkaline serine protease derived from *Bacillus clausii* or *Bacillus lentus* that is at least about 60% identical to the mature protease of SEQ ID NO: 9. Preferably, the substitutions enhance the production of the mature protease by a *Bacillus* sp. host e.g. *Bacillus subtilis*.

In another embodiment, the isolated modified polynucleotide comprises a first polynucleotide that encodes a signal peptide chosen from SEQ ID NOS:3 and 5, which is operably linked to a second polynucleotide that encodes the pro region set forth in SEQ ID NO:7, which comprises a combination of substitutions of at least two amino acids chosen from E6X-E30G, E6X-E30S, E6X-A32K, E30X-A32K, E30G-A32X, E30S-A32X and E6G-E30G-A32X. In turn, the second polynucleotide is operably linked to a third polynucleotide that encodes the mature region of a protease chosen from SEQ ID NOS:9, 11, 13, 15, 17, 19, and 21. Preferably, the substitutions enhance the production of the mature protease by a *Bacillus* sp. host e.g. *Bacillus subtilis*.

In another embodiment, the isolated modified polynucleotide comprises a first polynucleotide that encodes a signal peptide, which is operably linked to a second polynucleotide that encodes the pro region set forth in SEQ ID NO:7, which comprises a combination of substitutions of at least two amino acids chosen from E6R-A32K, E6N-A32K, E6D-A32K, E6I-A32K, E6K-A32K, E6M-A32K, E6P-A32K, E6S-A32K, E6T-A32K, E6N-A32K, E30W-A32K, E30V-A32K, E6A-E30G, E6R-E30G, E6C-E30G, E6Q-E30G, E6G-E30G, E6H-E30G, E6K-E30G, E6S-E30G, E6W-E30G, E30G-A32R, E30G-A32Q, E30G-A32E, E30G-A32G, E30G-A32H, E30G-A32I, E30G-A32K, E30G-A32S, E30G-A32T, E30G-A32W, E30G-A32V, E6G-E30G-A32E, E6G-E30G-A32S, E6G-E30G-A32T, E6G-E30G-A32W, E6A-E30G, E6R-E30G, E6N-E30G, E6D-E30G, E6C-E30G, E6Q-E30G, E6G-E30G, E6H-E30G, E6K-E30G, E6M-E30G, E6F-E30G, E6P-E30G, E6S-E30G, E6T-E30G, E6W-E30G, E6V-E30G, E6Y-E30G, E6A-E30S, E6G-E30S, E6L-E30S, E6K-E30S, E6F-E30S, E6P-E30S, E6Y-E30S, E6V-E30S, E30S-A32R, E30S-A32N, E30S-A32D, E30S-A32C, E30S-A32Q, E30S-A32E, E30S-A32G, E30S-A32H, E30S-A32L, E30S-A32K, E30S-A32M, E30S-A32F, E30S-A32P, E30S-A32S, E30S-A32T, E30S-A32W, E30S-A32Y, and E30S-A32V. In turn, the second polynucleotide is operably linked to a third polynucleotide that encodes the mature region of a protease that is at least about 60% identical to the mature protease of SEQ ID NO: 9. Preferably, the substitutions enhance the production of the mature protease by a *Bacillus* sp. host e.g. *Bacillus subtilis*.

In another embodiment, the isolated modified polynucleotide comprises a first polynucleotide that encodes a signal peptide, which is operably linked to a second polynucleotide that encodes the pro region set forth in SEQ ID NO:7, which comprises a combination of substitutions of at least two amino acids chosen from E6R-A32K, E6N-A32K, E6D-A32K, E6I-A32K, E6K-A32K, E6M-A32K, E6P-A32K, E6S-A32K, E6T-A32K, E6N-A32K, E30W-A32K, E30V-A32K, E6A-E30G, E6R-E30G, E6C-E30G, E6Q-E30G, E6G-E30G, E6H-E30G, E6K-E30G, E6S-E30G, E6W-E30G, E30G-A32R, E30G-A32Q, E30G-A32E, E30G-A32G, E30G-A32H, E30G-A32I, E30G-A32K, E30G-A32S, E30G-A32T, E30G-A32W, E30G-A32V, E6G-E30G-A32E, E6G-E30G-A32S, E6G-E30G-A32T, E6G-E30G-A32W, E6A-E30G, E6R-E30G, E6N-E30G, E6D-E30G, E6C-E30G, E6Q-E30G, E6G-E30G, E6H-E30G, E6K-E30G, E6M-E30G, E6F-E30G, E6P-E30G, E6S-E30G, E6T-E30G, E6W-E30G, E6V-E30G, E6Y-E30G, E6A-E30S, E6G-E30S, E6L-E30S, E6K-E30S, E6F-E30S, E6P-E30S, E6Y-E30S, E6V-E30S, E30S-A32R, E30S-A32N, E30S-A32D, E30S-A32C, E30S-A32Q, E30S-A32E, E30S-A32G, E30S-A32H, E30S-A32L, E30S-A32K, E30S-A32M, E30S-A32F, E30S-A32P, E30S-A32S, E30S-A32T, E30S-A32W, E30S-A32Y, and E30S-A32V. In turn, the second polynucleotide is operably linked to a third polynucleotide that encodes the mature region of a wild-type or variant alkaline serine protease derived from *Bacillus clausii* or *Bacillus lentus* that is at least about 60% identical to the mature protease of SEQ ID NO: 9. Preferably, the substitutions enhance the production of the mature protease by a *Bacillus* sp. host e.g. *Bacillus subtilis*.

In another embodiment, the isolated modified polynucleotide comprises a first polynucleotide that encodes a signal peptide, which is operably linked to a second polynucleotide that encodes the pro region set forth in SEQ ID NO:7, which comprises a combination of substitutions of at least two amino acids chosen from E6R-A32K, E6N-A32K, E6D-A32K, E6I-A32K, E6K-A32K, E6M-A32K, E6P-A32K, E6S-A32K, E6T-A32K, E6N-A32K, E30W-A32K, E30V-A32K, E6A-E30G, E6R-E30G, E6C-E30G, E6Q-E30G, E6G-E30G, E6H-E30G, E6K-E30G, E6S-E30G, E6W-E30G, E30G-A32R, E30G-A32Q, E30G-A32E, E30G-A32G, E30G-A32H, E30G-A32I, E30G-A32K, E30G-A32S, E30G-A32T, E30G-A32W, E30G-A32V, E6G-E30G-A32E, E6G-E30G-A32S, E6G-E30G-A32T, E6G-E30G-A32W, E6A-E30G, E6R-E30G, E6N-E30G, E6D-E30G, E6C-E30G, E6Q-E30G, E6G-E30G, E6H-E30G, E6K-E30G, E6M-E30G, E6F-E30G, E6P-E30G, E6S-E30G, E6T-E30G, E6W-E30G, E6V-E30G, E6Y-E30G, E6A-E30S, E6G-E30S, E6L-E30S, E6K-E30S, E6F-E30S, E6P-E30S, E6Y-E30S, E6V-E30S, E30S-A32R, E30S-A32N, E30S-A32D, E30S-A32C, E30S-A32Q, E30S-A32E, E30S-A32G, E30S-A32H, E30S-A32L, E30S-A32K, E30S-A32M, E30S-A32F, E30S-A32P, E30S-A32S, E30S-A32T, E30S-A32W, E30S-A32Y, and E30S-A32V. In turn, the second polynucleotide is operably linked to a third polynucleotide that encodes the mature region of a protease that is at least about 60% identical to the mature protease of SEQ ID NO: 9. Preferably, the substitutions enhance the production of the mature protease by a *Bacillus* sp. host e.g. *Bacillus subtilis*.

In another embodiment, the isolated modified polynucleotide comprises a first polynucleotide that encodes a signal peptide chosen from SEQ ID NOS:3 and 5, which is operably linked to a second polynucleotide that encodes the pro region set forth in SEQ ID NO:7, which comprises a combination of substitutions of at least two amino acids chosen from E6R-A32K, E6N-A32K, E6D-A32K, E6I-A32K, E6K-A32K, E6M-A32K, E6P-A32K, E6S-A32K, E6T-A32K, E6N-A32K, E30W-A32K, E30V-A32K, E6A-E30G, E6R-E30G, E6C-E30G, E6Q-E30G, E6G-E30G, E6H-E30G, E6K-E30G, E6S-E30G, E6W-E30G, E30G-A32R, E30G-A32Q, E30G-A32E, E30G-A32G, E30G-A32H, E30G-A32I, E30G-A32K, E30G-A32S, E30G-A32T, E30G-A32W, E30G-A32V, E6G-E30G-A32E, E6G-E30G-A32S, E6G-E30G-A32T, E6G-E30G-A32W, E6A-E30G, E6R-E30G, E6N-E30G, E6D-E30G, E6C-E30G, E6Q-E30G, E6G-E30G, E6H-E30G, E6K-E30G, E6M-E30G, E6F-E30G, E6P-E30G, E6S-E30G, E6T-E30G, E6W-E30G, E6V-E30G, E6Y-E30G, E6A-E30S, E6G-E30S, E6L-E30S, E6K-E30S, E6F-E30S, E6P-E30S, E6Y-E30S, E6V-E30S, E30S-A32R, E30S-A32N, E30S-A32D, E30S-A32C, E30S-A32Q, E30S-A32E, E30S-A32G, E30S-A32H, E30S-A32L, E30S-A32K, E30S-A32M, E30S-A32F, E30S-A32P, E30S-A32S, E30S-A32T, E30S-A32W, E30S-A32Y, and E30S-A32V. In turn, the second polynucleotide is operably linked to a third polynucleotide that encodes the mature region of a wild-type or variant alkaline serine protease derived from *Bacillus clausii* or *Bacillus lentus* that is at least about 60% identical to the mature protease of SEQ ID NO: 9. Preferably, the substitutions enhance the production of the mature protease by a *Bacillus* sp. host e.g. *Bacillus subtilis*.

In another embodiment, the isolated modified polynucleotide comprises a first polynucleotide that encodes a signal peptide chosen from SEQ ID NOS:3 and 5, which is operably linked to a second polynucleotide that encodes the pro region set forth in SEQ ID NO:7, which comprises a combination of substitutions of at least two amino acids chosen from E6R-A32K, E6N-A32K, E6D-A32K, E6I-A32K, E6K-A32K, E6M-A32K, E6P-A32K, E6S-A32K, E6T-A32K, E6N-A32K, E30W-A32K, E30V-A32K, E6A-E30G, E6R-E30G, E6C-E30G, E6Q-E30G, E6G-E30G, E6H-E30G, E6K-E30G, E6S-E30G, E6W-E30G, E30G-A32R, E30G-A32Q, E30G-A32E, E30G-A32G, E30G-A32H, E30G-A32I, E30G-A32K, E30G-A32S, E30G-A32T, E30G-A32W, E30G-A32V, E6G-E30G-A32E, E6G-E30G-A32S, E6G-E30G-A32T, E6G-E30G-A32W, E6A-E30G, E6R-E30G, E6N-E30G, E6D-E30G, E6C-E30G, E6Q-E30G, E6G-E30G, E6H-E30G, E6K-E30G, E6M-E30G, E6F-E30G, E6P-E30G, E6S-E30G, E6T-E30G, E6W-E30G, E6V-E30G, E6Y-E30G, E6A-E30S, E6G-E30S, E6L-E30S, E6K-E30S, E6F-E30S, E6P-E30S, E6Y-E30S, E6V-E30S, E30S-A32R, E30S-A32N, E30S-A32D, E30S-A32C, E30S-A32Q, E30S-A32E, E30S-A32G, E30S-A32H, E30S-A32L, E30S-A32K, E30S-A32M, E30S-A32F, E30S-A32P, E30S-A32S, E30S-A32T, E30S-A32W, E30S-A32Y, and E30S-A32V. In turn, the second polynucleotide is operably linked to a third polynucleotide that encodes the mature region of a wild-type or variant alkaline serine protease derived from *Bacillus clausii* or *Bacillus lentus* that is at least about 60% identical to the mature protease of SEQ ID NO: 9. Preferably, the substitutions enhance the production of the mature protease by a *Bacillus* sp. host e.g. *Bacillus subtilis*.

In another embodiment, the invention provides an expression vector comprising an isolated modified polynucleotide, which comprises a first polynucleotide that encodes a signal peptide, which is operably linked to a second polynucleotide that encodes the pro region set forth in SEQ ID NO:7 that comprises a combination of substitutions of at least two amino acids at positions chosen from positions 6, 30 and 32 of the pro region. In turn, the second polynucleotide is operably linked to a third polynucleotide that encodes the mature region of a protease that is at least about 60% identical to the mature protease of SEQ ID NO: 9. Preferably, the mature protease is a wild-type or variant alkaline serine protease derived from *Bacillus clausii* or *Bacillus lentus* e.g. SEQ ID NOS:9, 11, 13, 15, 17, 19, and 21. In some embodiments, the expression of the isolated polynucleotide is driven by the AprE promoter comprised in the expression vector.

In another embodiment, the expression vector comprises an isolated modified polynucleotide, which comprises a first polynucleotide that encodes a signal peptide chosen from SEQ ID NOS:3 and 5, which is operably linked to a second polynucleotide that encodes the pro region set forth in SEQ ID NO:7 that comprises a combination of substitutions of at least two amino acids at positions chosen from positions 6, 30 and 32 of the pro region. In turn, the second polynucleotide is operably linked to a third polynucleotide that encodes the mature region of a protease that is at least about 60% identical to the mature protease of SEQ ID NO: 9. Preferably, the mature protease is a wild-type or variant alkaline serine protease derived from *Bacillus clausii* or *Bacillus lentus* e.g. SEQ ID NOS:9, 11, 13, 15, 17, 19, and 21. In some embodiments, the expression of the isolated polynucleotide is driven by the AprE promoter comprised in the expression vector.

In another embodiment, the invention provides an expression vector comprising an isolated modified polynucleotide, which comprises a first polynucleotide that encodes a signal peptide, which is operably linked to a second polynucleotide that encodes the pro region set forth in SEQ ID NO:7 that comprises a combination of substitutions of at least two amino acids chosen from E6X-E30G, E6X-E30S, E6X-A32K, E30X-A32K, E30G-A32X, E30S-A32X and E6G-E30G-A32X. In turn, the second polynucleotide is operably linked to a third polynucleotide that encodes the mature region of a protease that is at least about 60% identical to the mature protease of SEQ ID NO: 9. Preferably, the mature protease is a wild-type or variant alkaline serine protease derived from *Bacillus clausii* or *Bacillus lentus* e.g. SEQ ID NOS:9, 11, 13, 15, 17, 19, and 21. In some embodiments, the expression of the isolated polynucleotide is driven by the AprE promoter comprised in the expression vector.

In another embodiment, the expression vector comprises an isolated modified polynucleotide, which comprises a first polynucleotide that encodes a signal peptide chosen from SEQ ID NOS:3 and 5, which is operably linked to a second polynucleotide that encodes the pro region set forth in SEQ ID NO:7 that comprises a combination of substitutions of at least two amino acids chosen from E6X-E30G, E6X-E30S, E6X-A32K, E30X-A32K, E30G-A32X, E30S-A32X and E6G-E30G-A32X. In turn, the second polynucleotide is operably linked to a third polynucleotide that encodes the mature region of a protease that is at least about 60% identical to the mature protease of SEQ ID NO: 9. Preferably, the mature protease is a wild-type or variant alkaline serine protease derived from *Bacillus clausii* or *Bacillus lentus* e.g. SEQ ID NOS:9, 11, 13, 15, 17, 19, and 21. In some embodiments, the expression of the isolated polynucleotide is driven by the AprE promoter comprised in the expression vector.

In another embodiment, the invention provides an expression vector comprising an isolated modified polynucleotide, which comprises a first polynucleotide that encodes a signal peptide, which is operably linked to a second polynucleotide that encodes the pro region set forth in SEQ ID NO:7 that comprises a combination of substitutions of at least two amino acids chosen from E6R-A32K, E6N-A32K, E6D-A32K, E6I-A32K, E6K-A32K, E6M-A32K, E6P-A32K, E6S-A32K, E6T-A32K, E6N-A32K, E30W-A32K, E30V-A32K, E6A-E30G, E6R-E30G, E6C-E30G, E6Q-E30G, E6G-E30G, E6H-E30G, E6K-E30G, E6S-E30G, E6W-E30G, E30G-A32R, E30G-A32Q, E30G-A32E, E30G-A32G, E30G-A32H, E30G-A32I, E30G-A32K, E30G-A32S, E30G-A32T, E30G-A32W, E30G-A32V, E6G-E30G-A32E, E6G-E30G-A32S, E6G-E30G-A32T, E6G-E30G-A32W, E6A-E30G, E6R-E30G, E6N-E30G, E6D-E30G, E6C-E30G, E6Q-E30G, E6G-E30G, E6H-E30G, E6K-E30G, E6M-E30G, E6F-E30G, E6P-E30G, E6S-E30G, E6T-E30G, E6W-E30G, E6V-E30G, E6Y-E30G, E6A-E30S, E6G-E30S, E6L-E30S, E6K-E30S, E6F-E30S, E6P-E30S, E6Y-E30S, E6V-E30S, E30S-A32R, E30S-A32N, E30S-A32D, E30S-A32C, E30S-A32Q, E30S-A32E, E30S-A32G, E30S-A32H, E30S-A32L, E30S-A32K, E30S-A32M, E30S-A32F, E30S-A32P, E30S-A32S, E30S-A32T, E30S-A32W, E30S-A32Y, and E30S-A32V. In turn, the second polynucleotide is operably linked to a third polynucleotide that encodes the mature region of a protease that is at least about 60% identical to the mature protease of SEQ ID NO: 9. Preferably, the mature protease is a wild-type or variant alkaline serine protease derived from *Bacillus clausii* or *Bacillus lentus* e.g. SEQ ID NOS:9, 11, 13, 15, 17, 19, and 21. In some embodiments, the expression of the isolated polynucleotide is driven by the AprE promoter comprised in the expression vector.

In another embodiment, the expression vector comprises an isolated modified polynucleotide, which comprises a first polynucleotide that encodes a signal peptide chosen from SEQ ID NOS:3 and 5, which is operably linked to a second polynucleotide that encodes the pro region set forth in SEQ ID NO:7 that comprises a combination of substitutions of at least two amino acids chosen from E6R-A32K, E6N-A32K, E6D-A32K, E6I-A32K, E6K-A32K, E6M-A32K, E6P-A32K, E6S-A32K, E6T-A32K, E6N-A32K, E30W-A32K, E30V-A32K, E6A-E30G, E6R-E30G, E6C-E30G, E6Q-E30G, E6G-E30G, E6H-E30G, E6K-E30G, E6S-E30G, E6W-E30G, E30G-A32R, E30G-A32Q, E30G-A32E, E30G-A32G, E30G-A32H, E30G-A32I, E30G-A32K, E30G-A32S, E30G-A32T, E30G-A32W, E30G-A32V, E6G-E30G-A32E, E6G-E30G-A32S, E6G-E30G-A32T, E6G-E30G-A32W, E6A-E30G, E6R-E30G, E6N-E30G, E6D-E30G, E6C-E30G, E6Q-E30G, E6G-E30G, E6H-E30G, E6K-E30G, E6M-E30G, E6F-E30G, E6P-E30G, E6S-E30G, E6T-E30G, E6W-E30G, E6V-E30G, E6Y-E30G, E6A-E30S, E6G-E30S, E6L-E30S, E6K-E30S, E6F-E30S, E6P-E30S, E6Y-E30S, E6V-E30S, E30S-A32R, E30S-A32N, E30S-A32D, E30S-A32C, E30S-A32Q, E30S-A32E, E30S-A32G, E30S-A32H, E30S-A32L, E30S-A32K, E30S-A32M, E30S-A32F, E30S-A32P, E30S-A32S, E30S-A32T, E30S-A32W, E30S-A32Y, and E30S-A32V. In turn, the second polynucleotide is operably linked to a third polynucleotide that encodes the mature region of a protease that is at least about 60% identical to the mature protease of SEQ ID NO: 9. Preferably, the mature protease is a wild-type or variant alkaline serine protease derived from *Bacillus clausii* or *Bacillus lentus* e.g. SEQ ID NOS:9, 11, 13, 15, 17, 19, and 21.

In some embodiments, the expression of the isolated polynucleotide is driven by the AprE promoter comprised in the expression vector.

In another embodiment, the invention provides a *Bacillus* sp. host cell e.g. *Bacillus subtilis*, which comprises any one of the expression vectors described above. Preferably, the substitutions comprised in the pro region of the modified polynucleotide enhance the production of the mature protease from the *Bacillus* host cell. In addition to *Bacillus subtilis*, other host cells that can be used to express the modified polynucleotides from the expression vectors include *Bacillus licheniformis, Bacillus lentus, Bacillus brevis, Bacillus stearothermophilus, Bacillus alkalophilus, Bacillus amyloliquefaciens, Bacillus clausii, Bacillus halodurans, Bacillus megaterium, Bacillus coagulans, Bacillus circulans, Bacillus lautus*, and *Bacillus thuringiensis*.

In another embodiment, the invention provides a method for producing a mature protease in a *Bacillus* sp. host cell. The method includes providing any one of the expression vectors described above, transforming the expression vector into a *Bacillus* sp. host cell, and culturing the transformed host cell under suitable conditions to produce the protease. Preferably, the host cell is a *Bacillus subtilis* host cell. However, in addition to *Bacillus subtilis*, other host cells that can be used to produce the mature proteases from the expression vector include *Bacillus licheniformis, Bacillus lentus, Bacillus brevis, Bacillus stearothermophilus, Bacillus alkalophilus, Bacillus amyloliquefaciens, Bacillus clausii, Bacillus halodurans, Bacillus megaterium, Bacillus coagulans, Bacillus circulans, Bacillus lautus*, and *Bacillus thuringiensis*.

In another embodiment, the method produces the mature protease of SEQ ID NO:9 by providing an expression vector that expresses an isolated modified polynucleotide comprising a first polynucleotide encoding the signal peptide of SEQ ID NO:3, a second polynucleotide encoding the pro region of SEQ ID NO:7 that includes a combination of substitutions chosen from E6R-A32K, E6N-A32K, E6D-A32K, E6I-A32K, E6K-A32K, E6M-A32K, E6P-A32K, E6S-A32K, E6T-A32K, E6N-A32K, E30W-A32K, E30V-A32K, and the third polynucleotide, which encodes the mature protease of SEQ ID NO:9. The expression vector is transformed into a *Bacillus* sp. host cell e.g. *Bacillus subtilis*, which is grown under suitable conditions to produce the mature protease.

In another embodiment, the method produces the mature protease of SEQ ID NO:17 by providing an expression vector that expresses an isolated modified polynucleotide comprising a first polynucleotide encoding the signal peptide of SEQ ID NO:3, a second polynucleotide encoding the pro region of SEQ ID NO:7 that includes a combination of substitutions chosen from E6A-E30G, E6R-E30G, E6C-E30G, E6Q-E30G, E6G-E30G, E6H-E30G, E6K-E30G, E6S-E30G, E6W-E30G, E30G-A32R, E30G-A32Q, E30G-A32E, E30G-A32G, E30G-A32H, E30G-A32I, E30G-A32K, E30G-A32S, E30G-A32T, E30G-A32W, E30G-A32V, E6G-E30G-A32E, E6G-E30G-A32S, E6G-E30G-A32T, and E6G-E30G-A32W, and the third polynucleotide, which encodes the mature protease of SEQ ID NO:17. The expression vector is transformed into a *Bacillus* sp. host cell e.g. *Bacillus subtilis*, which is grown under suitable conditions to produce the mature protease.

In another embodiment, the method produces the mature protease of SEQ ID NO:19 by providing an expression vector that expresses an isolated modified polynucleotide comprising a first polynucleotide encoding the signal peptide of SEQ ID NO:3, a second polynucleotide encoding the pro region of SEQ ID NO:7 that includes a combination of substitutions chosen from E6A-E30G, E6R-E30G, E6N-E30G, E6D-E30G, E6C-E30G, E6Q-E30G, E6G-E30G, E6H-E30G, E6K-E30G, E6M-E30G, E6F-E30G, E6P-E30G, E6S-E30G, E6T-E30G, E6W-E30G, E6V-E30G, and E6Y-E30G, and the third polynucleotide, which encodes the mature protease of SEQ ID NO:19. The expression vector is transformed into a *Bacillus* sp. host cell e.g. *Bacillus subtilis*, which is grown under suitable conditions to produce the mature protease.

In another embodiment, the method produces the mature protease of SEQ ID NO:21 by providing an expression vector that expresses an isolated modified polynucleotide comprising a first polynucleotide encoding the signal peptide of SEQ ID NO:3, a second polynucleotide encoding the pro region of SEQ ID NO:7 that includes a combination of substitutions chosen from E6A-E30S, E6G-E30S, E6L-E30S, E6K-E30S, E6F-E30S, E6P-E30S, E6Y-E30S, E6V-E30S, E30S-A32R, E30S-A32N, E30S-A32D, E30S-A32C, E30S-A32Q, E30S-A32E, E30S-A32G, E30S-A32H, E30S-A32L, E30S-A32K, E30S-A32M, E30S-A32F, E30S-A32P, E30S-A32S, E30S-A32T, E30S-A32W, E30S-A32Y, and E30S-A32V, and the third polynucleotide, which encodes the mature protease of SEQ ID NO:21. The expression vector is transformed into a *Bacillus* sp. host cell e.g. *Bacillus subtilis*, which is grown under suitable conditions to produce the mature protease.

In other embodiments, the isolated modified polynucleotides comprise one amino acid substitution, which preferably enhances the production of a mature protease from a *Bacillus* sp. host cell. In one embodiment, the isolated modified polynucleotide comprises a first polynucleotide encoding the signal peptide of SEQ ID NO:3, and that is operably linked to a second polynucleotide that encodes the pro region set forth in SEQ ID NO:7, which comprises the substitution of an amino acid chosen from E6A, E6R, E6C, E6Q, E6H, E6I, E6K, E6M, E6S, E6Y, E30A, E30R, E30N, E30D, E30Q, E30G, E30L, E30M, E30P, E30S, E30T, E30W, E30Y, E30V, A32, A32R, A32C, A32E, A32G, A32L, A32K, A32F, A32T, A32Y, and A32V. The second polynucleotide is operably linked to a third polynucleotide that encodes the mature region of the protease of SEQ ID NO:17.

In another embodiment, the isolated modified polynucleotide comprises a first polynucleotide encoding the signal peptide of SEQ ID NO:3, and that is operably linked to a second polynucleotide that encodes the pro region set forth in SEQ ID NO:7, which comprises the substitution of an amino acid chosen from E6A, E6R, E6N, E6C, E6Q, E6G, E6H, E6M, E6F, E6P, E6S, E6T, E6W, E6V, A32K, A32T, and A32V. The second polynucleotide is operably linked to a third polynucleotide that encodes the mature region of the protease of SEQ ID NO:9.

In another embodiment, the isolated modified polynucleotide comprises a first polynucleotide encoding the signal peptide of SEQ ID NO:3, and that is operably linked to a second polynucleotide that encodes the pro region set forth in SEQ ID NO:7, which comprises the substitution of an amino acid chosen from E6A, E6H, E6K, and E6R, E30A, E30R, E30N, E30D, E30G, E30H, E30L, E30K, E30F, E30S, E30T, and E30V. The second polynucleotide is operably linked to a third polynucleotide that encodes the mature region of the protease of SEQ ID NO:19.

In another embodiment, the isolated modified polynucleotide comprises a first polynucleotide encoding the signal peptide of SEQ ID NO:3, and that is operably linked to a second polynucleotide that encodes the pro region set forth in SEQ ID NO:7, which comprises the substitution of an amino acid chosen from E6A, E6R, E6Q, E6G, E6L, E6K, E6M, E6F, E6T, E6V, E30R, E30Q, E30G, E30I, E30L, E30M, E30F, E30P, E30T, E30W, E30Y, E30V, A32Q, A32S, A32T, and A32V. The second polynucleotide is operably linked to a third polynucleotide that encodes the mature region of the protease of SEQ ID NO:11.

In another embodiment, the isolated modified polynucleotide comprises a first polynucleotide encoding the signal peptide of SEQ ID NO:3, and that is operably linked to a second polynucleotide that encodes the pro region set forth in SEQ ID NO:7, which comprises the substitution of an amino acid chosen from E30A, E30R, E30N, E30D, E30C, E30G, E30H, E30M, E30F, E30S, E30W, A32L, A32F, and A32V. The second polynucleotide is operably linked to a third polynucleotide that encodes the mature region of the protease of SEQ ID NO:21.

The method for producing the mature proteases expressed from modified polynucleotides comprising two or three substitutions in the pro region is also used for producing mature proteases expressed from modified polynucleotides comprising single amino acid substitutions.

In one embodiment, the method includes providing any one of the expression vectors described above and containing a modified polynucleotide comprising a single amino acid substitution in the pro region, transforming the expression vector into a Bacillus sp. host cell, and culturing the transformed host cell under suitable conditions to produce the protease. Preferably, the host cell is a Bacillus subtilis host cell. However, in addition to Bacillus subtilis, other host cells that can be used to produce the mature proteases from the expression vector include Bacillus licheniformis, Bacillus lentus, Bacillus brevis, Bacillus stearothermophilus, Bacillus alkalophilus, Bacillus amyloliquefaciens, Bacillus clausii, Bacillus halodurans, Bacillus megaterium, Bacillus coagulans, Bacillus circulans, Bacillus lautus, and Bacillus thuringiensis.

In one embodiment, the method produces the mature protease of SEQ ID NO:17 by providing an expression vector that expresses an isolated modified polynucleotide comprising a first polynucleotide encoding the signal peptide of SEQ ID NO:3, a second polynucleotide encoding the pro region of SEQ ID NO:7 that includes a single amino acid substitution chosen from E6A, E6R, E6C, E6Q, E6H, E6I, E6K, E6M, E6S, E6Y, E30A, E30R, E30N, E30D, E30Q, E30G, E30L, E30M, E30P, E30S, E30T, E30W, E30Y, E30V, A32, A32R, A32C, A32E, A32G, A32L, A32K, A32F, A32T, A32Y, and A32V, and the third polynucleotide, which encodes the mature protease of SEQ ID NO:17. The expression vector is transformed into a Bacillus sp. host cell e.g. Bacillus subtilis, which is grown under suitable conditions to produce the mature protease.

In another embodiment, the method produces the mature protease of SEQ ID NO:9 by providing an expression vector that expresses an isolated modified polynucleotide comprising a first polynucleotide encoding the signal peptide of SEQ ID NO:3, a second polynucleotide encoding the pro region of SEQ ID NO:7 that includes a single amino acid substitution chosen from E6A, E6R, E6N, E6C, E6Q, E6G, E6H, E6M, E6F, E6P, E6S, E6T, E6W, E6V, A32K, A32T, and A32V, and the third polynucleotide, which encodes the mature protease of SEQ ID NO:9. The expression vector is transformed into a Bacillus sp. host cell e.g. Bacillus subtilis, which is grown under suitable conditions to produce the mature protease.

In another embodiment, the method produces the mature protease of SEQ ID NO:19 by providing an expression vector that expresses an isolated modified polynucleotide comprising a first polynucleotide encoding the signal peptide of SEQ ID NO:3, a second polynucleotide encoding the pro region of SEQ ID NO:7 that includes a single amino acid substitution chosen from E6A, E6H, E6K, and E6R, E30A, E30R, E30N, E30D, E30G, E30H, E30L, E30K, E30F, E30S, E30T, and E30V, and the third polynucleotide, which encodes the mature protease of SEQ ID NO:19. The expression vector is transformed into a Bacillus sp. host cell e.g. Bacillus subtilis, which is grown under suitable conditions to produce the mature protease.

In another embodiment, the method produces the mature protease of SEQ ID NO:11 by providing an expression vector that expresses an isolated modified polynucleotide comprising a first polynucleotide encoding the signal peptide of SEQ ID NO:3, a second polynucleotide encoding the pro region of SEQ ID NO:7 that includes a single amino acid substitution chosen from E6A, E6R, E6Q, E6G, E6L, E6K, E6M, E6F, E6T, E6V, E30R, E30Q, E30G, E30I, E30L, E30M, E30F, E30P, E30T, E30W, E30Y, E30V, A32Q, A32S, A32T, and A32V, and the third polynucleotide, which encodes the mature protease of SEQ ID NO:11. The expression vector is transformed into a Bacillus sp. host cell e.g. Bacillus subtilis, which is grown under suitable conditions to produce the mature protease.

In another embodiment, the method produces the mature protease of SEQ ID NO:21 by providing an expression vector that expresses an isolated modified polynucleotide comprising a first polynucleotide encoding the signal peptide of SEQ ID NO:3, a second polynucleotide encoding the pro region of SEQ ID NO:7 that includes a single amino acid substitution chosen from E30A, E30R, E30N, E30D, E30C, E30G, E30H, E30M, E30F, E30S, E30W, A32L, A32F, and A32V, and the third polynucleotide, which encodes the mature protease of SEQ ID NO:21. The expression vector is transformed into a Bacillus sp. host cell e.g. Bacillus subtilis, which is grown under suitable conditions to produce the mature protease.

BRIEF DESCRIPTION OF THE DRAWINGS

FIG. 1 shows an alignment of the amino acid sequences of the mature region of B. lentus wild-type serine protease of SEQ ID NO:9 (GG36), the B. lentus variant serine protease of SEQ ID NO:11, the B. clausii serine protease of SEQ ID NO:13, and the B. clausii variant serine proteases of SEQ ID NO:15, SEQ ID NO:17, SEQ ID NO:19, SEQ ID NO:21, SEQ ID NO:23 and SEQ ID NO:25.

FIGS. 3A and 3B show an alignment of the amino acid sequence of the mature protease (SEQ ID NO:9) with that of mature regions of proteases from various Bacillus sp. resulting from a Blast search.

FIGS. 5A and 5B show an alignment of exemplary polynucleotides (SEQ ID NOS:8, 10, 12, 14, 16, 18, 20, 22, and 24) that encode the mature proteases of SEQ ID NOS:9, 11, 13, 15, 17, 19, 21, 23, and 25, respectively. It is understood that a polypeptide may be coded for by more than one nucleotide sequence due to the degeneracy of the genetic code.

DESCRIPTION OF THE INVENTION

Figure 2:
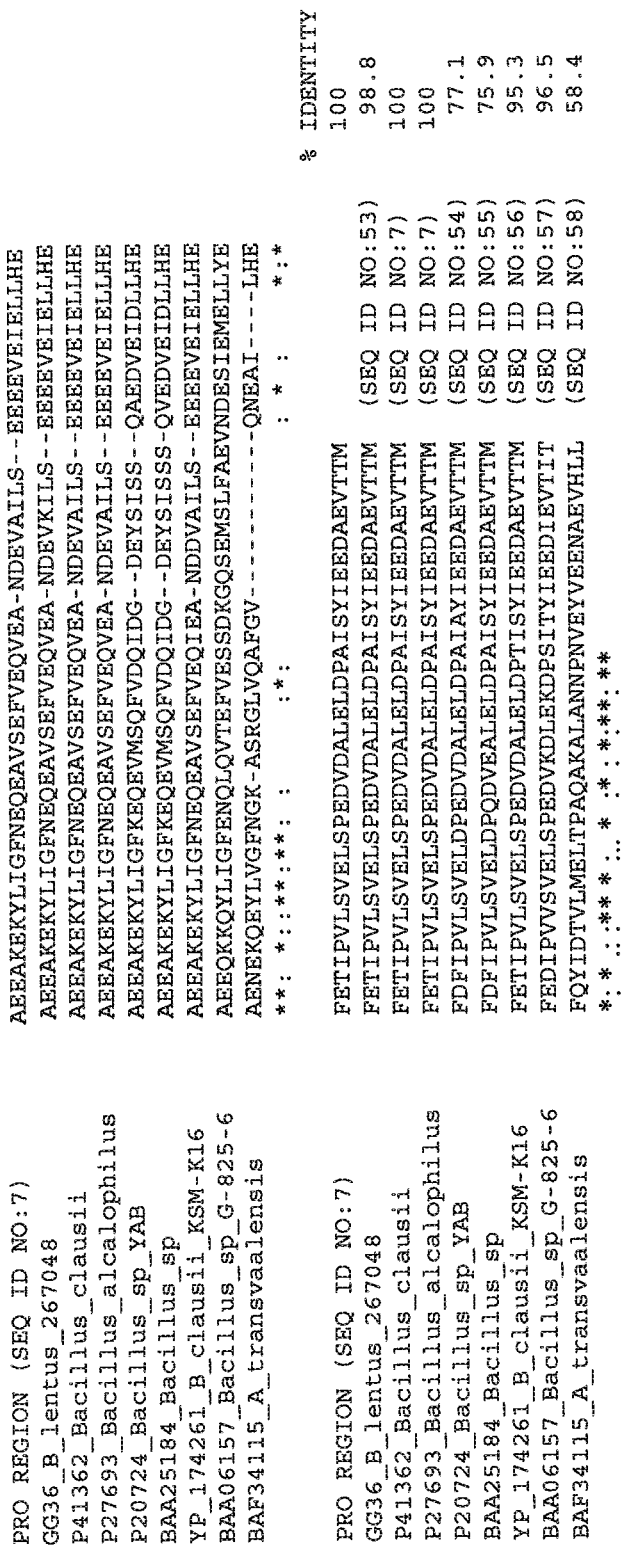
FIG. 2 shows an alignment of the amino acid sequence of the unmodified pro region of SEQ ID NO:7 with that of unmodified pro regions of proteases from various Bacillus sp. resulting from a Blast search.

This invention provides modified polynucleotides encoding modified proteases, and methods for enhancing the production of proteases in microorganisms. In particular, the modified polynucleotides comprise one or more mutations that encode proteases having modifications e.g. amino acid substitutions, of the pro region to enhance the production of the active enzyme. The present invention further relates to methods for altering the expression of proteases in microorganisms, such as *Bacillus* species.

Unless defined otherwise herein, all technical and scientific terms used herein have the same meaning as commonly understood by one of ordinary skill in the art to which this invention pertains (e.g. Singleton and Sainsbury, Dictionary of Microbiology and Molecular Biology, 2d Ed., John Wiley and Sons, NY [1994]; and Hale and Markham, The Harper Collins Dictionary of Biology, Harper Perennial, NY [1991]). Although any methods and materials similar or equivalent to those described herein find use in the practice of the present invention, the preferred methods and materials are described herein. Accordingly, the terms defined immediately below are more fully described by reference to the Specification as a whole. Also, as used herein, the singular "a", "an" and "the" includes the plural reference unless the context clearly indicates otherwise. Numeric ranges are inclusive of the numbers defining the range. Unless otherwise indicated, nucleic acids are written left to right in 5' to 3' orientation; amino acid sequences are written left to right in amino to carboxy orientation, respectively. It is to be understood that this invention is not limited to the particular methodology, protocols, and reagents described, as these may vary, depending upon the context they are used by those of skill in the art.

It is intended that every maximum numerical limitation given throughout this specification include every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

All patents, patent applications, articles and publications mentioned herein, both supra and infra, are hereby expressly incorporated herein by reference.

Furthermore, the headings provided herein are not limitations of the various aspects or embodiments of the invention which can be had by reference to the specification as a whole. Accordingly, the terms defined immediately below are more fully defined by reference to the specification as a whole. Nonetheless, in order to facilitate understanding of the invention, a number of terms are defined below.

Definitions

As used herein, the terms "isolated" and "purified" refer to a nucleic acid or amino acid (or other component) that is removed from at least one component with which it is naturally associated.

The term "modified polynucleotide" herein refers to a polynucleotide sequence that has been altered to contain at least one mutation to encode a "modified" protein.

As used herein, the terms "protease" and "proteolytic activity" refer to a protein or peptide exhibiting the ability to hydrolyze peptides or substrates having peptide linkages. Many well known procedures exist for measuring proteolytic activity (Kalisz, "Microbial Proteinases," In: Fiechter (ed.), *Advances in Biochemical Engineering/Biotechnology*, [1988]). For example, proteolytic activity may be ascertained by comparative assays which analyze the produced protease's ability to hydrolyze a commercial substrate. Exemplary substrates useful in such analysis of protease or proteolytic activity, include, but are not limited to di-methyl casein (Sigma C-9801), bovine collagen (Sigma C-9879), bovine elastin (Sigma E-1625), and bovine keratin (ICN Biomedical 902111). Colorimetric assays utilizing these substrates are well known in the art (See e.g., WO 99/34011; and U.S. Pat. No. 6,376,450, both of which are incorporated herein by reference. The AAPF assay (See e.g., Del Mar et al., Anal. Biochem., 99:316-320 [1979]) also finds use in determining the production of mature protease. This assay measures the rate at which p-nitroaniline is released as the enzyme hydrolyzes the soluble synthetic substrate, succinyl-alanine-alanine-proline-phenylalanine-p-nitroanilide (sAAPF-pNA). The rate of production of yellow color from the hydrolysis reaction is measured at 410 nm on a spectrophotometer and is proportional to the active enzyme concentration. In particular, the term "protease" herein refers to a "serine protease".

As used herein, the terms "subtilisin" and "serine protease" refer any member of the S8 serine protease family as described in MEROPS—The Peptidase Data base (Rawlings et al., MEROPS: the peptidase database, Nucleic Acids Res, 34 Database issue, D270-272, 2006, at the website merops.sanger.ac.uk/cgi-bin/merops.cgi?id=s08;action=.). The following information was derived from MEROPS—The Peptidase Data base as of Nov. 6, 2008 "Peptidase family S8 contains the serine endopeptidase serine protease and its homologues (Biochem J, 290:205-218, 1993). Family S8, also known as the subtilase family, is the second largest family of serine peptidases, and can be divided into two subfamilies, with subtilisin (S08.001) the type-example for subfamily S8A and kexin (S08.070) the type-example for subfamily S8B. Tripeptidyl-peptidase II (TPP-II; S08.090) was formerly considered to be the type-example of a third subfamily, but has since been determined to be misclassified.

The term "parent protease" herein refers to a full-length protease comprising pre, pro and mature regions that are naturally expressed in combination. In some embodiments, the pre and/or pro and/or mature regions of a parent protease serve to originate the pre and/or pro and/or mature regions of a precursor protease.

The term "precursor protease" herein refers to an unmodified full-length protease comprising a signal peptide, a pro region and a mature region. The precursor protease can be derived from naturally-occurring i.e. wild-type proteases, or from variant proteases. It is the pro region of a precursor protease that is modified to generate a modified protease. In some embodiments, the precursor protease comprises a pro region and a mature region that are derived from one parent protease. In other embodiments, the precursor protease is a chimeric protein that comprises a pro region that is derived from one parent protease and a mature region that is derived from a different parent protease.

The term "chimeric" or "fusion" when used in reference to a protein, herein refer to a protein created through the joining of two or more polynucleotides which originally coded for separate proteins. Translation of this fusion polynucleotide results in a single chimeric polynucleotide with functional properties derived from each of the original proteins. Recombinant fusion proteins are created artificially by recombinant DNA technology. A "chimeric polypeptide," or "chimera" means a protein containing sequences from more than one polypeptide. A modified protease can be chimeric in the sense that it contains a portion, region, or domain from one protease fused to one or more portions, regions, or domains from one or more other protease. By way of example, a chimeric protease might comprise the mature region of one protease linked to the pro peptide of another protease. The skilled artisan will appreciate that chimeric polypeptides and proteases need not consist of actual fusions of the protein sequences, but rather, polynucleotides with the corresponding encoding sequences can also be used to express chimeric polypeptides or proteases.

"Naturally-occurring" or "wild-type" herein refer to a protease, or a polynucleotide encoding a protease having the unmodified amino acid sequence identical to that found in nature. Naturally occurring enzymes include native enzymes, those enzymes naturally expressed or found in the particular microorganism. A sequence that is wild-type or naturally-occurring refers to a sequence from which a variant is derived. The wild-type sequence may encode either a homologous or heterologous protein.

As used herein, "variant" refers to a mature protein which differs from its corresponding wild-type mature protein by the addition of one or more amino acids to either or both the C- and N-terminal end, substitution of one or more amino acids at one or a number of different sites in the amino acid sequence, deletion of one or more amino acids at either or both ends of the protein or at one or more sites in the amino acid sequence, and/or insertion of one or more amino acids at one or more sites in the amino acid sequence of the mature protein. Variant proteins encompass naturally-occurring variants and genetically engineered variant proteins. A variant protein in the context of the present invention is exemplified by the *B. lentus* protease of SEQ ID NO:11, which is a variant of the naturally-occurring protein *B. lentus* protease GG36 (SEQ ID NO:9), from which it differs by three amino acid substitutions at positions 74, 101 and 102 of the mature region. Another example of a variant protease is the *B. clausii* protease SEQ ID NO:19, which is a variant of the naturally-occurring protein *B. clausii* protease Maxacal (SEQ ID NO:13), from which it differs by two amino acid substitutions at positions 99 and 102 of the mature region (FIG. 1).

As used herein, "homolog" and "homologous protein" refers to a protein (e.g., protease) that has similar action and/or structure, as a protein of interest (e.g., a protease from another source). It is not intended that homologs be necessarily related evolutionarily. Thus, it is intended that the term encompass the same or similar enzyme(s) (i.e., in terms of structure and function) obtained from different species.

The terms "derived from" and "obtained from" refer to not only a protease produced or producible by a strain of the organism in question, but also a protease encoded by a DNA sequence isolated from such strain and produced in a host organism containing such DNA sequence. Additionally, the term refers to a protease which is encoded by a DNA sequence of synthetic and/or cDNA origin and which has the identifying characteristics of the protease in question. To exemplify, "proteases derived from *Bacillus*" refers to those enzymes having proteolytic activity which are naturally-produced by *Bacillus*, as well as to serine proteases like those produced by *Bacillus* sources but which through the use of genetic engineering techniques are produced by non-*Bacillus* organisms transformed with a nucleic acid encoding said serine proteases.

A "modified full-length protease", a "modified precursor protease" or a "modified protease" are interchangeably used to refer to a full-length protease that comprises a signal peptide, a mature region and a pro region that are derived from a parent or precursor protease, wherein the pro region is modified to contain at least one mutation. In some embodiments, the pro region and the mature region are derived from the same parent protease. In other embodiments, the pro region and the mature region are derived from different parent proteases. The modified protease comprises a pro region that is modified to contain at least one mutation, and it is encoded by a modified polynucleotide. The amino acid sequence of the modified protease is said to be "generated" from the parent protease amino acid sequence by introducing into the pro region of the parent amino acid sequence at least one mutation e.g. a substitution, deletion or insertion of one or more amino acids. In some embodiments, one or more amino acids of the pro region of the precursor protease are substituted to generate the modified full-length protease. Such modification is of the "precursor" DNA sequence which encodes the amino acid sequence of the "precursor" protease rather than manipulation of the precursor protease per se.

The term "unmodified" when used in reference to a protease polypeptide or polynucleotide, herein refers to a protease comprising a pro region that has not been modified to comprise at least one mutation e.g. a substitution.

The terms "full-length protein" and "pre-pro-protein" herein refer to a gene product comprising a signal peptide, a pro sequence and a mature sequence. For example, the full-length protease of SEQ ID NO:59 comprises the signal peptide (pre region) (SEQ ID NO:3, encoded for example by the pre polynucleotide of SEQ ID NO:2), the pro region (SEQ ID NO:7, encoded for example by the pre polynucleotide of SEQ ID NO:6), and the mature region (SEQ ID NO:9 encoded by the polynucleotide of SEQ ID NO:8).

The term "signal sequence", "signal peptide" or "pre region" refers to any sequence of nucleotides and/or amino acids which may participate in the secretion of the mature or precursor forms of the protein. This definition of signal sequence is a functional one, meant to include all those amino acid sequences encoded by the N-terminal portion of the protein gene, which participate in the effectuation of the secretion of protein. To exemplify, a pre peptide of a protease of the present invention at least includes the amino acid sequence identical to residues 1-29 of SEQ ID NO:3.

The term "pro sequence" or "pro region" is an amino acid sequence between the signal sequence and mature protease that is necessary for the secretion/production of the protease. Cleavage of the pro sequence will result in a mature active protease. To exemplify, a pro region of a protease of the present invention at least includes the amino acid sequence identical to residues 1-84 of the pro region of SEQ ID NO:7, which correspond to amino acids 30-113 of the full-length protease of SEQ ID NO:59.

The terms "mature form" or "mature region" refer to the final functional portion of the protein. To exemplify, a mature form of the protease of the present invention includes the amino acid sequence identical to residues 1-269 of SEQ ID NO:9. In this context, the "mature form" is "processed from" a full-length protease, wherein the processing of the full-length protease encompasses the removal of the signal peptide and the removal of the pro region.

The terms "pro-protein", "pro-polypeptide" and "pro-protease", herein refer to a protein comprising the mature form operably linked to a pro-polypeptide. A "pro-polypeptide" is encoded by a "pro-polynucleotide".

As used herein, the term "heterologous protein" refers to a protein or polypeptide that does not naturally occur in the host cell. Similarly, a "heterologous polynucleotide" refers to a polynucleotide that does not naturally occur in the host cell. Heterologous polypeptides and/or heterologous polynucleotides include chimeric polypeptides and/or polynucleotides.

As used herein, "substituted" and "substitutions" refer to replacement(s) of an amino acid residue or nucleic acid base in a parent sequence. In some embodiments, the substitution involves the replacement of a naturally occurring residue or base. The modified proteases herein encompass the substitution of any one of the 84 amino acids of the pro region of the precursor protease by any one of the remaining nineteen amino acids. For example, the substitution at position 6 (E6) is a replacement of a glutamic acid (E) with one of the group consisting of alanine (A), cysteine (C), aspartic acid (D), glycine (G), phenylalanine (F), histidine (H), isoleucine (I), lysine (K), leucine (L), methionine (M), asparagine (N), proline (P), glutamine (Q), arginine (R), serine (S), threonine (T), valine (V), thryptophan (W), and tyrosine (Y). A substitution of an amino acid e.g. E6, for any other amino acid at the same position is denoted by E6X, wherein X is one of the remaining 19 amino acids that substitutes E at position 6. In some embodiments, two or more amino acids are substituted to generate a modified protease that comprises a combination of amino acid substitutions. For example, a combination of a substitution of amino acid E at position 6 for amino acid A in combination with the substitution of amino acid E at position 30 for amino acid T is denoted as E6A-E30T. Amino acid positions for the substitutions in the pro region are numbered corresponding to the numbered position in the pro region of SEQ ID NO:7.

As used herein, "by correspondence to", "corresponding to," or "equivalent to" refers to a residue at the enumerated position in a protein or peptide, or a residue that is analogous, homologous, or equivalent to an enumerated residue in a protein or peptide. As used herein, "corresponding region," generally refers to an analogous position along related proteins or a reference protein.

The terms "pre polynucleotide", "pro nucleotide" and "mature polynucleotide" herein refer to the polynucleotide sequences that respectively encode for the pre, pro and mature regions of a protein e.g. a protease.

The term "production" with reference to a protease, encompasses the two processing steps of a full-length protease including: 1. the removal of the signal peptide, which is known to occur during protein secretion; and 2. the removal of the pro region, which creates the active mature form of the enzyme and which is known to occur during the maturation process (Wang et al., Biochemistry 37:3165-3171 (1998); Power et al., Proc Natl Acad Sci USA 83:3096-3100 [1986]). The term "enhanced production" herein refers to the production of a mature protease that is processed from a modified full-length protease, and which occurs at a level that is greater than the level of production of the same mature protease when processed from an unmodified full-length protease.

The term "processed" with reference to a mature protease refers to the maturation process that a full-length protein e.g. a full-length protease, undergoes to become an active mature enzyme.

"Activity" with respect to enzymes means "catalytic activity" and encompasses any acceptable measure of enzyme activity, such as the rate of activity, the amount of activity, or the specific activity. Catalytic activity refers to the ability to catalyze a specific chemical reaction, such as the hydrolysis of a specific chemical bond. As the skilled artisan will appreciate, the catalytic activity of an enzyme only accelerates the rate of an otherwise slow chemical reaction. Because the enzyme only acts as a catalyst, it is neither produced nor consumed by the reaction itself. The skilled artisan will also appreciate that not all polypeptides have a catalytic activity. "Specific activity" is a measure of activity of an enzyme per unit of total protein or enzyme. Thus, specific activity may be expressed by unit weight (e.g. per gram, or per milligram) or unit volume (e.g. per ml) of enzyme. Further, specific activity may include a measure of purity of the enzyme, or can provide an indication of purity, for example, where a standard of activity is known, or available for comparison. The amount of activity reflects to the amount of enzyme that is produced by the host cell that expresses the enzyme being measured.

The term "relative activity" or "ratio of production" are used herein interchangeably to refer to the ratio of the enzymatic activity of a mature protease that was processed from a modified protease to the enzymatic activity of a mature protease that was processed from an unmodified protease. The ratio of production is determined by dividing the value of the activity of the protease processed from a modified precursor by the value of the activity of the same protease when processed from an unmodified precursor. The relative activity is the ratio of production expressed as a percentage.

As used herein, the term "expression" refers to the process by which a polypeptide is produced based on the nucleic acid sequence of a gene. The process includes both transcription and translation.

The term "percent (%) identity" is defined as the percentage of amino acid/nucleotide residues in a candidate sequence that are identical with the amino acid residues/nucleotide residues of the precursor sequence (i.e., the parent sequence). A % amino acid sequence identity value is determined by the number of matching identical residues divided by the total number of residues of the "longer" sequence in the aligned region. Amino acid sequences may be similar, but are not "identical" where an amino acid is substituted, deleted, or inserted in the subject sequence relative to the reference sequence. For proteins, the percent sequence identity is preferably measured between sequences that are in a similar state with respect to posttranslational modification. Typically, the "mature sequence" of the subject protein, i.e., that sequence which remains after processing to remove a signal sequence, is compared to a mature sequence of the reference protein. In other instances, a precursor sequence of a subject polypeptide sequence may be compared to the precursor of the reference sequence.

As used herein, the term "promoter" refers to a nucleic acid sequence that functions to direct transcription of a downstream gene. In some embodiments, the promoter is appropriate to the host cell in which the target gene is being expressed. The promoter, together with other transcriptional and translational regulatory nucleic acid sequences (also termed "control sequences") is necessary to express a given gene. In general, the transcriptional and translational regulatory sequences include, but are not limited to, promoter sequences, ribosomal binding sites, transcriptional start and stop sequences, translational start and stop sequences, and enhancer or activator sequences.

A nucleic acid or a polypeptide is "operably linked" when it is placed into a functional relationship with another nucleic acid or polypeptide sequence, respectively. For example, a promoter or enhancer is operably linked to a coding sequence if it affects the transcription of the sequence; a ribosome binding site is operably linked to a coding sequence if it is positioned so as to facilitate translation; or a modified pro region is operably linked to a mature region of a protease if it enables the processing of the full-length protease to produce the mature active form of the enzyme. Generally, "operably linked" means that the DNA or polypeptide sequences being linked are contiguous.

A "host cell" refers to a suitable cell that serves as a host for an expression vector comprising DNA according to the present invention. A suitable host cell may be a naturally occurring or wild-type host cell, or it may be an altered host cell. In one embodiment, the host cell is a Gram positive microorganism. In some embodiments, the term refers to cells in the genus *Bacillus*.

As used herein, "Bacillus sp." includes all species within the genus "Bacillus," as known to those of skill in the art, including but not limited to B. subtilis, B. licheniformis, B. lentus, B. brevis, B. pumilis, B. stearothermophilus, B. alkalophilus, B. amyloliquefaciens, B. clausii, B. halodurans, B. megaterium, B. coagulans, B. circulans, B. lautus, and B. thuringiensis. It is recognized that the genus Bacillus continues to undergo taxonomical reorganization. Thus, it is intended that the genus include species that have been reclassified, including but not limited to such organisms as B. stearothermophilus, which is now named "Geobacillus stearothermophilus." The production of resistant endospores in the presence of oxygen is considered the defining feature of the genus Bacillus, although this characteristic also applies to the recently named Alicyclobacillus, Amphibacillus, Aneurinibacillus, Anoxybacillus, Brevibacillus, Filobacillus, Gracilibacillus, Halobacillus, Paenibacillus, Salibacillus, Thermobacillus, Ureibacillus, and Virgibacillus.

The terms "polynucleotide" and "nucleic acid", used interchangeably herein, refer to a polymeric form of nucleotides of any length. These terms include, but are not limited to, a single-, double-stranded DNA, genomic DNA, cDNA, or a polymer comprising purine and pyrimidine bases, or other natural, chemically, biochemically modified, non-natural or derivatized nucleotide bases. Non-limiting examples of polynucleotides include genes, gene fragments, chromosomal fragments, ESTs, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. It will be understood that, as a result of the degeneracy of the genetic code, a multitude of nucleotide sequences encoding a given protein may be produced.

As used herein, the terms "DNA construct" and "transforming DNA" are used interchangeably to refer to DNA used to introduce sequences into a host cell or organism. The DNA construct may be generated in vitro by PCR or any other suitable technique(s) known to those in the art. In some embodiments, the DNA construct comprises a sequence of interest (e.g., a sequence encoding a modified protease). In some embodiments, the sequence is operably linked to additional elements such as control elements (e.g., promoters, etc.). The DNA construct may further comprise a selectable marker. In some embodiments, the DNA construct comprises sequences homologous to the host cell chromosome. In other embodiments, the DNA construct comprises non-homologous sequences. Once the DNA construct is assembled in vitro it may be used to mutagenize a region of the host cell chromosome (i.e., replace an endogenous sequence with a heterologous sequence).

As used herein, the term "expression cassette" refers to a nucleic acid construct generated recombinantly or synthetically, with a series of specified nucleic acid elements that permit transcription of a particular nucleic acid in a target cell. The recombinant expression cassette can be incorporated into a vector such as a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In some embodiments, expression vectors have the ability to incorporate and express heterologous DNA fragments in a host cell. Many prokaryotic and eukaryotic expression vectors are commercially available. Selection of appropriate expression vectors is within the knowledge of those of skill in the art. The term "expression cassette" is used interchangeably herein with "DNA construct," and their grammatical equivalents. Selection of appropriate expression vectors is within the knowledge of those of skill in the art.

As used herein, the term "heterologous DNA sequence" refers to a DNA sequence that does not naturally occur in a host cell. In some embodiments, a heterologous DNA sequence is a chimeric DNA sequence that is comprised of parts of different genes, including regulatory elements.

As used herein, the term "vector" refers to a polynucleotide construct designed to introduce nucleic acids into one or more cell types. Vectors include cloning vectors, expression vectors, shuttle vectors, and plasmids. In some embodiments, the polynucleotide construct comprises a DNA sequence encoding the full-length protease (e.g., modified protease or unmodified precursor protease). As used herein, the term "plasmid" refers to a circular double-stranded (ds) DNA construct used as a cloning vector, and which forms an extrachromosomal self-replicating genetic element in some eukaryotes or prokaryotes, or integrates into the host chromosome.

As used herein in the context of introducing a nucleic acid sequence into a cell, the term "introduced" refers to any method suitable for transferring the nucleic acid sequence into the cell. Such methods for introduction include but are not limited to protoplast fusion, transfection, transformation, conjugation, and transduction (See e.g., Ferrari et al., "Genetics," in Hardwood et al, (eds.), Bacillus, Plenum Publishing Corp., pages 57-72, [1989]).

As used herein, the terms "transformed" and "stably transformed" refers to a cell that has a non-native (heterologous) polynucleotide sequence integrated into its genome or as an episomal plasmid that is maintained for at least two generations.

Modified Proteases

The present invention provides methods and compositions for the production of mature proteases in bacterial host cells. The compositions include modified polynucleotides that encode modified proteases, which have at least one mutation in the pro region; the modified serine proteases encoded by the modified polynucleotides; expression cassettes, DNA constructs, and vectors comprising the modified polynucleotides that encode the modified proteases; and the bacterial host cells transformed with the vectors of the invention. The methods include methods for enhancing the production of mature proteases in bacterial host cells e.g. Bacillus sp. host cells. The produced proteases find use in the industrial production of enzymes, suitable for use in various industries, including but not limited to the cleaning, animal feed and textile processing industry.

The basic mechanism by which proteins are transported across membranes appears to be universal, with important features conserved between bacteria and eukaryotes. Because they can secrete certain proteins in large quantities into the growth medium, Bacillus species are used for the industrial production of enzymes such as alkaline serine proteases. Proteases are produced in vivo from a precursor protease known as a pre-pro-protease, which comprises a pre region, also known as signal peptide, a pro region and a mature region of the protease. Protein secretion across the Bacillus sp. cell envelope is a complex process that includes insertion of the precursor protein into the membrane and translocation of the protein across the membrane. The pre region serves as a signal peptide for protein secretion across the membrane and is hydrolyzed by a signal peptidase. The extracellular part of the maturation process involves folding of the pro-protease, self-processing of the pro region, and degradation of the pro-region to create the active mature form of the enzyme (Nagarjan V. Protein Secretion in "*Bacillus subtilis* and other Gram-Positive Bacteria" Ch. 49, p 713-726 [1993]; Ruan et al., Biochemistry, 38:8562-8571 [2009]).

In some embodiments, the invention provides a modified polynucleotide encoding a modified protease that is generated by introducing at least one mutation in the pro polynucleotide of the precursor protease. The modified polynucleotide is generated from a precursor polynucleotide that comprises a polynucleotide encoding the pro region of the protease (pro polynucleotide), and a polynucleotide encoding the mature region of the protease (mature polynucleotide), wherein the pro polynucleotide is modified to contain at least one mutation to generate a modified polynucleotide that encodes the modified protease of the invention. The precursor polynucleotide further comprises a polynucleotide encoding a signal peptide (pre polynucleotide). The pre, pro and mature regions of the unmodified protease can be derived from a wild-type or variant parent protease of animal, vegetable or microbial origin. In some embodiments, the pro and mature regions of the unmodified precursor protease are derived from one parent protease, while the pre region is derived from a different parent protease. In other embodiments, the pre, pro and mature regions are derived from three different parent proteases. In some embodiments, the parent protease is of bacterial origin. In some embodiments, the parent protease is a protease of the subtilisin type (subtilases, subtilopeptidases, EC 3.4.21.62), which comprise catalytically active amino acids, also referred to as serine proteases. In some embodiments, the parent protease is a *Bacillus* sp. protease. Preferably, the parent protease is a serine protease derived from *Bacillus clausii*, or *Bacillus lentus*.

Precursor Polynucleotides Encoding Precursor Proteases

In some embodiments, the unmodified precursor polynucleotide encodes a full-length protease comprising the mature region of a parent protease, such as a protease derived from *Bacillus clausii* and *Bacillus lentus*, homologs and variants thereof, operably linked to a polynucleotide e.g. gctgaagaaagcaaaagaaaaatatttaattg-gctttaatgagcaggaagctgtcagtgagtttgtagaacaagtagaggcaaat gacgaggtcgccattctctctgaggaa-gaggaagtcgaaattgaattgcttcat-gaatttgaaacgattcctgttttatccgttgagtt aagcccagaagatgtg-gacgcgcttgaactcgatccagcgatttcttatattgaagaggatgcagaagtaac gacaatg (SEQ ID NO:6), that encodes the pro region of SEQ ID NO:7 AEEAKEKYLIGFNEQEAVSEFVEQVEAN-DEVAILSEEEEVEIELLHEFETIPVLSVELSPEDVD ALELDPAISYIEEDAEVTTM (SEQ ID NO:7). Examples of mature parent proteases include the wild-type *B. lentus* protease AQSVPWGISRVQAPAAHNRGLTGS-GVKVAVLDTGISTHPDLNIRGGASFVPGEPSTQDGN GHGTHVAGTIAALNNSIGVLGVAPSAE-LYAVKVLGASGSGSVSSIAQGLEWAGNNGMHVA NLSLGSPSPSATLEQAVNSATSRGVLV-VAASGNSGAGSISYPARYANAMAVGATDQNNNR ASFSQYGAGLDIVAPGVNVQSTYPGST-YASLNGTSMATPHVAGAAALVKQKNPSWSNVQI RNHLKNTATSLGSTNLYGSGLVNAEAATR (SEQ ID NO:9), and variants thereof such as The protease of SEQ ID NO:11 AQSVPWGISRVQAPAAHNRGLTGS-GVKVAVLDTGISTHPDLNIRGGASFVPGEPSTQDGN GHGTHVAGTIAALDNSIGVLGVAPSAE-LYAVKVLGASGSGAISSIAQGLEWAGNNGMHVAN LSLGSPSPSATLEQAVNSATSRGVLV-VAASGNSGAGSISYPARYANAMAVGATDQNNNRA SFSQYGAGLDIVAPGVNVQSTYPGST-YASLNGTSMATPHVAGAAALVKQKNPSWSNVQIR NHLKNTATSLGSTNLYGSGLVNAEAATR (SEQ ID NO:11); the wild-type *Bacillus clausii* PB92 protease Maxacal (U.S. Pat. No. 5,217,878) AQSVPWGISRVQAPAAH-NRGLTGSGVKVAVLDTGISTHPDLNIRG-GASFVPGEPSTQDGN GHGTHVAGTIAALNNSIGVLGVAPNAE-LYAVKVLGASGSGSVSSIAQGLEWAGNNGMHVA NLSLGSPSPSATLEQAVNSATSRGVLV-VAASGNSGAGSISYPARYANAMAVGATDQNNNR ASFSQYGAGLDIVAPGVNVQSTYPGST-YASLNGTSMATPHVAGAAALVKQKNPSWSNVQI RNHLKNTATSLGSTNLYGSGLVNAEAATR; (SEQ ID NO:13), and variants thereof such as
the protease of SEQ ID NO:15 AQSVPWGISRVQAPAAH-NRGLTGSGVKVAVLDTGISTHPDLNIRG-GASFVPGEPSTQDGN GHGTHVAGTIAALNNSIGV-LGVAPNAELYAVKVLGASGSGSVSSIAQGLEWAGNN VMHVAN LSLGLQAPSATLEQAVNSATSRGVLV-VAASGNSGAGSISYPARYANAMAVGATDQNNNRA SFSQYGAGLDIVAPGVNVQSTYPGST-YASLNGTSMATPHVAGAAALVKQKNPSWSNVQIR NHLKNTATSLGSTNLYGSGLVNAEAATR; (SEQ ID NO:15),
the protease of SEQ ID NO:17 AQSVPWGISRVQAPAAH-NRGLTGSGVKVAVLDTGISTHPDLNIRG-GASFVPGEPSTQDGN GHGTHVAGTIAALNNSIGV-LGVAPNAELYAVKVLGASGMGSVSSIAQGLEWAGNN VMHVA NLSLGLQAPSATLEQAVNSATSRGVLV-VAASGNSGAGSISYPARYANAMAVGATDQNNNR ASFSQYGAGLDIVAPGVNVQSTYPGST-YASLNGTSMATPHVAGAAALVKQKNPSWSNVQI RNHLKNTATSLGSTNLYGSGLVNAEAATR; (SEQ ID NO:17),
the protease of SEQ ID NO:19 AQSVPWGISRVQAPAAH-NRGLTGSGVKVAVLDTGISTHPDLNIRG-GASFVPGEPSTQDGN GHGTHVAGTIAALNNSIGV-LGVAPNAELYAVKVLGASGGGSNSSIAQGLEWAGNN GMHVA NLSLGSPSPSATLEQAVNSATSRGVLV-VAASGNSGAGSISYPARYANAMAVGATDQNNNR ASFSQYGAGLDIVAPGVNVQSTYPGST-YASLNGTSMATPHVAGAAALVKQKNPSWSNVQI RNHLKNTATSLGSTNLYGSGLVNAEAATR; (SEQ ID NO:19),
the protease of SEQ ID NO:21 AQSVPWGISRVQAPAAH-NRGLTGSGVKVAVLDTGISTHPDLNIRG-GASFVPGEPSTQDGN GHGTHVAGTIAALDNSIGV-LGVAPRAELYAVKVLGASGSGSVSSIAQGLEWAGNN RMHVA NLSLGLQAPSATLEQAVNSATSRGVLV-VAASGNSGAGSISYPARYANAMAVGATDQNNNR ASFSQYGAGLDIVAPGVNVQSTYPGST-YASLNGTSMATPHVAGAAALVKQKNPSWSNVQI RNHLKNTATSLGSTNLYGSGLVNAEAATR; (SEQ ID NO:21),
the protease of SEQ ID NO:23 AQSVPWGISRVQAPAAH-NRGLTGSGVKVAVLDTGISTHPDLNIRG-GASFVPGEPSTQDGN GHGTHVAGTIAALDNSIGV-LGVAPRAELYAVKVLGASGSGSVSSIAQGLEWAGNN RMHVA NLSLGLQAPSATLEQAVNSATSRGVLV-VAASGNSGAGSISYPARYANAMAVGATDQNNNR ADFSQYGAGLDIVAPGVNVQSTYPGST-YASLNGTSMATPHVAGAAALVKQKNPSWSNRQI RNHLKNTATSLGSTNLYGSGLVNAEAATR; (SEQ ID NO:23), and
the protease of SEQ ID NO:25 AQSVPWGISRVQAPAAH-NRGLTGSGVKVAVLDTGISTHPDLNIRG- GASFVPGEPSTQDGN GHGTHVAGTIAALDNSIGV-
LGVAPRAELYAVKVLGASGSGSVSSIAQGLEWAGNN
GMHVA NLSLGLQAPSATLEQAVNSATSRGVLV-
VAASGNSGAGSISYPARYANAMAVGATDQNNNR
ADFSQYGAGLDIVAPGVNVQSTYPGST-
YASLNGTSMATPHVAGAAALVKQKNPSWSNVQI
RRHLKNTATSLGSTNLYGSGLVNAEAATR; (SEQ ID NO:25).

Figure 5A:
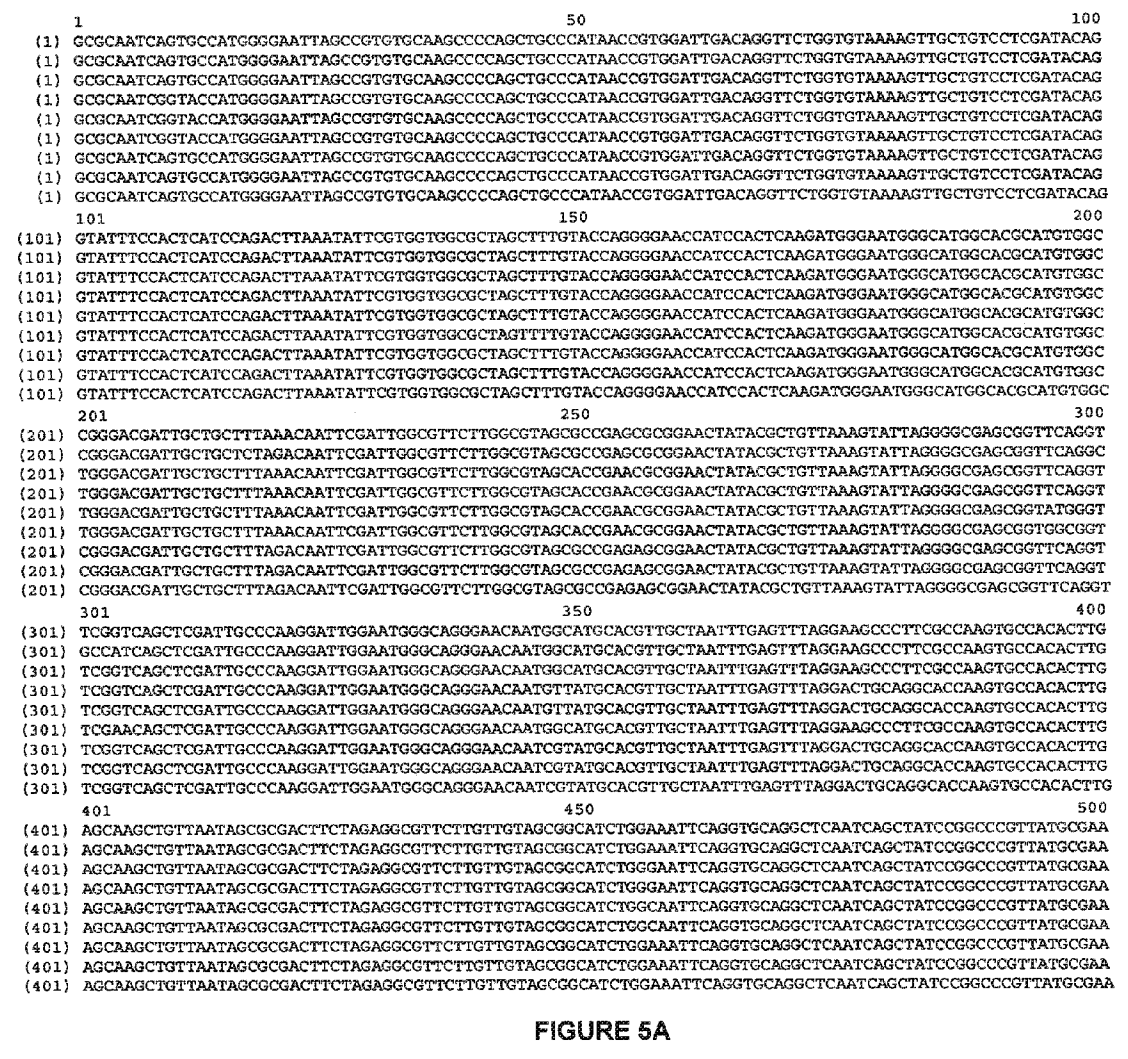

Examples of polynucleotides encoding the mature proteases of SEQ ID NOS:9, 11, 13, 15, 17, 19, 21, 23 and 25 are SEQ ID NOS:8, 10, 12, 14, 16, 18, 20, 22, and 24, respectively, shown in FIG. 5. It is understood that a polypeptide may be coded for by more than one nucleotide sequence due to the degeneracy of the genetic code.

The mature proteases of SEQ ID NOS: 9, 11, 13, 15, 17, 19, 21, 23 and 25 differ from each other by up to 9 amino acids (FIG. 1). In some embodiments, the pro polypeptide of SEQ ID NO:7 is naturally and operably linked to the mature sequences of SEQ ID NOS: 9, 11, 13, 15, 17, 19, 21, 23 and 25. Thus, in some embodiments, the precursor polynucleotides comprise polynucleotides encoding the pro region of SEQ ID NO:7 is operably linked to a mature region chosen from SEQ ID NOS: 9, 11, 13, 15, 17, 19, 21, 23 and 25, resulting in the pro-proteases of SEQ ID NOS:38-46, respectively:

```
SEQ ID NO: 38:
                                                       SEQ ID NO: 38)
AEEAKEKYLIGFNEQEAVSEFVEQVEANDEVAILSEEEEVEIELLHEFETIPVLSVELSPEDVD

ALELDPAISYIEEDAEVTTMAQSVPWGISRVQAPAAHNRGLTGSGVKVAVLDTGISTHPDLNI

RGGASFVPGEPSTQDGNGHGTHVAGTIAALNNSIGVLGVAPSAELYAVKVLGASGSGSVS

SIAQGLEWAGNNGMHVANLSLGSPSPSATLEQAVNSATSRGVLVVAASGNSGAGSISYPA

RYANAMAVGATDQNNNRASFSQYGAGLDIVAPGVNVQSTYPGSTYASLNGTSMATPHVA

GAAALVKQKNPSWSNVQIRNHLKNTATSLGSTNLYGSGLVNAEAATR;,

SEQ ID NO: 39:
                                                       SEQ ID NO: 39)
AEEAKEKYLIGFNEQEAVSEFVEQVEANDEVAILSEEEEVEIELLHEFETIPVLSVELSPEDVD

ALELDPAISYIEEDAEVTTMAQSVPWGISRVQAPAAHNRGLTGSGVKVAVLDTGISTHPDLNI

RGGASFVPGEPSTQDGNGHGTHVAGTIAALDNSIGVLGVAPSAELYAVKVLGASGSGAISSI

AQGLEWAGNNGMHVANLSLGSPSPSATLEQAVNSATSRGVLVVAASGNSGAGSISYPARY

ANAMAVGATDQNNNRASFSQYGAGLDIVAPGVNVQSTYPGSTYASLNGTSMATPHVAGA

AALVKQKNPSWSNVQIRNHLKNTATSLGSTNLYGSGLVNAEAATR;

SEQ ID NO: 40:
                                                       SEQ ID NO: 40)
AEEAKEKYLIGFNEQEAVSEFVEQVEANDEVAILSEEEEVEIELLHEFETIPVLSVELSPEDVD

ALELDPAISYIEEDAEVTTMAQSVPWGISRVQAPAAHNRGLTGSGVKVAVLDTGISTHPDLNI

RGGASFVPGEPSTQDGNGHGTHVAGTIAALNNSIGVLGVAPNAELYAVKVLGASGSGSVS

SIAQGLEWAGNNGMHVANLSLGSPSPSATLEQAVNSATSRGVLVVAASGNSGAGSISYPA

RYANAMAVGATDQNNNRASFSQYGAGLDIVAPGVNVQSTYPGSTYASLNGTSMATPHVA

GAAALVKQKNPSWSNVQIRNHLKNTATSLGSTNLYGSGLVNAEAATR;;

SEQ ID NO: 41:
                                                       SEQ ID NO: 41)
AEEAKEKYLIGFNEQEAVSEFVEQVEANDEVAILSEEEEVEIELLHEFETIPVLSVELSPEDVD

ALELDPAISYIEEDAEVTTMAQSVPWGISRVQAPAAHNRGLTGSGVKVAVLDTGISTHPDLNI

RGGASFVPGEPSTQDGNGHGTHVAGTIAALNNSIGVLGVAPNAELYAVKVLGASGSGSVS

SIAQGLEWAGNNVMHVANLSLGLQAPSATLEQAVNSATSRGVLVVAASGNSGAGSISYPA

RYANAMAVGATDQNNNRASFSQYGAGLDIVAPGVNVQSTYPGSTYASLNGTSMATPHVA

GAAALVKQKNPSWSNVQIRNHLKNTATSLGSTNLYGSGLVNAEAATR;;

SEQ ID NO: 42:
                                                       SEQ ID NO: 42)
AEEAKEKYLIGFNEQEAVSEFVEQVEANDEVAILSEEEEVEIELLHEFETIPVLSVELSPEDVD

ALELDPAISYIEEDAEVTTMAQSVPWGISRVQAPAAHNRGLTGSGVKVAVLDTGISTHPDLNI

RGGASFVPGEPSTQDGNGHGTHVAGTIAALNNSIGVLGVAPNAELYAVKVLGASGMGSVS
```

-continued

SEQ ID NO: 43:
```
                                                       SEQ ID NO: 43)
AEEAKEKYLIGFNEQEAVSEFVEQVEANDEVAILSEEEEVEIELLHEFETIPVLSVELSPEDVD

ALELDPAISYIEEDAEVTTMAQSVPWGISRVQAPAAHNRGLTGSGVKVAVLDTGISTHPDLNI

RGGASFVPGEPSTQDGNGHGTHVAGTIAALNNSIGVLGVAPNAELYAVKVLGASGGGSNS

SIAQGLEWAGNNGMHVANLSLGSPSPSATLEQAVNSATSRGVLVVAASGNSGAGSISYPA

RYANAMAVGATDQNNNRASFSQYGAGLDIVAPGVNVQSTYPGSTYASLNGTSMATPHVA

GAAALVKQKNPSWSNVQIRNHLKNTATSLGSTNLYGSGLVNAEAATR;,
```

SEQ ID NO: 44:
```
                                                       SEQ ID NO: 44)
AEEAKEKYLIGFNEQEAVSEFVEQVEANDEVAILSEEEEVEIELLHEFETIPVLSVELSPEDVD

ALELDPAISYIEEDAEVTTMAQSVPWGISRVQAPAAHNRGLTGSGVKVAVLDTGISTHPDLNI

RGGASFVPGEPSTQDGNGHGTHVAGTIAALDNSIGVLGVAPRAELYAVKVLGASGSGSVS

SIAQGLEWAGNNRMHVANLSLGLQAPSATLEQAVNSATSRGVLVVAASGNSGAGSISYPA

RYANAMAVGATDQNNNRASFSQYGAGLDIVAPGVNVQSTYPGSTYASLNGTSMATPHVA

GAAALVKQKNPSWSNVQIRNHLKNTATSLGSTNLYGSGLVNAEAATR;;
```

SEQ ID NO: 45:
```
                                                       SEQ ID NO: 45)
AEEAKEKYLIGFNEQEAVSEFVEQVEANDEVAILSEEEEVEIELLHEFETIPVLSVELSPEDVD

ALELDPAISYIEEDAEVTTMAQSVPWGISRVQAPAAHNRGLTGSGVKVAVLDTGISTHPDLNI

RGGASFVPGEPSTQDGNGHGTHVAGTIAALDNSIGVLGVAPRAELYAVKVLGASGSGSVS

SIAQGLEWAGNNRMHVANLSLGLQAPSATLEQAVNSATSRGVLVVAASGNSGAGSISYPA

RYANAMAVGATDQNNNRADFSQYGAGLDIVAPGVNVQSTYPGSTYASLNGTSMATPHVA

GAAALVKQKNPSWSNRQIRNHLKNTATSLGSTNLYGSGLVNAEAATR;;
and
```

SEQ ID NO: 46:
```
                                                      (SEQ ID NO: 46)
AEEAKEKYLIGFNEQEAVSEFVEQVEANDEVAILSEEEEVEIELLHEFETIPVLSVELSPEDVD

ALELDPAISYIEEDAEVTTMAQSVPWGISRVQAPAAHNRGLTGSGVKVAVLDTGISTHPDLNI

RGGASFVPGEPSTQDGNGHGTHVAGTIAALDNSIGVLGVAPRAELYAVKVLGASGSGSVS

SIAQGLEWAGNNGMHVANLSLGLQAPSATLEQAVNSATSRGVLVVAASGNSGAGSISYPA

RYANAMAVGATDQNNNRADFSQYGAGLDIVAPGVNVQSTYPGSTYASLNGTSMATPHVA

GAAALVKQKNPSWSNVQIRRHLKNTATSLGSTNLYGSGLVNAEAATR.
```

Other mature parent proteases that are operably linked to the pro polypeptide of SEQ ID NO:7, comprise homologs of mature proteases from *Bacillus* sp. such as P27693_*Bacillus*_*alcalophilus* e.g. SEQ ID NO:47, P20724_*Bacillus*_sp_YAB e.g. SEQ ID NO:48, BAA25184_*Bacillus*_sp e.g. SEQ ID NO:49, YP_174261_*B*_*clausii*_KSM-K16 e.g. SEQ ID NO:50, BAA06157 *Bacillus* sp G-825-6 (SEQ ID NO:51) and BAF34115_A_transvaalensis e.g. SEQ ID NO:52 (FIG. 3). In some embodiments, the unmodified precursor polynucleotide encodes a precursor protease comprising the mature region of a protease that is at least about 60%, at least about 65%, at least about 70%, at least about 75%, at least about 80%, at least about 85%, at least about 90%, at least about 95%, at least about 97%, at least about 98%, at least about 99% identical to the mature region of SEQ ID NO:9, 11, 13, 15, 17, 19, 21, 23 and 25 which is operably linked to the pro polypeptide of SEQ ID NO:7.

Subjecting the amino acid sequence of the pro region of SEQ ID NO:7 to a BLAST query revealed that in addition to being identical to the pro region of the naturally-occurring pro region of the P41362 *B. clausii* and P27693 *Bacillus alkalophilus* (FIG. 2), the pro region of SEQ ID NO:7 has a high degree of identity with the amino acid sequence of the pro region of proteases from as GG36 *B. lentus* 267048, (SEQ ID NO:53), P20724_*Bacillus*_sp_YAB (SEQ ID NO:54), BAA25184_*Bacillus*_sp (SEQ ID NO:55), YP_174261_ *B*_*clausii*_KSM-K16 e.g. SEQ ID NO:56, BAA06157 *Bacillus* sp G-825-6 (SEQ ID NO:57) and BAF34115_A_transvaalensis e.g. SEQ ID NO:58, (FIG. 2). It is expected that mutations made in the pro region of SEQ ID NOS:53-58 and corresponding to the mutations of SEQ ID NO:7 that enhance the production of the mature protease to which it is operably linked, will enhance the production of the mature protease to which the pro region of SEQ ID NOs:53-58 is operably linked. Thus, in some embodiments, the unmodified precursor polynucleotide comprises a pro polynucleotide encoding a pro polypeptide that is chosen from SEQ ID NOS:53-58 and that is operably linked to the mature protease of SEQ ID NO:9, variants and homologs thereof. For example, the pro polynucleotide encoding a pro polypeptide chosen from SEQ ID NOS:53-58 is operably linked to a variant of the mature protease of SEQ ID NO:9 e.g. SEQ ID NOS:11, 13, 15, 17, 18, 21, 23, and 25. Similarly, the pro polynucleotide encoding a pro polypeptide chosen from SEQ ID NOS:53-58 is operably linked to a homolog of the mature protease of SEQ ID NO:9 e.g. SEQ ID NOS: SEQ ID NO:47-52. In other embodiments, the unmodified precursor polynucleotide comprises a pro polynucleotide encoding a pro polypeptide that is at least about 60%, at least about 65%, at least about 70%, at least about 75%, at least about 80%, at least about 85%, at least about 90%, at least about 95%, at least about 97% or at least about 99% identical to that of SEQ ID NO:7 operably linked to the mature protease of SEQ ID NO:9 or any one of SEQ ID NOS: 11, 13, 15, 17, 18, 21, 23, and 25 and 47-52.

The percent identity shared by polynucleotide or polypeptide sequences is determined by direct comparison of the sequence information between the molecules by aligning the sequences and determining the identity by methods known in the art. An example of an algorithm that is suitable for determining sequence similarity is the BLAST algorithm, which is described in Altschul, et al., J. Mol. Biol., 215:403-410 (1990). Software for performing BLAST analyses is publicly available through the National Center for Biotechnology Information. This algorithm involves first identifying high scoring sequence pairs (HSPs) by identifying short words of length W in the query sequence that either match or satisfy some positive-valued threshold score T when aligned with a word of the same length in a database sequence. These initial neighborhood word hits act as starting points to find longer HSPs containing them. The word hits are expanded in both directions along each of the two sequences being compared for as far as the cumulative alignment score can be increased. Extension of the word hits is stopped when: the cumulative alignment score falls off by the quantity X from a maximum achieved value; the cumulative score goes to zero or below; or the end of either sequence is reached. The BLAST algorithm parameters W, T, and X determine the sensitivity and speed of the alignment. The BLAST program uses as defaults a wordlength (W) of 11, the BLOSUM62 scoring matrix (See, Henikoff & Henikoff, *Proc. Natl. Acad. Sci. USA* 89:10915 (1989)) alignments (B) of 50, expectation (E) of 10, M'S, N'-4, and a comparison of both strands.

The BLAST algorithm then performs a statistical analysis of the similarity between two sequences (See e.g., Karlin and Altschul, Proc. Nat'l. Acad. Sci. USA 90:5873-5787 [1993]). One measure of similarity provided by the BLAST algorithm is the smallest sum probability (P(N)), which provides an indication of the probability by which a match between two nucleotide or amino acid sequences would occur by chance. For example, a nucleic acid is considered similar to a serine protease nucleic acid of this invention if the smallest sum probability in a comparison of the test nucleic acid to a serine protease nucleic acid is less than about 0.1, more preferably less than about 0.01, and most preferably less than about 0.001. Where the test nucleic acid encodes a serine protease polypeptide, it is considered similar to a specified serine protease nucleic acid if the comparison results in a smallest sum probability of less than about 0.5, and more preferably less than about 0.2.

The pro region of SEQ ID NO:7 was used to search the NCBI non-redundant protein database (version Mar. 26, 2009). The command line BLAST program (version 2.2.17) was used with default parameters. The obtained sequences that were found to have sequences similar to the pro region (SEQ ID NO:7) were divided into pro regions and mature regions, which were further analyzed as follows to generate the alignments shown in FIGS. 2 and 3.

The alignments of the amino acid sequences of the pro region (FIG. 2) and the mature region (FIG. 3) of various serine proteases to the pro region (SEQ ID NO:7) and mature region of GG36 (SEQ ID NO:9) were obtained using the multiple alignment programs ClustalW and MUSCLE. The alignment was first performed using the program ClustalW (version 1.83) with default parameters. The alignment was refined five times using the program MUSCLE (version 3.51) with default parameters. Only the regions corresponding to the mature region or pro region of were chosen in the alignment. The percent identity was calculated as the number of identical residues aligned between the two sequences in question divided by the number of residues aligned in the alignment. As discussed above, the alignments show that there are several pro and mature sequences that share a high degree of amino acid identity to that of the pro (SEQ ID NO:7) and mature (SEQ ID NO:9) regions of GG36.

In some embodiments, in addition to encoding the pro-protease, the unmodified precursor polynucleotide further comprises a pre polynucleotide encoding a signal peptide, which is operably linked to the pro-protease. In some embodiments, the signal peptide is the AprE signal peptide VRSKKLWISLLFALTLIFTMAFSNMSAQA (SEQ ID NO:3) encoded by the polynucleotide of gtgagaagcaaaaaattgtggatcagcttgttgtttgcgttaacgt-taatctttacgatggcgttcagcaacatgtctgcgcaggct (SEQ ID NO:2). In other embodiments, the signal peptide is a fusion signal peptide VRSKKLWIVASTALLISVAFSSSIASA (SEQ ID NO:5) encoded by the polynucleotide of gtgagaagcaaaaaat-tgtggatcgtcgcgtcgaccgcactact-catttctgttgcttttagttcatcgatcgcatcggct (SEQ ID NO:4). In yet other embodiments, the precursor polynucleotide comprises the polynucleotide that encodes the signal peptide that is naturally and operably linked to the pro-protease. Any signal sequence that can effectuate efficient secretion of a modified protease in a *Bacillus* sp host cell can be operably linked to a pro-protease of the invention. Such signal peptides include signal peptides of bacterial origin that direct secretion of proteins via bacterial secretion pathways e.g. Sec pathway, TAT pathway, and eukaryotic signal sequences that are applicable for expressing proteins in prokaryotic host cells (EP1481059B1).

Modified Polynucleotides Encoding Modified Proteases

The unmodified precursor polynucleotide described above, is modified to encode a modified protease by introducing at least one mutation at any one of amino acids at positions 1-84 of the pro polypeptide of SEQ ID NO:7, which is operably linked to a mature protease. In some embodiments, the at least one mutation is an amino acid substitution.

In some embodiments, the modified polynucleotide encodes an amino acid substitution at least at one amino acid position selected from positions 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, and 84, of the pro polypeptide of SEQ ID NO:7, operably linked to a mature protease that is at least 60% identical to the mature protease of SEQ ID NO:9. In some embodiments, the mature protease is at least about 65%, at least about 70%, at least about 75%, at least about 80%, at least about 85%, at least about 90%, at least about 95%, at least about 97%, at least about 98%, at least about 99% identical to the mature region of SEQ ID NO:9. Mature proteases that are at least 60% identical to the mature protease of SEQ ID NO:9 (*B. lentus* protease GG36), include the wild-type *Bacillus clausii* PB92 protease Maxacal (SEQ ID NO:13), and variants thereof such as SEQ ID NO:11, SEQ ID NO:15, SEQ ID NO:17, SEQ ID NO:19, SEQ ID NO:21, SEQ ID NO:23, and SEQ ID NO:25; and homologs of SEQ ID NO:9 including homologs of mature proteases from *Bacillus* sp. such as P27693_*Bacillus*_alcalophilus e.g. SEQ ID NO:47, P20724_*Bacillus*_sp_YAB e.g. SEQ ID NO:48, BAA25184_*Bacillus*_sp e.g. SEQ ID NO:49, YP_174261_ *B*_*clausii*_KSM-K16 e.g. SEQ ID NO:50, BAA06157 *Bacillus* sp G-825-6 (SEQ ID NO:51) and BAF34115_A_transvaalensis e.g. SEQ ID NO:52, (FIG. 3). Preferably, the modified pro polynucleotide encodes a mutation at least at one amino acid at position chosen from positions 6, 30 and 32 of the pro polypeptide of SEQ ID NO: 7, which is operably linked to the mature protease of any one of the proteases of SEQ ID NOS: 9, 11, 13, 15, 17, 19, 21, 23, and 25. The at least one mutation is an amino acid substitution of the glutamic acid (E) at position 6 and/or 30; and/or the amino acid substitution of the alanine (A) at position 32. It is intended that any of the other 19 amino acids that substitute the glutamic acid (E) at position 6 and/or 30, and/or the alanine (A) at position 32 of the pro region of SEQ ID NO:7 may be used to encode a modified protease from which the mature form is produced at a level that is greater than that obtained from processing of the corresponding unmodified precursor protein. In some embodiments, the at least one mutation is a substitution chosen from the following substitutions:

E6A, E6R, E6C, E6Q, E6H, E6I, E6K, E6L, E6M, E6S, E6Y, E6N, E6G, E6F, E6P, E6T, E6W, E6V, E30A, E30R, E30N, E30D, E30G, E30H, E30L, E30K, E30F, E30S, E30T, E30V, E30R, E30Q, E30G, E30I, E30L, E30M, E30F, E30P, E30T, E30W, E30Y, E30C, E30M, E30F E30V, A32K, A32T, A32Q, A32S, A32V, A32L, and A32F of the pro polypeptide of the SEQ ID NO:7. For example, any one of the substitutions chosen from E6A, E6R, E6C, E6Q, E6H, E6I, E6K, E6M, E6S, E6Y, E30A, E30R, E30N, E30D, E30Q, E30G, E30L, E30M, E30P, E30S, E30T, E30W, E30Y, E30V, A32, A32R, A32C, A32E, A32G, A32L, A32K, A32F, A32T, A32Y, and A32V are made in the pro region of SEQ ID NO:7 to produce the mature protease of SEQ ID NO:17; any one of the substitutions chosen from E6A, E6R, E6N, E6C, E6Q, E6G, E6H, E6M, E6F, E6P, E6S, E6T, E6W, E6V, A32K, A32T, and A32V, are made in the pro region of SEQ ID NO:7 to produce the mature protease of SEQ ID NO:9; any one of the substitutions chosen from E6A, E6H, E6K, and E6R, E30A, E30R, E30N, E30D, E30G, E30H, E30L, E30K, E30F, E30S, E30T, and E30V, are made in the pro region of SEQ ID NO:7 to produce the mature protease of SEQ ID NO:19; any one of the substitutions chosen from E6A, E6R, E6Q, E6G, E6L, E6K, E6M, E6F, E6T, E6V, E30R, E30Q, E30G, E30I, E30L, E30M, E30F, E30P, E30T, E30W, E30Y, E30V, A32Q, A32S, A32T, and A32V, are made in the pro region of SEQ ID NO:7 to produce the mature protease of SEQ ID NO:11; and any one of the substitutions chosen from E30A, E30R, E30N, E30D, E30C, E30G, E30H, E30M, E30F, E30S, E30W, A32L, A32F, and A32V, are made in the pro region of SEQ ID NO:7 to produce the mature protease of SEQ ID NO:21. The at least one substitution enhances the production of the mature protease when compared to the production of the mature protease expressed from a precursor protease that does not comprise the at least one substitution in the pro region of SEQ ID NO:7 to which it is operably linked.

In some other embodiments, the modification of the pro region of SEQ ID NO:7 includes a combination of mutations. For example, modification of the pro region of SEQ ID NO:7 includes a combination of at least two substitutions. In other embodiments, modification of the pro region of SEQ ID NO:7 includes a combination of at least three, at least four, at least five, at least six, at least seven, at least 8, at least nine, or at least 10 substitutions. Modifications of the pro region also include a combination of at least one substitution and one deletion; a combination of at least one substitution and at least one insertion; a combination of at least one insertion and one deletion, and a combination of at least one substitution, at least one deletion, and at least one insertion. Preferably, the modification of the pro region of SEQ ID NO:7 includes at least two substitutions that result in a combination of substitutions at positions 6 and 30 (i.e. E6X-E30X), 6 and 32 (i.e. E6X-A32X) or 30 and 32 (i.e. E30X-A32X). For example, the modified polynucleotide encodes a pro region comprising a combination of substitutions chosen from E6R-A32K, E6N-A32K, E6D-A32K, E6I-A32K, E6K-A32K, E6M-A32K, E6P-A32K, E6S-A32K, E6T-A32K, E6N-A32K, E30W-A32K, E30V-A32K, E6A-E30G, E6R-E30G, E6C-E30G, E6Q-E30G, E6G-E30G, E6H-E30G, E6K-E30G, E6S-E30G, E6W-E30G, E30G-A32R, E30G-A32Q, E30G-A32E, E30G-A32G, E30G-A32H, E30G-A32I, E30G-A32K, E30G-A32S, E30G-A32T, E30G-A32W, E30G-A32V, E6G-E30G-A32E, E6G-E30G-A32S, E6G-E30G-A32T, E6G-E30G-A32W, E6A-E30G, E6R-E30G, E6N-E30G, E6D-E30G, E6C-E30G, E6Q-E30G, E6G-E30G, E6H-E30G, E6K-E30G, E6M-E30G, E6F-E30G, E6P-E30G, E6S-E30G, E6T-E30G, E6W-E30G, E6V-E30G, E6Y-E30G, E6A-E30S, E6G-E30S, E6L-E30S, E6K-E30S, E6F-E30S, E6P-E30S, E6Y-E30S, E6V-E30S, E30S-A32R, E30S-A32N, E30S-A32D, E30S-A32C, E30S-A32Q, E30S-A32E, E30S-A32G, E30S-A32H, E30S-A32L, E30S-A32K, E30S-A32M, E30S-A32F, E30S-A32P, E30S-A32S, E30S-A32T, E30S-A32W, E30S-A32Y, and E30S-A32V. For example, modification of the pro region of SEQ ID NO:7 includes a combination of at least two substitutions chosen from E6R-A32K, E6N-A32K, E6D-A32K, E6I-A32K, E6K-A32K, E6M-A32K, E6P-A32K, E6S-A32K, E6T-A32K, E6N-A32K, E30W-A32K, and E30V-A32K to produce the mature protease of SEQ ID NO:9; modification of the pro region of SEQ ID NO:7 includes a combination of at least two substitutions chosen from E6A-E30G, E6R-E30G, E6C-E30G, E6Q-E30G, E6G-E30G, E6H-E30G, E6K-E30G, E6S-E30G, E6W-E30G, E30G-A32R, E30G-A32Q, E30G-A32E, E30G-A32G, E30G-A32H, E30G-A32I, E30G-A32K, E30G-A32S, E30G-A32T, E30G-A32W, E30G-A32V to produce the mature protease of SEQ ID NO:17; modification of the pro region of SEQ ID NO:7 includes a combination of at least two substitutions chosen from E6A-E30G, E6R-E30G, E6N-E30G, E6D-E30G, E6C-E30G, E6Q-E30G, E6G-E30G, E6H-E30G, E6K-E30G, E6M-E30G, E6F-E30G, E6P-E30G, E6S-E30G, E6T-E30G, E6W-E30G, E6V-E30G, E6Y-E30G to produce the mature protease of SEQ ID NO:19; and modification of the pro region of SEQ ID NO:7 includes a combination of at least two substitutions chosen from E6A-E30S, E6G-E30S, E6L-E30S, E6K-E30S, E6F-E30S, E6P-E30S, E6Y-E30S, E6V-E30S, E30S-A32R, E30S-A32N, E30S-A32D, E30S-A32C, E30S-A32Q, E30S-A32E, E30S-A32G, E30S-A32H, E30S-A32L, E30S-A32K, E30S-A32M, E30S-A32F, E30S-A32P, E30S-A32S, E30S-A32T, E30S-A32W, E30S-A32Y, and E30S-A32V to produce the mature protease of SEQ ID NO:21. Other examples of modifications of the pro region of SEQ ID NO:7 include at least three substitutions that result in a combination of substitutions at positions 6, 30 and 32 (i.e. E6X-E30X-A32X). For example, modification of the pro region of SEQ ID NO:7 includes a combination of at least three substitutions chosen from E6G-E30G-A32E, E6G-E30G-A32S, E6G-E30G-A32T, E6G-E30G-A32W to produce the mature protease of SEQ ID NO:17. The at least two or three substitutions enhance the production of the mature protease when compared to the production of the mature protease expressed from a precursor protease that does not comprise the at least two or three substitutions in the pro region of SEQ ID NO:7 to which it is operably linked.

Several methods are known in the art that are suitable for generating modified polynucleotide sequences of the present invention, including but not limited to site-saturation mutagenesis, scanning mutagenesis, insertional mutagenesis, deletion mutagenesis, random mutagenesis, site-directed mutagenesis, and directed-evolution, as well as various other recombinatorial approaches. The commonly used methods include DNA shuffling (Stemmer W P, Proc Natl Acad Sci USA. 25; 91(22):10747-51 [1994]), methods based on non-homologous recombination of genes e.g. ITCHY (Ostermeier et al., Bioorg Med. Chem. 7(10):2139-44 [1999]), SCRACHY (Lutz et al. Proc Natl Acad Sci USA. 98(20): 11248-53 [2001]), SHIPREC (Sieber et al., Nat. Biotechnol. 19(5):456-60 [2001]), and NRR (Bittker et al., Nat. Biotechnol. 20(10):1024-9 [2001]; Bittker et al., Proc Natl Acad Sci USA. 101(18):7011-6 [2004]), and methods that rely on the use of oligonucleotides to insert random and targeted mutations, deletions and/or insertions (Ness et al., Nat. Biotechnol. 20(12):1251-5 [2002]; Coco et al., Nat. Biotechnol. 20(12): 1246-50 [2002]; Zha et al., Chembiochem. 3; 4(1):34-9 [2003], Glaser et al., J. Immunol. 149(12):3903-13 [1992], Sondek and Shortie, Proc Natl Acad Sci USA 89(8):3581-5 [1992], Yáñez et al., Nucleic Acids Res. 32(20):e158 [2004], Osuna et al., Nucleic Acids Res. 32(17):e136 [2004], Gaytán et al., Nucleic Acids Res. 29(3):E9 [2001], and Gaytán et al., Nucleic Acids Res. 30(16):e84 [2002]).

In addition to encoding the modified pro-protease, the modified precursor polynucleotide further comprises a pre polynucleotide encoding a signal peptide. In some embodiments, the signal peptide is the AprE signal peptide (SEQ ID NO:3) encoded by the polynucleotide of SEQ ID NO:2. For example, full-length modified precursor proteases include the proteases of SEQ ID NOS:, wherein the pro region of said precursor proteases comprises at least one mutation. In some embodiments, the at least one mutation is an amino acid substitution is made at the position equivalent to position 6, 30 or 32 of the pro region of SEQ ID NO:7. Alternatively, the signal peptide is a fusion signal peptide of SEQ ID NO:5 encoded by the polynucleotide of SEQ ID NO:4. Signal peptides that are naturally linked to the mature protease may also be used to express the full-length modified proteases described herein. Examples of full-length precursor proteases that can be modified to comprise at least one amino acid substitution at a position chosen from 6, 30 and 32 of the pro region of SEQ ID NO:7 include:

the full-length protease of SEQ ID NO:59 VRSKKLWISLLFALTLIFTMAFSNMSAQA AEEAKEKYLIGFNEQEAVSEFVEQVEANDEVAILSEE EEVEIELLHEFETIPVLSVELSPEDVDALELDPAISYIE EDAEVTTMAQSVPWGISRVQA PAAHNRGLTGS-GVKVAVLDTGISTHPDLNIRGGAS-FVPGEPSTQDGNGHGTHVAGTIAALN NSIGVLGVAP-SAELYAVKVLGASGSGSVSSIAQGLEWAGNNGMHVA NLSLGSPSPSATLEQ AVNSATSRGVLVVAASGNS-GAGSISYPARYANAMAVGATDQNNNRAS-FSQYGAGLDIVAP GVNVQSTYPGSTYASLNGTSMAT-PHVAGAAALVKQKNPSWSNVQIRNHLKNTATSLGSTN LYGSGLVNAEAATR; SEQ ID NO:59);

the full-length protease of SEQ ID NO:60 VRSKKLWISLLFALTLIFTMAFSNMSAQA AEEAKEKYLIGFNEQEAVSEFVEQVEANDEVAILSEE EEVEIELLHEFETIPVLSVELSPEDVDALELDPAISYIE EDAEVTTMAQSVPWGISRVQA PAAHNRGLTGS-GVKVAVLDTGISTHPDLNIRGGAS-FVPGEPSTQDGNGHGTHVAGTIAALD NSIGVLGVAP-SAELYAVKVLGASGSGAISSIAQGLEWAGNNGMHVA NLSLGSPSPSATLEQ AVNSATSRGVLVVAASGNS-GAGSISYPARYANAMAVGATDQNNNRAS-FSQYGAGLDIVAP GVNVQSTYPGSTYASLNGTSMAT-PHVAGAAALVKQKNPSWSNVQIRNHLKNTATSLGST NLYGSGLVNAEAATR; SEQ ID NO:60);

the full-length protease of SEQ ID NO:61 VRSKKLWISLLFALTLIFTMAFSNMSAQA AEEAKEKYLIGFNEQEAVSEFVEQVEANDEVAILSEE EEVEIELLHEFETIPVLSVELSPEDVDALELDPAISYIE EDAEVTTMAQSVPWGISRVQA PAAHNRGLTGS-GVKVAVLDTGISTHPDLNIRGGAS-FVPGEPSTQDGNGHGTHVAGTIAALN NSIGVLGVAP-NAELYAVKVLGASGSGSVSSIAQGLEWAGNNGMHVA NLSLGSPSPSATLE QAVNSATSRGVLVVAASGNS-GAGSISYPARYANAMAVGATDQNNNRAS-FSQYGAGLDIVA PGVNVQSTYPGSTYASLNGTSMAT-PHVAGAAALVKQKNPSWSNVQIRNHLKNTATSLGST NLYGSGLVNAEAATR; SEQ ID NO:61);

the full-length protease of SEQ ID NO:62 VRSKKLWISLLFALTLIFTMAFSNMSAQA AEEAKEKYLIGFNEQEAVSEFVEQVEANDEVAILSEE EEVEIELLHEFETIPVLSVELSPEDVDALELDPAISYIE EDAEVTTMAQSVPWGISRVQA PAAHNRGLTGS-GVKVAVLDTGISTHPDLNIRGGAS-FVPGEPSTQDGNGHGTHVAGTIAALN NSIGVLGVAP-NAELYAVKVLGASGSGSVSSIAQGLEWAGNNVMHVA NLSLGLQAPSATLEQ AVNSATSRGVLVVAASGNS-GAGSISYPARYANAMAVGATDQNNNRAS-FSQYGAGLDIVAP GVNVQSTYPGSTYASLNGTSMAT-PHVAGAAALVKQKNPSWSNVQIRNHLKNTATSLGSTN LYGSGLVNAEAATR; SEQ ID NO:62);

the full-length protease of SEQ ID NO:63 VRSKKLWISLLFALTLIFTMAFSNMSAQA AEEAKEKYLGFNEQEAVSEFVEQVEANDEVAILSEEE EVEIELLHEFETIPVLSVELSPEDVDALELDPAISYIEE DAEVTTMAQSVPWGISRVQA PAAHNRGLTGS-GVKVAVLDTGISTHPDLNIRGGAS-FVPGEPSTQDGNGHGTHVAGTIAALN NSIGVLGVAP-NAELYAVKVLGASGMGSVSSIAQGLEWAGNNVMHV ANLSLGLQAPSATLE QAVNSATSRGVLVVAASGNS-GAGSISYPARYANAMAVGATDQNNNRAS-FSQYGAGLDIVA PGVNVQSTYPGSTYASLNGTSMAT-PHVAGAAALVKQKNPSWSNVQIRNHLKNTATSLGST NLYGSGLVNAEAATR; SEQ ID NO:63);

the full-length protease of SEQ ID NO:64 VRSKKLWISLLFALTLIFTMAFSNMSAQA

AEEAKEKYLIGFNEQEAVSEFVEQVEANDEVAILSEE
EEVEIELLHEFETIPVLSVELSPEDVDALELDPAISYIE
EDAEVTTMAQSVPWGISRVQA PAAHNRGLTGS-
GVKVAVLDTGISTHPDLNIRGGAS-
FVPGEPSTQDGNGHGTHVAGTIAALN NSIGVLGVAP-
NAELYAVKVLGASGGGSNSSIAQGLEWAGNNGMHV
ANLSLGSPSPSATLE QAVNSATSRGVLVVAASGNS-
GAGSISYPARYANAMAVGATDQNNNRAS-
FSQYGAGLDIVA PGVNVQSTYPGSTYASLNGTSMAT-
PHVAGAAALVKQKNPSWSNVQIRNHLKNTATSLGST
NLYGSGLVNAEAATR; SEQ ID NO:64);
the full-length protease of SEQ ID NO:65 VRSKKLWISLL-
FALTLIFTMAFSNMSAQA
AEEAKEKYLIGFNEQEAVSEFVEQVEANDEVAILSEE
EEVEIELLHEFETIPVLSVELSPEDVDALELDPAISYIE
EDAEVTTMAQSVPWGISRVQA PAAHNRGLTGS-
GVKVAVLDTGISTHPDLNIRGGAS-
FVPGEPSTQDGNGHGTHVAGTIAALD NSIGV-
LGVAPRAELYAVKVLGASGSGSVSSIAQGLEWAGNN
RMHVANLSLGLQAPSATLEQ AVNSATSRGVLVVAAS-
GNSGAGSISYPARYANAMAVGAT-
DQNNNRASFSQYGAGLDIVAP GVNVQSTYPGST-
YASLNGTSMATPHVAGAAALVKQKNPSWSNVQIRN
HLKNTATSLGSTN LYGSGLVNAEAATR; SEQ ID
NO:65),
the full-length protease of SEQ ID NO:66 VRSKKLWISLL-
FALTLIFTMAFSNMSAQA
AEEAKEKYLIGFNEQEAVSEFVEQVEANDEVAILSEE
EEVEIELLHEFETIPVLSVELSPEDVDALELDPAISYIE
EDAEVTTMAQSVPWGISRVQA PAAHNRGLTGS-
GVKVAVLDTGISTHPDLNIRGGAS-
FVPGEPSTQDGNGHGTHVAGTIAALD NSIGV-
LGVAPRAELYAVKVLGASGSGSVSSIAQGLEWAGNN
RMHVANLSLGLQAPSATLEQ AVNSATSRGVLVVAAS-
GNSGAGSISYPARYANAMAVGAT-
DQNNNRADFSQYGAGLDIVAP GVNVQSTYPGST-
YASLNGTSMATPHVAGAAALVKQKNPSWSNRQIRN
HLKNTATSLGSTN LYGSGLVNAEAAT; SEQ ID NO:66),
and
the full-length protease of SEQ ID NO:67 VRSKKLWISLL-
FALTLIFTMAFSNMSAQA
AEEAKEKYLIGFNEQEAVSEFVEQVEANDEVAILSEE
EEVEIELLHEFETIPVLSVELSPEDVDALELDPAISYIE
EDAEVTTMAQSVPWGISRVQA PAAHNRGLTGS-
GVKVAVLDTGISTHPDLNIRGGAS-
FVPGEPSTQDGNGHGTHVAGTIAALD NSIGV-
LGVAPRAELYAVKVLGASGSGSVSSIAQGLEWAGNN
GMHVANLSLGLQAPSATLE QAVNSATSRGVLVVAAS-
GNSGAGSISYPARYANAMAVGAT-
DQNNNRADFSQYGAGLDIVA PGVNVQSTYPGST-
YASLNGTSMATPHVAGAAALVKQKNPSWSNVQIRR
HLKNTATSLGST NLYGSGLVNAEAATR; SEQ ID
NO:67).

The pre region (signal peptide; SEQ ID NO:3) is shown in bold, the pro region (SEQ ID NO:7) is underlined, and the mature region is italicized.

As previously described, in addition to being identical to the naturally-occurring pro region of the P41362 *B. clausii* and P27693 *Bacillus alkalophilus* (FIG. 2), the pro region of SEQ ID NO:7 has a high degree of identity with the amino acid sequence of the pro region of proteases from as GG36 *B. lentus* 267048, (SEQ ID NO:53), P20724_*Bacillus*_sp_YAB SEQ ID NO:54), BAA25184_*Bacillus*_sp (SEQ ID NO:55), YP_174261_*B*_*clausii*_KSM-K16 e.g. SEQ ID NO:56, BAA06157 *Bacillus* sp G-825-6 (SEQ ID NO:57) and BAF34115_A_*transvaalensis* e.g. SEQ ID NO:58, (FIG. 2).

It is expected that mutations made in the pro region of SEQ ID NOs:53-58 and corresponding to the mutations of SEQ ID NO:7 that enhance the production of the mature protease to which it is operably linked, will enhance the production of the mature protease to which the modified pro region of SEQ ID NOs: 53-58 is operably linked. For example, any one of the modified polynucleotides that encode the pro region of SEQ ID NOs: 53-58 can be modified to encode an amino acid substitution at least at one amino acid position selected from positions 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, and 84, wherein the position is numbered by correspondence with the amino acid sequence of the pro polypeptide of SEQ ID NO:7. Preferably, any one of the modified polynucleotides that encode the pro region of SEQ ID NOs: 53-58 is modified to encode a mutation at least at one amino acid at position chosen from positions 6, 30 and 32. In some embodiments, the at least one mutation chosen from positions 6, 30 and 32 is a substitution chosen from the following substitutions: E6A, E6R, E6C, E6Q, E6H, E6I, E6K, E6L, E6M, E6S, E6Y, E6N, E6G, E6F, E6P, E6T, E6W, E6V, E30A, E30R, E30N, E30D, E30G, E30H, E30L, E30K, E30F, E30S, E30T, E30V, E30R, E30Q, E30G, E30I, E30L, E30M, E30F, E30P, E30T, E30W, E30Y, E30C, E30M, E30F E30V, A32K, A32T, A32Q, A32S, A32V, A32 L, and A32F, wherein the positions are numbered by correspondence with the amino acid sequence of the pro polypeptide of the SEQ ID NO:7. In other embodiments, the modified polynucleotide encodes a pro region comprising a combination of substitutions chosen from a combination of substitutions made at positions 6 and 32 (i.e. E6X-E30X), at positions 30 and 32 (i.e. E30X-A32X). For example, the modified polynucleotide encodes a pro region comprising a combination of substitutions chosen from E6R-A32K, E6N-A32K, E6D-A32K, E6I-A32K, E6K-A32K, E6M-A32K, E6P-A32K, E6S-A32K, E6T-A32K, E6N-A32K, E30W-A32K, E30V-A32K, E6A-E30G, E6R-E30G, E6C-E30G, E6Q-E30G, E6G-E30G, E6H-E30G, E6K-E30G, E6S-E30G, E6W-E30G, E30G-A32R, E30G-A32Q, E30G-A32E, E30G-A32G, E30G-A32H, E30G-A32I, E30G-A32K, E30G-A32S, E30G-A32T, E30G-A32W, E30G-A32V, E6G-E30G-A32E, E6G-E30G-A32S, E6G-E30G-A32T, E6G-E30G-A32W, E6A-E30G, E6R-E30G, E6N-E30G, E6D-E30G, E6C-E30G, E6Q-E30G, E6G-E30G, E6H-E30G, E6K-E30G, E6M-E30G, E6F-E30G, E6P-E30G, E6S-E30G, E6T-E30G, E6W-E30G, E6V-E30G, E6Y-E30G, E6A-E30S, E6G-E30S, E6L-E30S, E6K-E30S, E6F-E30S, E6P-E30S, E6Y-E30S, E6V-E30S, E30S-A32R, E30S-A32N, E30S-A32D, E30S-A32C, E30S-A32Q, E30S-A32E, E30S-A32G, E30S-A32H, E30S-A32L, E30S-A32K, E30S-A32M, E30S-A32F, E30S-A32P, E30S-A32S, E30S-A32T, E30S-A32W, E30S-A32Y, and E30S-A32V, wherein the positions are numbered by correspondence with the amino acid sequence of the pro polypeptide of the SEQ ID NO:7. In yet other embodiments, the modified polynucleotide encodes a pro region comprising a combination of substitutions chosen from E6G-E30G-A32E, E6G-E30G-A32S, E6G-E30G-A32T, E6G-E30G-A32W, wherein the positions are numbered by correspondence with the amino acid sequence of the pro polypeptide of the SEQ ID NO:7. Any one of the pro regions of SEQ ID NOS:7 and 53-58 that is modified to contain the at least one two or three substitutions as described above, is operably linked to a mature protease that is at least 60% identical to the mature protease of SEQ ID NO:9. Mature proteases that are at least 60% identical to the mature protease of SEQ ID NO:9 (*B. lentus* protease GG36), include the wild-type *Bacillus clausii* PB92 protease Maxacal (SEQ ID NO:13), and variants thereof such as SEQ ID NO:11, SEQ ID NO:15, SEQ ID NO:17, SEQ ID NO:19, SEQ ID NO:21, SEQ ID NO:23, and SEQ ID NO:25; and homologs of SEQ ID NO:9 including homologs of mature proteases from *Bacillus* sp. such as P27693_*Bacillus*_alcalophilus e.g. SEQ ID NO:47, P20724_*Bacillus*_sp_YAB e.g. SEQ ID NO:48, BAA25184_*Bacillus*_sp e.g. SEQ ID NO:49, YP_174261_*B*_clausii_KSM-K16 e.g. SEQ ID NO:50, BAA06157 *Bacillus* sp G-825-6 (SEQ ID NO:51) and BAF34115_A_transvaalensis e.g. SEQ ID NO:52, (FIG. 3).

Any one of the pro regions of SEQ ID NOS: 7 and 53-58 that is modified to contain the at least one substitution described above, and that is operably linked to a mature protease that is at least 60% identical to the mature protease of SEQ ID NO:9, is further operably linked to a signal peptide. Preferably, the signal peptide is the AprE signal peptide (SEQ ID NO:3) encoded by the polynucleotide of SEQ ID NO:2. Alternatively, the signal peptide is a fusion signal peptide VRSKKLWIVASTALLISVAFSSSIASA (SEQ ID NO:5) encoded by the polynucleotide of SEQ ID NO:4 gtgagaagcaaaaaattgtggatcgtcgcgtcgac-cgcactactcatttctgttgcttttagttcatcgatcgcatcggct (SEQ ID NO:4). Any signal sequence that can effectuate efficient secretion of a modified protease in a *Bacillus* sp host cell can be operably linked to a pro-protease of the invention. Such signal peptides include signal peptides of bacterial origin that direct secretion of proteins via bacterial secretion pathways e.g. Sec pathway, TAT pathway, and eukaryotic signal sequences that are applicable for expressing proteins in prokaryotic host cells (EP1481059B1).

The at least one amino acid substitution at position 6, 30, and/or 32 made in the pro region of SEQ ID NO:7 can be introduced at equivalent amino acid positions in the pro regions of a pre-pro-protease to enhance the production of the mature enzyme, wherein the signal peptide can be chosen from the signal peptides of SEQ ID NOS: 3, and 5, signal peptides that are naturally and operably linked to the pro-protease, and any signal sequence that can effectuate efficient secretion of a modified protease in a *Bacillus* sp host cell e.g. *Bacillus subtilis*.

As indicated above, in some embodiments, the present invention provides vectors comprising the aforementioned modified polynucleotides. In some embodiments, the vector is an expression vector in which the modified polynucleotide sequence encoding the modified protease of the invention is operably linked to additional segments required for efficient gene expression (e.g., a promoter operably linked to the gene of interest). In some embodiments, these necessary elements are supplied as the gene's own homologous promoter if it is recognized, (i.e., transcribed by the host), and a transcription terminator that is exogenous or is supplied by the endogenous terminator region of the protease gene. In some embodiments, a selection gene such as an antibiotic resistance gene that enables continuous cultural maintenance of plasmid-infected host cells by growth in antimicrobial-containing media is also included.

In some embodiments, the expression vector is derived from plasmid or viral DNA, or in alternative embodiments, contains elements of both. Exemplary vectors include, but are not limited to pXX, pC194, pJH101, pE194, pHP13 (Harwood and Cutting (eds), *Molecular Biological Methods for Bacillus*, John Wiley & Sons, [1990], in particular, chapter 3; suitable replicating plasmids for *B. subtilis* include those listed on page 92; Perego, M. (1993) Integrational Vectors for Genetic Manipulations in *Bacillus subtilis*, p. 615-624; A. L. Sonenshein, J. A. Hoch, and R. Losick (ed.), *Bacillus subtilis* and other Gram-positive bacteria: biochemistry, physiology and molecular genetics, American Society for Microbiology, Washington, D.C.).

Figure 4A:
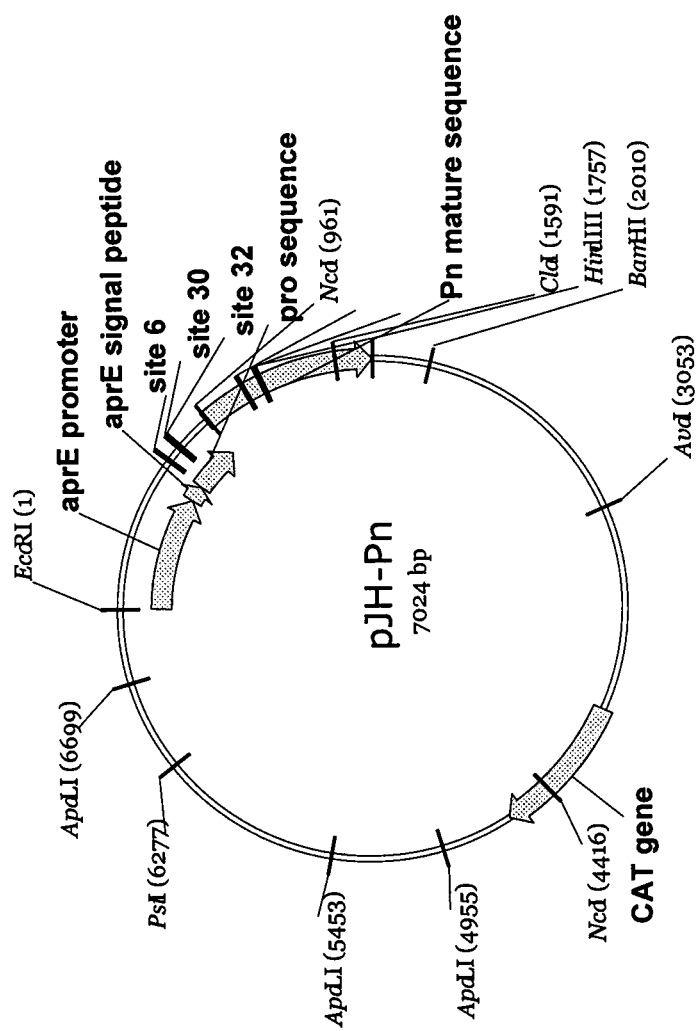
FIG. 4 provides the map of the pJH-Pn plasmid (A) and the map of the pBN3-Pn (B) vector comprising the aprE signal sequence (SEQ ID NO:3), the pro sequence of SEQ ID NO:7 and the polynucleotide encoding the mature serine protease Pn.
Figure 4B:
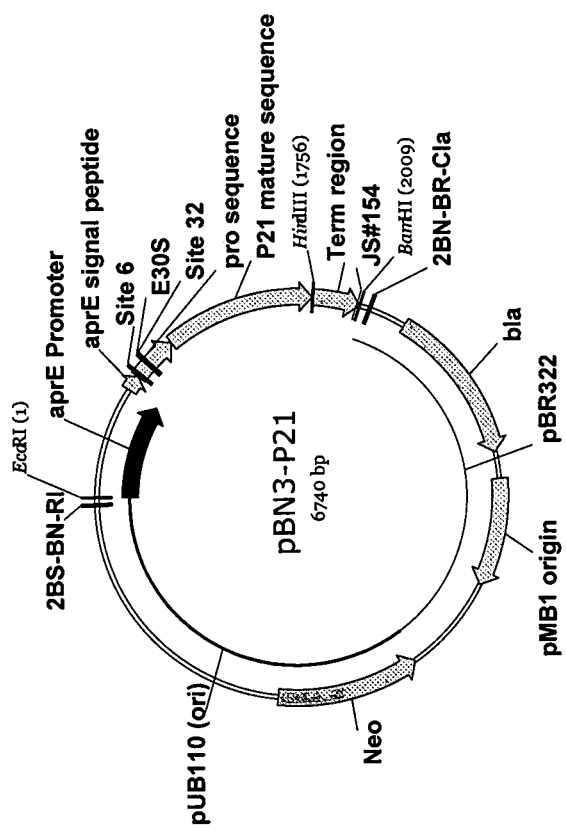

For expression and production of protein(s) of interest e.g. a protease, in a cell, at least one expression vector comprising at least one copy of a polynucleotide encoding the modified protease, and preferably comprising multiple copies, is transformed into the cell under conditions suitable for expression of the protease. In some particularly embodiments, the sequences encoding the proteases (as well as other sequences included in the vector) are integrated into the genome of the host cell, while in other embodiments, the plasmids remain as autonomous extra-chromosomal elements within the cell. Thus, the present invention provides both extrachromosomal elements as well as incoming sequences that are integrated into the host cell genome. It is intended that each of the vectors described herein will find use in the present invention. In some embodiments, the polynucleotide construct encoding the modified protease is present on an integrating vector (e.g., pJH-GG36; FIG. 4) that enables the integration and optionally the amplification of the modified polynucleotide into the bacterial chromosome. Examples of sites for integration include, but are not limited to the aprE, the amyE, the veg or the pps regions. Indeed, it is contemplated that other sites known to those skilled in the art will find use in the present invention. In some embodiments, transcription of the polynucleotides encoding the modified proteases is effectuated by a promoter that is the wild-type promoter for the selected precursor protease. In some other embodiments, the promoter is heterologous to the precursor protease, but is functional in the host cell. Specifically, examples of suitable promoters for use in bacterial host cells include but are not limited to the amyE, amyQ, amyL, pstS, sacB, pSPAC, pAprE, pVeg, pHpaII promoters, the promoter of the *B. stearothermophilus* maltogenic amylase gene, the *B. amyloliquefaciens* (BAN) amylase gene, the *B. subtilis* alkaline protease gene, the *B. clausii* alkaline protease gene the *B. pumilis* xylosidase gene, the *B. thuringiensis* cryIIIA, and the *B. licheniformis* alpha-amylase gene. In some embodiments, the promoter is the AprE promoter having the sequence:

(SEQ ID NO: 1)

```
gaattcctccatttcttctgctatcaaaataacagactcgtgattttccaaacgagctttcaaaaaagcctctgcccttgcaaatcg gatgcctgtctataaaattcccgatattggttaaacagcggcgcaatggcggccgcatctgatgtctttgcttggcgaatgttcatctt atttcttcctccctctcaataatttttttcattctatccttttctgtaaagtttatttttcagaatactttatcatcatgctttgaaaaaatatcac gataatatccattgttctcacggaagcacacgcaggtcatttgaacgaatttttcgacaggaatttgccgggactcaggagcattta acctaaaaagcatgacatttcagcataatgaacatttactcatgtctattttcgttcttttctgtatgaaaatagttatttcgagtctctac
```

-continued

```
ggaaatagcgagagatgatatacctaaatagagataaaatcatctcaaaaaaatgggtctactaaaatattattccatctattaca
ataaattcacagaatagtcttttaagtaagtctactctgaatttttttaaaaggagagggtaaaga.
```

Additional promoters include, but are not limited to the A4 promoter, as well as phage Lambda $P_R$ or $P_L$ promoters, and the *E. coli* lac, trp or tac promoters.

Precursor and modified proteases are produced in host cells of any suitable Gram-positive microorganism, including bacteria and fungi. For example, in some embodiments, the modified protease is produced in host cells of fungal and/or bacterial origin. In some embodiments, the host cells are *Bacillus* sp., *Streptomyces* sp., *Escherichia* sp. or *Aspergillus* sp. In some embodiments, the modified proteases are produced by *Bacillus* sp. host cells. Examples of *Bacillus* sp. host cells that find use in the production of the modified proteins of the present invention include, but are not limited to *B. licheniformis, B. lentus, B. subtilis, B. amyloliquefaciens, B. lentus, B. brevis, B. stearothermophilus, B. alkalophilus, B. coagulans, B. circulans, B. pumilis, B. thuringiensis, B. clausii*, and *B. megaterium*, as well as other organisms within the genus *Bacillus*. In some embodiments, *B. subtilis* host cells find use. U.S. Pat. Nos. 5,264,366 and 4,760,025 (RE 34,606) describe various *Bacillus* host strains that find use in the present invention, although other suitable strains find use in the present invention.

Several industrial strains that find use in the present invention include non-recombinant (i.e., wild-type) *Bacillus* sp. strains, as well as variants of naturally occurring strains and/or recombinant strains. In some embodiments, the host strain is a recombinant strain, wherein a polynucleotide encoding a polypeptide of interest has been introduced into the host. In some embodiments, the host strain is a *B. subtilis* host strain and particularly a recombinant *Bacillus subtilis* host strain. Numerous *B. subtilis* strains are known, including but not limited to 1A6 (ATCC 39085), 168 (1A01), SB19, W23, Ts85, B637, PB1753 through PB1758, PB3360, JH642, 1A243 (ATCC 39,087), ATCC 21332, ATCC 6051, MI113, DE100 (ATCC 39,094), GX4931, PBT 110, and PEP 211 strain (See e.g., Hoch et al., Genetics, 73:215-228 [1973]) (See also, U.S. Pat. No. 4,450,235; U.S. Pat. No. 4,302,544; and EP 0134048; each of which is incorporated by reference in its entirety). The use of *B. subtilis* as an expression host well known in the art (See e.g., See, Palva et al., Gene 19:81-87 [1982]; Fahnestock and Fischer, J. Bacteriol., 165:796-804 [1986]; and Wang et al., Gene 69:39-47 [1988]).

In some embodiments, the *Bacillus* host is a *Bacillus* sp. that includes a mutation or deletion in at least one of the following genes, degU, degS, degR and degQ. Preferably the mutation is in a degU gene, and more preferably the mutation is degU(Hy)32. (See e.g., Msadek et al., J. Bacteriol., 172: 824-834 [1990]; and Olmos et al., Mol. Gen. Genet., 253: 562-567 [1997]). A preferred host strain is a *Bacillus subtilis* carrying a degU32(Hy) mutation. In some further embodiments, the *Bacillus* host comprises a mutation or deletion in scoC4, (See, e.g., Caldwell et al., J. Bacteriol., 183:7329-7340 [2001]); spoIIE (See, Arigoni et al., Mol. Microbiol., 31:1407-1415 [1999]); and/or oppA or other genes of the opp operon (See e.g., Perego et al., Mol. Microbiol., 5:173-185 [1991]). Indeed, it is contemplated that any mutation in the opp operon that causes the same phenotype as a mutation in the oppA gene will find use in some embodiments of the altered *Bacillus* strain of the present invention. In some embodiments, these mutations occur alone, while in other embodiments, combinations of mutations are present. In some embodiments, an altered *Bacillus* that can be used to produce the modified proteases of the invention is a *Bacillus* host strain that already includes a mutation in one or more of the above-mentioned genes. In addition, *Bacillus* sp. host cells that comprise mutation(s) and/or deletions of endogenous protease genes find use. In some embodiments, the *Bacillus* host cell comprises a deletion of the aprE and the nprE genes. In other embodiments, the *Bacillus* sp. host cell comprises a deletion of 5 protease genes (US20050202535), while in other embodiments, the *Bacillus* sp. host cell comprises a deletion of 9 protease genes (US20050202535).

Host cells are transformed with modified polynucleotides encoding the modified proteases of the present invention using any suitable method known in the art. Whether the modified polynucleotide is incorporated into a vector or is used without the presence of plasmid DNA, it is introduced into a microorganism, in some embodiments, preferably an *E. coli* cell or a competent *Bacillus* cell. Methods for introducing DNA into *Bacillus* cells involving plasmid constructs and transformation of plasmids into *E. coli* are well known. In some embodiments, the plasmids are subsequently isolated from *E. coli* and transformed into *Bacillus*. However, it is not essential to use intervening microorganisms such as *E. coli*, and in some embodiments, a DNA construct or vector is directly introduced into a *Bacillus* host.

Those of skill in the art are well aware of suitable methods for introducing polynucleotide sequences into *Bacillus* cells (See e.g., Ferrari et al., "Genetics," in Harwood et al. (ed.), *Bacillus*, Plenum Publishing Corp. [1989], pages 57-72; Saunders et al., J. Bacteriol., 157:718-726 [1984]; Hoch et al., J. Bacteriol., 93:1925-1937 [1967]; Mann et al., Current Microbiol., 13:131-135 [1986]; and Holubova, Folia Microbiol., 30:97 [1985]; Chang et al., Mol. Gen. Genet., 168:11-115 [1979]; Vorobjeva et al., FEMS Microbiol. Lett., 7:261-263 [1980]; Smith et al., Appl. Env. Microbiol., 51:634 [1986]; Fisher et al., Arch. Microbiol., 139:213-217 [1981]; and McDonald, J. Gen. Microbiol., 130:203 [1984]). Indeed, such methods as transformation, including protoplast transformation and congression, transduction, and protoplast fusion are known and suited for use in the present invention. Methods of transformation are used to introduce a DNA construct provided by the present invention into a host cell. Methods known in the art to transform *Bacillus*, include such methods as plasmid marker rescue transformation, which involves the uptake of a donor plasmid by competent cells carrying a partially homologous resident plasmid (Contente et al., Plasmid 2:555-571 [1979]; Haima et al., Mol. Gen. Genet., 223:185-191 [1990]; Weinrauch et al., J. Bacteriol., 154:1077-1087 [1983]; and Weinrauch et al., J. Bacteriol., 169:1205-1211 [1987]). In this method, the incoming donor plasmid recombines with the homologous region of the resident "helper" plasmid in a process that mimics chromosomal transformation.

In addition to commonly used methods, in some embodiments, host cells are directly transformed (i.e., an intermediate cell is not used to amplify, or otherwise process, the DNA construct prior to introduction into the host cell). Introduction of the DNA construct into the host cell includes those physical and chemical methods known in the art to introduce DNA into a host cell without insertion into a plasmid or vector. Such methods include, but are not limited to calcium chloride precipitation, electroporation, naked DNA, liposomes and the like. In additional embodiments, DNA constructs are cotransformed with a plasmid, without being inserted into the plasmid. In further embodiments, a selective marker is deleted from the altered *Bacillus* strain by methods known in the art (See, Stahl et al., J. Bacteriol., 158:411-418 [1984]; and Palmeros et al., Gene 247:255-264 [2000]).

In some embodiments, the transformed cells of the present invention are cultured in conventional nutrient media. The suitable specific culture conditions, such as temperature, pH and the like are known to those skilled in the art. In addition, some culture conditions may be found in the scientific literature such as Hopwood (2000) *Practical Streptomyces Genetics*, John Innes Foundation, Norwich UK; Hardwood et al., (1990) *Molecular Biological Methods for Bacillus*, John Wiley and from the American Type Culture Collection (ATCC).

In some embodiments, host cells transformed with polynucleotide sequences encoding modified proteases are cultured in a suitable nutrient medium under conditions permitting the expression of the present protease, after which the resulting protease is recovered from the culture. The medium used to culture the cells comprises any conventional medium suitable for growing the host cells, such as minimal or complex media containing appropriate supplements. Suitable media are available from commercial suppliers or may be prepared according to published recipes (e.g., in catalogues of the American Type Culture Collection). In some embodiments, the protease produced by the cells is recovered from the culture medium by conventional procedures, including, but not limited to separating the host cells from the medium by centrifugation or filtration, precipitating the proteinaceous components of the supernatant or filtrate by means of a salt (e.g., ammonium sulfate), chromatographic purification (e.g., ion exchange, gel filtration, affinity, etc.). Thus, any method suitable for recovering the protease(s) of the present invention finds use in the present invention. Indeed, it is not intended that the present invention be limited to any particular purification method.

The protein produced by a recombinant host cell comprising a modified protease of the present invention is secreted into the culture media. In some embodiments, other recombinant constructions join the heterologous or homologous polynucleotide sequences to nucleotide sequence encoding a protease polypeptide domain which facilitates purification of the soluble proteins (Kroll D J et al (1993) DNA Cell Biol 12:441-53). Such purification facilitating domains include, but are not limited to, metal chelating peptides such as histidine-tryptophan modules that allow purification on immobilized metals (Porath J (1992) Protein Expr Purif 3:263-281), protein A domains that allow purification on immobilized immunoglobulin, and the domain utilized in the FLAGS extension/affinity purification system (Immunex Corp, Seattle Wash.). The inclusion of a cleavable linker sequence such as Factor XA or enterokinase (Invitrogen, San Diego Calif.) between the purification domain and the heterologous protein also find use to facilitate purification.

As indicated above, the invention provides for modified full-length polynucleotides that encode modified full-length proteases that are processed by a *Bacillus* host cell to produce the mature form at a level that is greater than that of the same mature protease when processed from an unmodified full-length enzyme by a *Bacillus* host cell grown under the same conditions. The level of production is determined by the level of activity of the secreted enzyme.

One measure of production can be determined as relative activity, which is expressed as a percent of the ratio of the value of the enzymatic activity of the mature form when processed from the modified protease to the value of the enzymatic activity of the mature form when processed from the unmodified precursor protease. A relative activity equal or greater than 100% indicates that the mature form a protease that is processed from a modified precursor is produced at a level that is equal or greater than the level at which the same mature protease is produced but when processed from an unmodified precursor. Thus, in some embodiments, the relative activity of a mature protease processed from the modified protease is at least about 100%, at least about 110%, at least about 120%, at least about 130%, at least about 140%, at least about 150%, at least about 160%, at least about 170%, at least about 180%, at least about 190%, at least about 200%, at least about 225%, at least about 250%, at least about 275%, at least about 300%, at least about 325%, at least about 350%, at least about 375%, at least about 400%, at least about 425%, at least about 450%, at least about 475%, at least about 500%, at least about 525%, at least about 550%, at least about 575%, at least about 600%, at least about 625%, at least about 650%, at least about 675%, at least about 700%, at least about 725%, at least about 750%, at least about 800%, at least about 825%, at least about 850%, at least about 875%, at least about 850%, at least about 875%, at least about 900%, and up to at least about 1000% or more when compared to the corresponding production of the mature form of the protease that was processed from the unmodified precursor protease. Alternatively, the relative activity is expressed as the ratio of production which is determined by dividing the value of the activity of the protease processed from a modified precursor by the value of the activity of the same protease when processed from an unmodified precursor. Thus, in some embodiments, the ratio of production of a mature protease processed from a modified precursor is at least about 1, at least about 1.1, at least about 1.2, at least about 1.3 at least about, 1.4, at least about 1.5, at least about 1.6, at least about 1.7, at least about 1.8, at least about 1.9, at least about 2, at least about 2.25, at least about 2.5, at least about 2.75, at least about 3, at least about 3.25, at least about 3.5, at least about 3.75, at least about, at least about 4.25, at least about 4.5, at least about 4.75, at least about 5, at least about 5.25, at least about 5.5, at least about 5.75, at least about 6, at least about 6.25, at least about 6.5, at least about 6.75, at least about 7, at least about 7.25, at least about 7.5, at least about 8, at least about 8.25, at least about 8.5, at least about 8.75, at least about 9, and up to at least about 10.

There are various assays known to those of ordinary skill in the art for detecting and measuring activity of proteases. In particular, assays are available for measuring protease activity that are based on the release of acid-soluble peptides from casein or hemoglobin, measured as absorbance at 280 nm or colorimetrically using the Folin method (See e.g., Bergmeyer et al., "Methods of Enzymatic Analysis" vol. 5, *Peptidases, Proteinases and their Inhibitors*, Verlag Chemie, Weinheim [1984]). Some other assays involve the solubilization of chromogenic substrates (See e.g., Ward, "Proteinases," in Fogarty (ed.)., *Microbial Enzymes and Biotechnology*, Applied Science, London, [1983], pp 251-317). Other exemplary assays include, but are not limited to succinyl-Ala-Ala-Pro-Phe-para nitroanilide assay (SAAPFpNA) and the 2,4,6-trinitrobenzene sulfonate sodium salt assay (TNBS assay). Numerous additional references known to those in the art provide suitable methods (See e.g., Wells et al., Nucleic Acids Res. 11:7911-7925 [1983]; Christianson et al., Anal. Biochem., 223:119-129 [1994]; and Hsia et al., Anal Biochem., 242: 221-227 [1999]). It is not intended that the present invention be limited to any particular assay method(s).

Other means for determining the levels of production of a mature protease in a host cell include, but are not limited to methods that use either polyclonal or monoclonal antibodies specific for the protein. Examples include, but are not limited to enzyme-linked immunosorbent assays (ELISA), radioimmunoassays (RIA), fluorescent immunoassays (FIA), and fluorescent activated cell sorting (FACS). These and other assays are well known in the art (See e.g., Maddox et al., J. Exp. Med., 158:1211 [1983]).

All publications and patents mentioned herein are herein incorporated by reference. Various modifications and variations of the described method and system of the invention will be apparent to those skilled in the art without departing from the scope and spirit of the invention. Although the invention has been described in connection with specific embodiments, it should be understood that the invention as should not be unduly limited to such specific embodiments. Indeed, various modifications of the described modes for carrying out the invention that are obvious to those skilled in the art and/or related fields are intended to be within the scope of the present invention.

EXPERIMENTAL

In the experimental disclosure which follows, the following abbreviations apply: ppm (parts per million); M (molar); mM (millimolar); µM (micromolar); nM (nanomolar); mol (moles); mmol (millimoles); pmol (picomoles); nmol (nanomoles); gm (grams); mg (milligrams); µg (micrograms); pg (picograms); L (liters); ml and mL (milliliters); µl and µL (microliters); cm (centimeters); mm (millimeters); µm (micrometers); nm (nanometers); U (units); V (volts); MW (molecular weight); sec (seconds); min(s) (minute/minutes); h(s) and hr(s) (hour/hours); ° C. (degrees Centigrade); QS (quantity sufficient); QC (QuikChange), ND (not done); NA (not applicable); rpm (revolutions per minute); w/v (weight to volume); v/v (volume to volume); g (gravity); OD (optical density); aa (amino acid); by (base pair); kb (kilobase pair); kD (kilodaltons); suc-AAPF-pNA (succinyl-L-alanyl-L-alanyl-L-prolyl-L-phenyl-alanyl-para-nitroanilide); DMSO (dimethyl sulfoxide); cDNA (copy or complementary DNA); DNA (deoxyribonucleic acid); ssDNA (single stranded DNA); dsDNA (double stranded DNA); dNTP (deoxyribonucleotide triphosphate); DTT (1,4-dithio-DL-threitol); H2O (water); dH2O (deionized water); HCl (hydrochloric acid); MgCl$_2$ (magnesium chloride); MOPS (3-[N-morpholino] propanesulfonic acid); NaCl (sodium chloride); PAGE (polyacrylamide gel electrophoresis); PBS (phosphate buffered saline [150 mM NaCl, 10 mM sodium phosphate buffer, pH 7.2]); PEG (polyethylene glycol); PCR (polymerase chain reaction); PMSF (phenylmethylsulfonyl fluoride); RNA (ribonucleic acid); SDS (sodium dodecyl sulfate); Tris (tris (hydroxymethyl) aminomethane); SOC (2% Bacto-Tryptone, 0.5% Bacto Yeast Extract, 10 mM NaCl, 2.5 mM KCl); Terrific Broth (TB; 12 g/l Bacto Tryptone, 24 g/l glycerol, 2.31 g/l KH$_2$PO$_4$, and 12.54 g/l K$_2$HPO$_4$); OD280 (optical density at 280 nm); OD600 (optical density at 600 nm); A405 (absorbance at 405 nm); Vmax (the maximum initial velocity of an enzyme catalyzed reaction); HEPES (N-[2-Hydroxyethyl]piperazine-N-[2-ethanesulfonic acid]); Tris-HCl (tris [Hydroxymethyl]aminomethane-hydrochloride); TCA (trichloroacetic acid); HPLC (high pressure liquid chromatography); RP-HPLC (reverse phase high pressure liquid chromatography); TLC (thin layer chromatography); EDTA (ethylenediaminetetracetic acid); EtOH (ethanol); SDS (sodium dodecyl sulfate); Tris (tris(hydroxymethyl)aminomethane); i (N,N,N'N'-tetraacetylethylenediamine).

The following examples are provided in order to demonstrate and further illustrate certain embodiments and aspects of the present invention and are not to be construed as limiting the scope thereof.

To determine the effect of amino acid substitutions in the alkaline protease pro region on the production of the mature form of the protease to which the pro region is operably linked, one, two and three amino acid substitutions were introduced at amino acids at positions 6, 30 and 32 of the pro region of SEQ ID NO:7 when operably linked to the mature proteases of SEQ ID NOS:9, 11, 17, 19, and 21 as described in Examples 1-5, respectively.

EXAMPLE 1

The Effect of Mutations in the Pro Region of SEQ ID NO:7 on the Production of the Mature Alkaline Protease of SEQ ID NO:9

(a) Site-Saturation Mutagenesis of Amino Acids at Positions 6, 30 or 32 of the Pro Region Site-saturation mutagenesis of the pro region on the production of the mature protease of SEQ ID NO:9 was performed using the QuikChange® site-directed mutagenesis kit (QC; Stratagene) according to the directions of the manufacturer. A DNA cassette comprising the AprE promoter, and the polynucleotide that encodes the full-length protease of SEQ ID NO:59 was cloned into the EcoRI and HindIII restriction sites of the pJH101 vector (Ferrari et al. J. Bacteriol. 154: 1513-1515 [1983]) pJH-Pn (FIG. 4A) to generate the pJH-P9 plasmid. (Pn refers to the SEQ ID NO of the mature protease that is expressed from the pJH-Pn plasmid). The DNA cassette comprised the *B. subtilis* aprE promoter gaattcctccattttcttctgctatcaaaataaca-gactcgtgattttccaaacgagctttcaaaaaagcctctgccccttgcaaatcg gatgcctgtctataaaattcccgatat-tggttaaacagcggcgcaatggcggccg-catctgatgtctttgcttggcgaatgttcatctt atttcttcctccctctcaataattUt-tcattctatccattctgtaaagtttattttcagaatacttttatcatcatgctttgaaaaaa tatcac gataatatccattgttctcacggaagca-cacgcaggtcatttgaacgaattUttc-gacaggaatttgccgggactcaggagcattta acctaaaaaagcatga-catttcagcataatgaacatttactcatgtctattttcgttcttttctgtatgaaaatagttat ttcgagtctctac ggaaatagcgagagatgatatac-ctaaatagagataaaatcatct-caaaaaaatgggtctactaaaatattattccatctattaca ataaattcacagaatag-tatttaagtaagtctactctgaatttttttaaaaggagagggtaaaga (SEQ ID NO:1), the polynucleotide sequence gtgagaagcaaaaaattgtggatcagct-tgttgtttgcgttaacgttaatctttacgatggcgttcagcaacatgtctgcgcaggct (SEQ ID NO:2), which encodes the AprE signal peptide VRSKKLWISLLFALTLIFTMAFSNMSAQA (SEQ ID NO:3), the polynucleotide sequence gctgaagaagcaaaagaaaaatatt-taattggctttaatgagcaggaagctgt-cagtgagtttgtagaacaagtagaggcaaat gacgaggtcgccattctctctgag-gaagaggaagtcgaaattgaattgcttcatgaatttgaaacgattcctgttttatccgtt gagtt aagcccagaagatgtggacgcgct-tgaactcgatccagcgatttcttatattgaagaggatgcagaagtaacgacaatg (SEQ ID NO:6), which encodes the unmodified pro region AEEAKEKYLIGFNEQEAVSEFVEQVEAN-DEVAILSEEEEVEIELLHEFETIPVLSVELSPEDVD ALELDPAISYIEEDAEVTTM (SEQ ID NO:7), and the polynucleotide sequence gcgcaatcagtgccatgggaattagc-cgtgtgcaagcccagctgcccataac-cgtggattgacaggttctggtgtaaaagttg ctgtcctcgatacaggtatttccact-catccagacttaaatattcgtggtggcgctagctttgtaccaggggaaccatccactc aaga tgggaatgggcatggcacgcatgtggc-
cgggacgattgctgctttaaacaattc-
gattggcgttcttggcgtagcgccgagcgcg gaactatacgctgttaaagtatt-
aggggcgagcggttcaggttcggtcagctcgattgcccaaggattggaatgggca
gggaac aatggcatgcacgttgctaatttgagtt-
taggaagcccttcgccaagtgccacact-tgagcaagctgttaatagcgcgacttctaga ggcgttcttgttgtagcggcatctg-
gaaattcaggtgcaggctcaatcagctatccggcccgttatgcgaacgcaatggca
gtcgg agctactgaccaaaacaacaaccgcgc-
cagcttttcacagtatggcgcagggcttgacattgtcgcaccaggtgtaaacgtca
gagcacatacccaggttcaacgtatgc-
cagcttaaacggtacatcgatggc-
tactcctcatgttgcaggtgcagcagcccttgtta aacaaaagaacccatcttggtc-
caatgtacaaatccgcaatcatctaaagaatacggcaacgagcttaggaagcacga
acttg tatggaagcggacttgtcaatgcagaagctgcaactcgt (SEQ ID
NO:8),
which encodes the mature region of protease 9 (P9). AQSVP-
WGISRVQAPAAHNRGLTGSGVKVAVLDT-
GISTHPDLNIRGGASFVPGEPSTQDGN GHGTHVAG-
TIAALNNSIGVLGVAPSAELYAVKVLGASGSGSVSSIA
QGLEWAGNNGMHVA NLSLGSPSPSATLEQAVN-
SATSRGVLVVAASGNSGAGSISYPARY-
ANAMAVGATDQNNNR ASFSQYGAGLDIVAPGVN-
VQSTYPGSTYASLNGTSMATPHVAGAAALVKQKNPS
WSNVQI RNHLKNTATSLGSTNLYGSGLVNAEAATR
(SEQ ID NO:9).

Each of the 3 codons in the pro region of SEQ ID NO:7, exemplified by NNG/C, comprised in the full-length protease of SEQ ID NO:59, were mutated to be substituted by the 32 possible nucleotide triplets that encode the 20 naturally occurring amino acids to generate three libraries as follows. An aliquot of plasmid pJH-P9 DNA comprising the sequence encoding the full-length protease was mutated to generate a first library of clones encoding all possible substitutions of glutamic acid (E) at position 6 (E6X) of the pro region (SEQ ID NO:7); a second aliquot was mutated to generate a second library of clones encoding all possible substitutions of glutamic acid (E) at position 30 (E30X) of the pro region (SEQ ID NO:7); and a third aliquot was mutated to generate a third library of clones encoding all possible substitutions of arginine (A) at position 32 (A32X) of the pro region (SEQ ID NO:7). Complementary overlapping primers were designed for mutating the codons of interest with about 18 bases flanking the NNS codon. The polynucleotide sequences of the forward and reverse primers used to mutate the amino acids at positions 6, 30 and 32 are given in Table 1.

TABLE 1

| Primer Name* | Primer Sequence | Bases Left** | Bases Right*** |
|---|---|---|---|
| 6F | GCTGCTGAAGAAGCAAAANNSAAATATT TAATTGGCTTTAATG (SEQ ID NO: 26) | 18 | 22 |
| 6R | CATTAAAGCCAATTAAATATTTSNNTTTT GCTTCTTCAGCAGC (SEQ ID NO: 27) | 22 | 18 |
| 30F | CAAGTAGAGGCAAATGACNNSGTCGCC ATTCTCTCTGAG (SEQ ID NO: 28) | 18 | 18 |
| 30R | CTCAGAGAGAATGGCGACSNNGTCATT TGCCTCTACTTG (SEQ ID NO: 29) | 18 | 18 |
| 32F | GAGGCAAATGACGAGGTCNNSATTCTC TCTGAGGAAGAG (SEQ ID NO: 30) | 18 | 18 |
| 32R | CTCTTCCTCAGAGAGAATSNNGACCTCG TCATTTGCCTC (SEQ ID NO: 31) | 18 | 18 |

*The primer names provided indicate the amino acid position at which the substitution is made; "R" indicates that the primer is the reverse primer and "F" indicates that the primer is a forward primer. For example, 6F is the forward primer that was used in the substitution of amino acid at position 6 of the pro sequence set forth in SEQ ID NO: 7.
"Bases left" and *"Bases Right" indicate the number of bases to the left and to the right of the mutating codon ("NNS") that are present in the primer. These bases are complementary to the bases of the template precursor polynucleotide bases.

pJH-P9 DNA was used as template in the QuikChange (QC) mutagenesis reaction as follows. Two microliters of pJH-P9 miniprep DNA (50 ng) were added to 40. μL of sterile distilled H$_2$O, 1 μL of PfuTurbo, 5 ul 10×Pfu buffer, 1 μL dNTPs (Roche), 0.5 μL of forward primer (5 uM), and 0.5 μl reverse primer (5 uM), for a total of 50 μL. The DNA amplification reaction (PCR) was performed under the following cycling conditions: 95° C. for 1 min, once, followed by 19-20 cycles of 95° C. for 1 min., 55° C. for 1 min, and 68° C. for 12 min. Five microliters of the PCR reaction were analyzed by electrophoresis using a 1.2% E-gel (Invitrogen). Subsequently, the mutated amplified DNA was digested twice, using 1 μL DpnI at 37° C. for 2 to 8 hours. A negative control was generated under similar conditions, but in the absence of primers. One microliter of each of the DpnI-digested reaction products was used to transform fifty microliters of one-shot TOP10 chemically competent cells (Invitrogen) using the manufacturer's protocol. The transformed cells were grown in Luria's Broth (LB) with shaking at 37 C for 1 hour, then streaked on Luria Agar (LA) plates containing 50 ppm carbenicillin, and allowed to grow at 37° C. overnight. Following the overnight incubation, individual colonies were picked, used to inoculate 150 μL of LB containing 50 ppm carbenicillin, and grown overnight at 37° C. in 96-well microtiter plates. An aliquot of the culture grown in the micro titer plates was transferred to LA plates containing 50 ppm carbenicillin, and the plates were sent to Quintara Inc. for isolation and sequence analysis of the mutated DNA. Glycerol was added to a final concentration of 20% to the cultures remaining in the microtiter plates, which were then frozen at −80° C. and stored.

(b) Generation of *B. Subtilis* Strains Expressing Modified Pn Proteases.

Aliquots of the *E. coli* microtiter cell cultures harboring the mutated pro sequences were used to inoculate 5 ml of LB+50 ppm carbenicillin. Plasmid DNA was prepared using a Qiagen kit (Qiagen), and a portion of each plasmid DNA was used to transform *B. subtilis* host cells. Ten microliters of the plasmid DNA (pJH-P9) were used to transform 100 ul of *B. subtilis* comK competent cells (genotype: ΔaprE, ΔnprE, degUHy32, oppA, DspoIIE3501, amyE::xylRPxylAcomK-phleo). A control plasmid containing the P9 construct comprising the unmutated pro sequence (unmutated SEQ ID NO:7) was also transformed to *B. subtilis* comK cells. The transformed cells were incubated at 37° C. for 45 minutes while shaking at 250 rpm. Cells from the transformation mixture were plated onto LA plates containing 1.6% skim milk and 5 ppm chloramphenicol (CMP) and incubated overnight in at 37° C. One colony, from each of the transformations, was picked and re-streaked on the LA plates containing 5 ppm CMP+1.6% skim milk.

Bacterial colonies harboring the control plasmid or a plasmid encoding a modified protease were used to inoculate 150 uL of Luria Broth containing 5 ppm CMP in wells of a microtiter plate. The microtiter plates were then incubated for four hours at 37° C. while rotating at 250 rpm. 10 ul of each of the cultures were transferred to a new micro-titer plate containing 140 ul of Grants II media, pH 7.3, and the cultures were grown in a shaking incubator at 37° C., 250 rpm for 40 hours. (Grants II media was prepared as follows: Solution I: 10 g of Soytone were dissolved in 500 ml water and autoclaved for 20-25 minutes; Solution II: 3 ml of 1M K2HPO4, 75 g glucose, 3.6 g urea, 100 ml Grant's 10×MOPS were diluted into 400 ml water. Solutions I and II were mixed and the pH adjusted to pH7.3 with HCl/NaOH. The final volume was adjusted to 1 L, and the final solution was sterilized through 0.22-um PES filter.) Following the incubation, the microtiter plates were centrifuged and the supernatant of each of the cultures was assayed for protease activity using the AAPF assay described below.

(c) Measurement of Modified Protease Production: AAPF Assay of Protease Activity Each of the *B. subtilis* cultures obtained as described in Example 1(b), was assayed for the production of the modified proteases. The enzymes produced were assayed for activity against the substrate, succinyl -L-Ala-L-Ala-L-Pro-L-Phe-p-nitroanalide (AAPF). The assay measured the production of modified protease as the increase in absorbance at 405 nm/min resulting from the hydrolysis and release of p-nitroanaline (Estell et al., J Biol. Chem., 260:6518-6521 (1985)). The measurements were made using the Softmax Pro software, and the specified conditions were set as: Type: Kinetic; Reduction: Vmax Points (Read best 15/28 points); Lm1: 405 nm; Time: 5 minutes; and Interval: 11 Seconds. Ten microliters of each of the *B. subtilis* cultures were diluted to 100 ul of Tris Buffer, containing 10 mM Tris+0.005% TWEEN®-80, pH 8.6; and 25 ul of 100 mg/ml AAPF substrate to assay for protease activity. The relative activity of each of the modified proteases was calculated, and the effect of each amino acid substitution on the production of the corresponding modified protease was determined as a ratio of the activity of the mature protease processed from each modified protease to the activity of the mature protease processed from the unmodified protease precursor protease. Once the DNA construct was stably integrated into a competent *Bacillus subtilis* strain, the activity of the modified proteases was measured in microtiter assays and the activity was compared to the activity of the corresponding protease processed from the unmodified precursor.

Ten microliters of overnight Grant II Media cell cultures were diluted to 100 ul of Tris Buffer, containing 10 mM Tris+0.005% TWEEN®-80 pH 8.6; and 25 ul of 100 mg/ml AAPF substrate were used to assay for protease activity. Assays were done in microtiter plates and the Softmax Pro Software was used.

The results given in Tables 2, 3, and 4, showed that all but one of the amino acid substitutions of amino acids at positions 6 of the pro region (SEQ ID NO:7) within the precursor protease (SEQ ID NO:59) lead to an enhanced production of the mature form of the protease of SEQ ID NO:9, whereas all but one of the amino acid substitutions at positions 30 or 32 showed similar or diminished protease production when compared to the production of the mature protease when processed from an unmodified pro region. In addition, site saturation of each of the substituted amino acids showed that each amino acid can be substituted by two or more amino acids at the same position to increase the production of the mature form relative to that obtained from the precursor protease having unmodified pro region.

TABLE 2

Effect of amino acid substitution at position 6 of the pro region on the production of the mature protease of SEQ ID NO: 9

| Mutation (Substitution) at position in pro region | Percent activity relative to activity from the unmodified precursor |
|---|---|
| E6 (control) | 100 |
| E6A | 119 |
| E6R | 236 |
| E6N | 377 |
| E6C | 425 |
| E6Q | 455 |
| E6G | 458 |
| E6H | 117 |
| E6M | 280 |
| E6F | 411 |
| E6P | 529 |
| E6S | 512 |
| E6T | 480 |
| E6W | 277 |
| E6Y | 7 |
| E6V | 550 |

TABLE 3

Effect of amino acid substitution at position 30 of the pro region on the production of the mature protease of SEQ ID NO: 9

| Mutation (Substitution) at position in pro region | Percent activity relative to the unmodified precursor |
|---|---|
| E30 (control) | 100 |
| E30A | 76 |
| E30R | 73 |
| E30N | 82 |
| E30D | 80 |
| E30G | 47 |
| E30H | 78 |
| E30I | 61 |
| E30L | 66 |
| E30M | 75 |
| E30F | 70 |
| E30P | 69 |
| E30S | 73 |
| E30T | 83 |
| E30W | 62 |
| E30V | 60 |

TABLE 4

Effect of amino acid substitution at position 32 of the pro region on the production of the mature protease of SEQ ID NO: 9

| Mutation (Substitution) at positions in pro region | Percent activity relative to activity from the unmodified precursor |
|---|---|
| A32 (control) | 100 |
| A32R | 64 |
| A32N | 76 |
| A32Q | 75 |
| A32E | 46 |
| A32G | 78 |
| A32H | 60 |
| A32I | 67 |
| A32L | 76 |
| A32K | 121 |
| A32F | 32 |
| A32P | 37 |
| A32S | 74 |
| A32T | 99 |
| A32W | 80 |
| A32V | 98 |

(d) Site-Saturation Mutagenesis: Generation of Combinations of Substitutions in the Pro Region The plasmid expressing the A32K substitution in the pro region (SEQ ID NO:7) comprised in the full-length protease of SEQ ID NO:59 was subjected to a second round of site-saturation mutagenesis of the codon at position 6 to create a first library of polynucleotides that encode a full-length protease containing a substitution of amino acid 6 in combination with the A32K substitution of the pro region of the protease. The mutation at position 6 was created using the QuikChange® site-directed mutagenesis kit (QC; Stratagene) according to the directions provided by the manufacturer using forward and reverse primers of SEQ ID NOS:26 and 27, respectively. Similarly, a second library of polynucleotides was created to encode a full-length protease containing a substitution of amino acid 30 in combination with the A32K substitution in the pro region of the protease was created. The complementary overlapping forward (CAAGTAGAGGCAAATGACNNSGTCAAAATTCTCTCTGAG; SEQ ID NO:32) and reverse primers (CTCAGAGAGAATTTTGACSNNGTCATTTGCCTCTACTTG; SEQ ID NO:33) were used for mutating the position 30.

The QC reaction, amplification of the plasmid DNA, and transformation of *E. coli* cells were performed as described in Example 1(a). The subsequent transformation of *Bacillus subtilis* competent cells was also performed as described in Example 1(b). Supernatants from *Bacillus* cultures expressing proteases from modified or unmodified precursor were analyzed for protease activity using the AAPF assay as described in Example 1(c).

Results shown in Tables 5 and 6 indicate that most substitutions of the amino acid at position 6 (Table 5) of the pro region when in combination with the substitution A32K further enhance the production of the mature form of the protease expressed from a polynucleotide encoding an unmodified pro region or a pro region containing the A32K substitution. However, the combination of amino acid substitutions at position 30 when in combination with the A32K substitution did not enhance the production of the mature protease of SEQ ID NO:9 (Table 6).

TABLE 5

Effect of the combination of amino acid substitution A32K with substitutions of amino acid at position 6 of the pro region on the production of mature protease of SEQ ID NO: 9

| Mutation (Substitution) at positions in pro region | Percent activity relative to activity from the modified precursor E6-A32K |
|---|---|
| E6-A32K (control, modified) | 100 |
| E6R-A32K | 160 |
| E6N-A32K | 120 |
| E6D-A32K | 170 |
| E6C-A32K | 71 |
| E6G-A32K | 79 |
| E6I-A32K | 103 |
| E6L-A32K | 50 |
| E6K-A32K | 132 |
| E6M-A32K | 127 |
| E6F-A32K | 71 |
| E6P-A32K | 161 |
| E6S-A32K | 82 |
| E6T-A32K | 134 |
| E6W-A32K | 60 |
| E6Y-A32K | 95 |
| E6V-A32K | 63 |

TABLE 6

Effect of the combination of amino acid substitution A32K with substitutions of amino acid at position 30 of the pro region on the production of mature protease of SEQ ID NO: 9

| Mutation (substitution) at positions in pro region | Percent activity relative to activity from the modified precursor E30-A32K |
|---|---|
| E30-A32K (control, modified) | 100 |
| E30A-A32K | 38 |
| E30R-A32K | 33 |
| E30N-A32K | 33 |
| E30D-A32K | 34 |
| E30C-A32K | 33 |
| E30Q-A32K | 33 |
| E30G-A32K | 38 |
| E30H-A32K | 40 |
| E30I-A32K | 30 |
| E30L-A32K | 33 |
| E30K-A32K | 47 |
| E30M-A32K | 45 |
| E30F-A32K | 36 |
| E30P-A32K | 72 |
| E30S-A32K | 67 |
| E30T-A32K | 26 |
| E30W-A32K | 85 |
| E30Y-A32K | 96 |
| E30V-A32K | 65 |

(e) Effect of Amino Acid Substitution(s) in the Pro Region of the Precursor Protease on the Production of the Mature Protease of SEQ ID NO:9 in Shake Flask Cultures.

To test the effect of amino acid substitutions in the pro region on the production of the mature protease of SEQ ID NO:9 in shake flask cultures, several of the *Bacillus subtilis* strains grown in the microtiter plates as described above were grown as follows. *Bacillus subtilis* strains expressing the modified precursor comprising a single substitution at one of positions 6, 30 and 32 of the pro region, or comprising a combination of two substitutions of amino acids at positions 6 and 32, or 30 and 32 of the pro region and that were previously grown in microtiter plates, were first plated on Luria Agar plates containing 5 ppm chloramphenicol and 1.6% skim milk. A single colony was used to inoculate 5 ml of Luria Broth containing 5 ppm chloramphenicol. Each 5 ml culture was grown for 5 hours at 37° C. while shaking at 250 rpm. A 250 ml shake flask containing 25 ml of Grant's II media was inoculated with 1 ml of the 5 ml culture of strains comprising a single substitution, and the 250 ml culture was incubated for 40, at 37° C. while shaking at 250 rpm. Strains comprising double substitutions were grown for 40 and/or for 48 hours, as shown by the data given in Tables 9 and 10. Supernatant from the shake flask cultures was assayed for AAPF activity as described in Example 1(c). The results for the activity in strains comprising a single substitution are shown in Tables 7 and 8, and the results for the activity in strains comprising a substitution at position 6 or 32 in combination with the A32K substitution are shown in Tables 9 and 10, respectively.

The results show that the enhancement of protease production obtained from modified precursor proteases in microtiter cultures is mimicked in most shake flask cultures. Eight of 22 strains did not mirror the production of protease in shake flask that was seen in microtiter plates. Four of the eight strains, which produced more protease than their respective controls when grown in microtiter plates produced less protease than the respective controls when grown in shake flasks (E6C, E6F, E6D-A32K and E6K-A32K). The remaining four strains, which produced less protease than their respective controls when grown in microtiter plates produced more protease than the respective controls when grown in shake flasks (A32T, A32V, E6S-A32K, E30V-A32K, and E30W-A32K). It is likely that the production of protease by these strains is affected by the different growth conditions imposed in microtiter versus shake flask cultures. One skilled in the art would know how to optimize growth conditions.

TABLE 7

Effect of amino acid substitution at position 6 of the pro region on the production of the mature protease of SEQ ID NO: 9 in shake flask cultures

| Mutation (substitution) at position in pro region | Percent activity relative to activity from the unmodified precursor (48 hours) |
|---|---|
| E6 (control) | 100 |
| E6N | 111 |
| E6C | 84 |
| E6Q | 149 |
| E6G | 140 |
| E6F | 91 |
| E6P | 110 |
| E6S | 114 |
| E6T | 113 |
| E6V | 145 |

TABLE 8

Effect of amino acid substitution at position 32 of the pro region of the mature protease of SEQ ID NO: 9 in shake flask cultures

| Mutation (substitution) at positions in pro region | Percent activity relative to activity from the unmodified precursor (48 hours) |
|---|---|
| A32 (control) | 100 |
| A32K | 140 |
| A32T | 260 |
| A32V | 190 |

TABLE 9

Effect of the combination of amino acid substitution A32K with substitutions of amino acid at position 6 of the pro region of the mature protease of SEQ ID NO: 9 in shake flask cultures

| Mutation (substitution) at positions in pro region | Percent activity relative to activity from the modified precursor A32K | |
|---|---|---|
| | 40 hours | 48 hours |
| E6-A32K (control, modified) | 100 | 100 |
| E6R-A32K | 108 | 126 |
| E6N-A32K | 91 | 110 |
| E6D-A32K | 64 | 80 |
| E6K-A32K | 59 | 65 |
| E6M-A32K | 126 | 179 |
| E6S-A32K | 77 | 106 |

TABLE 10

Effect of the combination of amino acid substitution A32K with substitutions of amino acid at position 30 of the pro region of the mature protease of SEQ ID NO: 9 in shake flask cultures

| Mutation (substitution) at positions in pro region of GG36 precursor | Percent activity relative to activity from the modified precursor A32K | |
|---|---|---|
| | 40 hours | 48 hours |
| E30-A32K (control, modified) | 100 | 100 |
| E30P-A32K | 73 | 86 |
| E30W-A32K | 130 | 93 |
| E30Y-A32K | 90 | 99 |
| E30V-A32K | 92 | 132 |

EXAMPLE 2

The Effect of Mutations in the Pro Region of SEQ ID NO:7 on the Production of the Mature Alkaline Protease of SEQ ID NO:11

Site-Saturation Mutagenesis of Amino Acids at Positions 6, 30 or 32 of the Pro Region Site-saturation mutagenesis of the pro region on the production of the mature protease of SEQ ID NO:11 was performed using the QuikChange® site-directed mutagenesis kit (QC; Stratagene) according to the directions of the manufacturer. A DNA cassette comprising the AprE promoter, and the polynucleotide that encodes the full-length protease of SEQ ID NO:60 was cloned into the EcoRI and HindIII restriction sites of the pJH101 vector (Ferrari et al. J. Bacteriol. 154: 1513-1515 [1983]) pJH-Pn (FIG. 4A) to generate the pJH-P11 plasmid. (Pn refers to the SEQ ID NO of the mature protease that is expressed from the pJH-Pn plasmid). The DNA cassette comprised the *B. subtilis* aprE promoter gaatcctccatttcttctgctat-caaaataacagactcgtgattttc-caaacgagctttcaaaaaagcctctgccccttgcaaatcg gatgcctgtctataaaattcccgatat-tggttaaacagcggcgcaatggcggccg-catctgatgtctttgcttggcgaatgttcatctt atttcttcctccctctcaataattUt-tcattctatccatttctgtaaagtttattttcagaatacttttatcatcatgctttgaaaaaa tatcac gataatatccattgttctcacggaagca-cacgcaggtcatttgaacgaattUttc-gacaggaatttgccgggactcaggagcattta acctaaaaaagcatga-catttcagcataatgaacatttactcatgtctattttcgttcttttctgtatgaaaatagttat ttcgagtctctac ggaaatagcgagagatgatatac-ctaaatagagataaaatcatctcaaaaaaatgggtctactaaaatattattccatctattaca ataaattcacagaatag-tatttaagtaagtctactctgaatttttttaaaaggagagggtaaaga (SEQ ID NO:1),
the polynucleotide sequence gtgagaagcaaaaaattgtggatcagct-tgttgtttgcgttaacgttaatctttacgatggcgttcagcaacatgtcgcgcaggct (SEQ ID NO:2), which encodes the AprE signal peptide VRSKKLWISLLFALTLIFTMAFSNMSAQA (SEQ ID NO:3),
the polynucleotide sequence gctgaagaagcaaaagaaaaatatt-taattggcttaatgagcaggaagctgt-cagtgagtttgtagaacaagtagaggcaaat gacgaggtcgccattctctctgag-gaagaggaagtcgaaattgaattgcttcatgaatttgaaacgattcctgUttatccgt tgagtt aagcccagaagatgtggacgcgct-tgaactcgatccagcgatttcttatattgaagaggatgcagaagtaacgacaatg (SEQ ID NO:6)
which encodes the unmodified pro region AEEAKEKYLIG-FNEQEAVSEFVEQVEANDEVAIL-SEEEEVEIELLHEFETIPVLSVELSP EDVDALELDPAI-SYIEEDAEVTTM (SEQ ID NO:7), and the polynucleotide sequence gcgcaatcagtgccatggggaattagc-cgtgtgcaagccccagctgcccataac-cgtggattgacaggttctggtgtaaaagttg ctgtcctcgatacaggtatttccact-catccagacttaaatattcgtggtggcgctagctttgtaccaggggaaccatccact caaga tgggaatgggcatggcacgcatgtggc-cgggacgattgctgctctagacaattc-gattggcgttcttggcgtagcgccgagcgcg gaactatacgtcgttaaagtatt-agggggcgagcggttcaggcgccatcagctcgattgcccaaggattggaatgggca gggaac aatggcatgcacgttgctaatttgagtt-taggaagcccttcgccaagtgccacact-tgagcaagctgttaatagcgcgacttctaga ggcgttcttgttgtagcggcatctg-gaaattcaggtgcaggctcaatcagctatccggcccgttatgcgaacgcaatggca gtcgg agctactgaccaaaacaacaaccgcgc-cagcttttcacagtatggcgcagggcttgacattgtcgcaccaggtgtaaacgtgca gagcacatacccaggttcaacgtatgc-cagcttaaacggtacatcgatggc-tactcctcatgttgcaggtgcagcagcccttgtta aacaaaagaacccatcttggtc-caatgtacaaatccgcaatcatctaaagaatacggcaacgagcttaggaagcacga acttg tatggaagcggacttgtcaatgcagaagctgcaactcgt
(SEQ ID NO:10), which encodes the mature region of protease P11 (SEQ ID NO:11) AQSVPWGISRVQAPAAHNR-GLTGSGVKVAVLDTGISTHPDLNIRG-GASFVPGEPSTQDGN GHGTHVAGTIAALDNSIGVLGVAPSAE-LYAVKVLGASGSGAISSIAQGLEWAGNNGMHVAN LSLGSPSPSATLEQAVNSATSRGVLV-VAASGNSGAGSISYPARYANAMAVGATDQNNNRA SFSQYGAGLDIVAPGVNVQSTYPGST-YASLNGTSMATPHVAGAAALVKQKNPSWSNVQIR NHLKNTATSLGSTNLYGSGLVNAEAATR (SEQ ID NO:11).

Each of the 3 codons in the pro region of SEQ ID NO:7, exemplified by NNG/C, comprised in the full-length protease of SEQ ID NO:60, were mutated to be substituted by the 32 possible nucleotide triplets that encode the 20 naturally occurring amino acids to generate three libraries as follows. An aliquot of plasmid pJH-P11 DNA comprising the sequence encoding the full-length protease was mutated to generate a first library of clones encoding all possible substitutions of glutamic acid (E) at position 6 (E6X) of the pro region (SEQ ID NO:7); a second aliquot was mutated to generate a second library of clones encoding all possible substitutions of glutamic acid (E) at position 30 (E30X) of the pro region (SEQ ID NO:7); and a third aliquot was mutated to generate a third library of clones encoding all possible substitutions of arginine (A) at position 32 (A32X) of the pro region (SEQ ID NO:7). Complementary overlapping primers were designed for mutating the codons of interest with about 18 bases flanking the NNS codon. The polynucleotide sequences of the forward and reverse primers used to mutate the amino acids at positions 6, 30 and 32 are given in Table 1.

The QC reaction, amplification of the plasmid DNA, and transformation of E. coli cells were performed as described in Example 1(a). The subsequent transformation of Bacillus subtilis competent cells was also performed as described in Example 1(b). Supernatants from Bacillus cultures expressing proteases from modified or unmodified precursor were analyzed for protease activity using the AAPF assay as described in Example 1(c).

The results given in Tables 11, 12, and 13, show that most amino acid substitutions of amino acids at positions 6, 30 and 32 of the pro region (SEQ ID NO:7) in the precursor protease (SEQ ID NO:60) lead to an enhanced production of the mature form of the protease. In addition, site saturation of each of the substituted amino acids showed that each amino acid can be substituted by two or more amino acids at the same position to increase the production of the mature form relative to that obtained from the precursor protease having unmodified pro region.

TABLE 11

Effect of amino acid substitution at position 6 of the pro region on the production of the mature protease of SEQ ID NO: 11

| Mutation (Substitution) at position in pro region | Percent activity relative to activity from the unmodified precursor |
|---|---|
| E6 (control) | 100 |
| E6A | 125 |
| E6R | 120 |
| E6Q | 161 |
| E6G | 187 |
| E6L | 177 |
| E6K | 160 |
| E6M | 165 |
| E6F | 131 |
| E6P | 72 |
| E6S | 56 |
| E6T | 103 |
| E6W | 52 |
| E6V | 265 |

TABLE 12

Effect of amino acid substitution at position 30 of the pro region on the production of the mature protease of SEQ ID NO: 11

| Mutation (Substitution) at position in pro region | Percent activity relative to activity from the unmodified precursor |
|---|---|
| E30 (control) | 100 |
| E30A | 90 |
| E30R | 112 |
| E30N | 97 |
| E30Q | 126 |
| E30G | 111 |
| E30I | 132 |
| E30L | 128 |
| E30M | 152 |
| E30F | 102 |
| E30P | 132 |
| E30T | 125 |
| E30W | 105 |
| E30Y | 125 |
| E30V | 142 |

TABLE 13

Effect of amino acid substitution at position 32 of the pro region on the production of the mature protease of SEQ ID NO: 11

| Mutation (Substitution) at position in pro region | Percent activity relative to activity from the unmodified precursor |
|---|---|
| A30 (control) | 100 |
| A32R | 99 |
| A32D | 98 |
| A32C | 100 |
| A32Q | 11 |
| A32G | 96 |
| A32H | 98 |
| A32L | 98 |
| A32M | 98 |
| A32F | 93 |
| A32P | 93 |
| A32S | 117 |
| A32T | 129 |
| A32V | 124 |

Effect of Amino Acid Substitution(s) in the Pro Region of the Precursor Protease on the Production of the Mature Protease of SEQ ID NO:11 in Shake Flask Cultures To test the effect of amino acid substitutions in the pro region on the production of the mature protease of SEQ ID NO:11 in shake flask cultures, several of the *Bacillus subtilis* strains comprising a substitution at position 6 of the pro region in the precursor protease as described above were grown for 48 hours as described in Example 1(e). Supernatant from the shake flask cultures was assayed for AAPF activity as described in Example 1(c).

The results shown in Table 14 indicate that substitutions made at position 6 of the P11 precursor sequence which were shown to enhance the production of the mature protease (SEQ ID NO:11) in cultures grown in microtiter plates also increase the production of the protease in cultures grown in shake flasks.

TABLE 14

Effect of amino acid substitutions at position 6 of the pro region on the production of the mature protease of SEQ ID NO: 11 in shake flask cultures

| Mutation (substitution) at position in pro region | Percent activity relative to activity from the unmodified precursor (48 hours) |
|---|---|
| E6 (control) | 100 |
| E6A | 157 |
| E6R | 137 |
| E6Q | 82 |
| E6G | 88 |
| E6L | 130 |
| E6K | 121 |
| E6M | 99 |
| E6F | 43 |
| E6V | 116 |

EXAMPLE 3

The Effect of Mutations in the Pro Region of SEQ ID NO:7 on the Production of the Mature Alkaline Protease of SEQ ID NO:19

(a) Site-Saturation Mutagenesis of Amino Acids at Positions 6, 30 or 32 of the Pro Region Site-saturation mutagenesis of the pro region on the production of the mature protease of SEQ ID NO:19 was performed using the QuikChange® site-directed mutagenesis kit (QC; Stratagene) according to the directions of the manufacturer. A DNA cassette comprising the AprE promoter, and the polynucleotide that encodes the full-length protease of SEQ ID NO:64 was cloned into the EcoRI and HindIII restriction sites of the pJH101 vector (Ferrari et al. J. Bacteriol. 154: 1513-1515 [1983]) pJH-Pn (FIG. 4A) to generate the pJH-P19 plasmid. (Pn refers to the SEQ ID NO of the mature protease that is expressed from the pJH-Pn plasmid). The DNA cassette comprised the *B. subtilis* aprE promoter gaat-tcctccattttcttctgctat-
caaaataacagactcgtgattttc-
caaacgagctttcaaaaaagcctctgccccttgcaaatcg
gatgcctgtctataaaattcccgatat-
tggttaaacagcggcgcaatggcggccg-
catctgatgtctttgcttggcgaatgttcatctt  atttcttcctccctctcaataattUt-
tcattctatccatttctgtaaagtttattttcagaatacttttatcatcatgctttgaaaaaa
tatcac                                     gataatatccattgttctcacggaagca-
cacgcaggtcatttgaacgaattllttc-
gacaggaatttgccgggactcaggagcattta   acctaaaaaagcatga-
catttcagcataatgaacatttactcatgtctattttcgttcttttctgtatgaaaatagttat
ttcgagtctctac                      ggaaatagcgagagatgatatac-
ctaaatagagataaaatcatct-
caaaaaaatgggtctactaaaatattattccatctattaca   ataaattcacagaat-
agtcfffitaagtaagtctactctgaattffittaaaaggagagggtaaaga (SEQ ID NO:1),
the polynucleotide sequence gtgagaagcaaaaaattgtggatcagct-
tgttgffigcgttaacgttaatattacgatggcgttcagcaacatgtctgcgcaggct (SEQ ID NO:2), which encodes the AprE signal peptide VRSKKLWISLLFALTLIFTMAFSNMSAQA (SEQ ID NO:3),
the polynucleotide sequence gctgaagaagcaaaagaaaaatatt-
taattggctttaatgagcaggaagctgt-
cagtgagffigtagaacaagtagaggcaaat gacgaggtcgccattctctctgag-
gaagaggaagtcgaaattgaattgcttcatgaatttgaaacgattcctgffitatccgtt
gagtt                               aagcccagaagatgtggacgcgct-
tgaactcgatccagcgafficttatattgaagaggatgcagaagtaacgacaatg (SEQ ID NO:6),
which encodes the unmodified pro region AEEAKEKYLI GFNEQEAVSE FVEQVEANDE VAILSEEEEV EIELL-HEFET IPVLSVELSP EDVDALELDP AISYIEEDAE-VTTM (SEQ ID NO:7), and the polynucleotide sequence gcgcaatcggtaccatggggaattagc-
cgtgtgcaagcccccagctgcccataac-
cgtggattgacaggttctggtgtaaaagttg ctgtcctcgatacaggtafficcact-
catccagacttaaatattcgtggtggcgctagtffigtaccaggggaaccatccactc
aagat                              gggaatgggcatggcacgcatgtg-
gctgggacgattgctgctttaaacaat-
tcgattggcgttcttggcgtagcaccgaacgcgg aactatacgctgttaaagtatt-
aggggcgagcggtggcggttcgaacagctcgattgcccaaggattggaatgggca
gggaac                              aatggcatgcacgttgctaatttgagtt-
taggaagcccttcgccaagtgccacact-
tgagcaagctgttaatagcgcgacttctaga ggcgttcttgttgtagcggcatctg-
gcaattcaggtgcaggctcaatcagctatccggcccgttatgcgaacgcaatggca
gtcgg                               agctactgaccaaaacaacaaccgcgc-
cagctfficacagtatggcgcagggcttgacattgtcgcaccaggtgtaaacgtgca
gagcacatacccaggttcaacgtatgccagcttaaacggtacatcgatggc-
tactcctcatgttgcaggtgcagcagcccttgtta aacaaaagaacccatcttggtc-
caatgtacaaatccgcaatcatctaaagaatacggcaacgagcttaggaagcacga
acttg tatggaagcggacttgtcaatgcagaagcggcaacacgt
(SEQ ID NO:18) encoding mature region of protease 19
(P19) (SEQ ID NO:19) AQSVPWGISRVQAPAAHNR-
GLTGSGVKVAVLDTGISTHPDLNIRG-
GASFVPGEPSTQDGN GHGTHVAGTIAALNNSIGV-
LGVAPNAELYAVKVLGASGGGSNSSIAQGLEWAGNN
GMHVA NLSLGSPSPSATLEQAVNSATSRGVLV-
VAASGNSGAGSISYPARYANAMAVGATDQNNNR
ASFSQYGAGLDIVAPGVNVQSTYPGST-
YASLNGTSMATPHVAGAAALVKQKNPSWSNVQI
RNHLKNTATSLGSTNLYGSGLVNAEAATR (SEQ ID
NO:19).

Two codons in the pro region of SEQ ID NO:7, exemplified by NNG/C, comprised in the full-length protease of SEQ ID NO:64, were mutated to be substituted by the 32 possible nucleotide triplets that encode the 20 naturally occurring amino acids to generate two libraries as follows. An aliquot of plasmid pJH-P19 DNA comprising the sequence encoding the full-length protease was mutated to generate a first library of clones encoding all possible substitutions of glutamic acid (E) at position 6 (E6X) of the pro region (SEQ ID NO:7); and a second aliquot was mutated to generate a second library of clones encoding all possible substitutions of arginine (A) at position 32 (A32X) of the pro region (SEQ ID NO:7). Complementary overlapping primers were designed for mutating the codons of interest with about 18 bases flanking the NNS codon. The polynucleotide sequences of the forward and reverse primers used to mutate the amino acids at positions 6 and 32 are given in Table 1.

The QC reaction, amplification of the plasmid DNA, and transformation of *E. coli* cells were performed as described in Example 1(a). The subsequent transformation of *Bacillus subtilis* competent cells was also performed as described in Example 1(b). Supernatants from *Bacillus* cultures expressing proteases from modified or unmodified precursor were analyzed for protease activity using the AAPF assay as described in Example 1(c).

The results given in Tables 15 and 16 show that amino acid substitution of most of the amino acids of the precursor protease lead to an enhanced production of the mature form of the protease. In addition, site saturation of each of the substituted amino acids showed that each amino acid can be substituted by two or more amino acids at the same position to increase the production of the mature form relative to that obtained from the precursor protease having unmodified pro region.

TABLE 15

Effect of amino acid substitution at position 6 of the pro region on the production of the mature protease of SEQ ID NO: 19

| Mutation (Substitution) at position in pro region | Percent activity relative to activity from the unmodified precursor |
|---|---|
| E6 (control) | 100 |
| E6A | 128 |
| E6C | 25 |
| E6D | 53 |
| E6G | 95 |
| E6H | 133 |
| E6I | 36 |
| E6K | 111 |
| E6L | 50 |
| E6N | 35 |
| E6P | 28 |
| E6Q | 45 |
| E6R | 100 |

TABLE 15-continued

Effect of amino acid substitution at position 6 of the pro region on the production of the mature protease of SEQ ID NO: 19

| Mutation (Substitution) at position in pro region | Percent activity relative to activity from the unmodified precursor |
|---|---|
| E6S | 71 |
| E6W | 31 |
| E6T | 75 |

TABLE 16

Effect of amino acid substitution at position 30 of the pro region on the production of the mature protease of SEQ ID NO: 19

| Mutation (Substitution) at position in pro region | Percent activity relative to activity from the unmodified precursor |
|---|---|
| E30 (control) | 100 |
| E30A | 488 |
| E30R | 384 |
| E30N | 405 |
| E30D | 241 |
| E30G | 374 |
| E30H | 371 |
| E30I | 51 |
| E30L | 211 |
| E30K | 265 |
| E30F | 168 |
| E30P | 66 |
| E30S | 601 |
| E30T | 351 |
| E30V | 254 |

(b) Site-Saturation Mutagenesis: Generation of Combinations of Substitutions in the Pro Region.

The plasmid expressing the E30G substitution in the pro region (SEQ ID NO:7) comprised in the full-length protease of SEQ ID NO:64 was subjected to a second round of site-saturation mutagenesis of the codon at position 6 to create a library of polynucleotides that encode a full-length protease containing a substitution of amino acid 6 in combination with the E30G substitution of the pro region of the protease. The mutation at position 6 was created using the QuikChange® site-directed mutagenesis kit (QC; Stratagene) according to the directions provided by the manufacturer using forward and reverse primers of SEQ ID NOS:26 and 27, respectively.

The QC reaction, amplification of the plasmid DNA, and transformation of *E. coli* cells were performed as described in Example 1(a). The subsequent transformation of *Bacillus subtilis* competent cells was also performed as described in Example 1(b). Supernatants from *Bacillus* cultures expressing proteases from modified or unmodified precursor were analyzed for protease activity using the AAPF assay as described in Example 1(c).

Results shown in Table 17 indicate that most substitutions of amino acid at position 6 of the pro region when in combination with the substitution E30G at amino acid position 30 lead to an enhanced production of the mature form of the protease.

TABLE 17

Effect of the combination of amino acid substitution E30G with substitutions of amino acid at position 6 of the pro region on the production of mature protease of SEQ ID NO: 19

| Mutation (Substitution) at positions in pro region of precursor E6X-E30G | Percent activity relative to activity from the unmodified precursor E6-E30 |
|---|---|
| E6-E30 (control, unmodified) | 100 |
| E6A-E30G | 188 |
| E6R-E30G | 126 |
| E6N-E30G | 158 |
| E6D-E30G | 126 |
| E6C-E30G | 220 |
| E6Q-E30G | 147 |
| E6G-E30G | 107 |
| E6H-E30G | 144 |
| E6L-E30G | 96 |
| E6K-E30G | 117 |
| E6M-E30G | 114 |
| E6F-E30G | 152 |
| E6P-E30G | 108 |
| E6S-E30G | 108 |
| E6T-E30G | 100 |
| E6W-E30G | 104 |
| E6V-E30G | 185 |
| E6Y-E30G | 148 |

(c) Effect of Amino Acid Substitution(s) in the Pro Region of the Precursor Protease on the Production of the Mature Protease of SEQ ID NO:19 in Shake Flask Cultures.

To test the effect of amino acid substitutions in the pro region on the production of the mature protease of SEQ ID NO:19 in shake flask cultures, several of the *Bacillus subtilis* strains grown in the microtiter plates as described above and containing the combinations of substitutions E6A-E30G, E6C-E30G, and E6V-E30G in the pro region were grown for 48 hours as described in Example 1(e). Supernatant from the shake flask cultures was assayed for AAPF activity as described in Example 1(c).

The results shown in Table 18 indicate that the combination of mutations E6A and E30G in the pro region of the protease precursor leads to enhanced production of the mature protease (SEQ ID NO:19) compared to the production of the protease processed from the precursor containing the single mutation E30G.

TABLE 18

Effect of the combination of amino acid substitution E30G with substitutions of amino acid at position 6 of the pro region of the mature protease of SEQ ID NO: 19 in shake flask cultures

| Mutation (substitution) at positions in modified pro region | Percent activity relative to activity from the modified precursor E30G (48 hours) |
|---|---|
| E6-E30G | 100 |
| E6A-E30G | 178 |
| E6C-E30G | 97 |
| E6V-E30G | 92 |

EXAMPLE 4

The Effect of Mutations in the Pro Region of SEQ ID NO:7 on the Production of the Mature Alkaline Protease of SEQ ID NO:17

Site-Saturation Mutagenesis of Amino Acids at Positions 6, 30 or 32 of the Pro Region Site-saturation mutagenesis of the pro region on the production of the mature protease of SEQ ID NO:17 was performed using the QuikChange® site-directed mutagenesis kit (QC; Stratagene) according to the directions of the manufacturer. A DNA cassette comprising the AprE promoter, and the polynucleotide that encodes the full-length protease of SEQ ID NO:63 was cloned into the EcoRI and HindIII restriction sites of the pJH101 vector (Ferrari et al. J. Bacteriol. 154: 1513-1515 [1983]) pJH-Pn (FIG. 4A) to generate the pJH-P17 plasmid. (Pn refers to the SEQ ID NO of the mature protease that is expressed from the pJH-Pn plasmid). The DNA cassette comprised the *B. subtilis* aprE promoter gaatcctccattttcttctgctat-
caaaataacagactcgtgattttc-
caaacgagctttcaaaaaagcctctgccccttgcaaatcg
gatgcctgtctataaaattcccgatat-
tggttaaacagcggcgcaatggcggccg-
catctgatgtctttgcttggcgaatgttcatctt atttcttcctccctctcaataattUt-
tcattctatccatttctgtaaagtttatttttcagaatacttttatcatcatgctttgaaaaaa
tatcac gataatatccattgttctcacggaagca-
cacgcaggtcatttgaacgaattUttc-
gacaggaatttgccgggactcaggagcattta acctaaaaaagcatga-
catttcagcataatgaacatttactcatgtctattttcgttcttttctgtatgaaaatagttat
ttcgagtctctac ggaaatagcgagagatgatatac-
ctaaatagagataaaatcatct-
caaaaaaatgggtctactaaaatattattccatctattaca ataaattcacagaatag-
tatttaagtaagtctactctgaatttttttaaaaggagagggtaaaga (SEQ ID NO:1), the polynucleotide sequence gtgagaagcaaaaaattgtg-
gatcagcttgttgtttgcgttaacgt-
taatctttacgatggcgttcagcaacatgtctgcgcaggct (SEQ ID NO:2), which encodes the AprE signal peptide VRSKKLWISLL-FALTLIFTMAFSNMSAQA (SEQ ID NO:3),
the polynucleotide sequence gctgaagaagcaaaagaaaaatatt-taattggctttaatgagcaggaagctgt-
cagtgagtttgtagaacaagtagaggcaaat gacgaggtcgccattctctctgag-gaagaggaagtcgaaattgaattgcttcatgaatttgaaacgattcctgttttatccgtt
gagtt aagcccagaagatgtgacgcgct-
tgaactcgatccagcgatttcttatattgaagaggatgcagaagtaacgacaatg (SEQ ID NO:6), which encodes the unmodified pro region AEEAKEKYLIGFNEQEAVSEFVEQVEAN-DEVAILSEEEEVEIELLHEFETIPVLSVELSPEDVD ALELDPAISYIEEDAEVTTM (SEQ ID NO:7), and the polynucleotide sequence GCGCAATCGGTACCATGGG-GAATTAGCCGTGTGCAAGCCCCAGCTGC-
CCATAACCGTG GATTGACAGGTTCTGGTG-TAAAAGTTGCTGTCCTCGATACAGGTATTTCCACTC ATCCA GACTTAAATATTCGTGGTG-GCGCTAGCTTTGTACCAGGGGAACCATC-
CACTCAAGATGG GAATGGGCATGGCACGCATGTG-GCTGGGACGATTGCTGCTTTAAACAATTCGATTGGC GTTCTTGGCGTAGCACCGAACGCGGAAC-
TATACGCTGTTAAAGTATTAGGGGCGAGCG GTATGGGTTCGGTCAGCTCGATTGC-
CCAAGGATTGGAATGGGCAGGGAACAATGTTAT GCACGTTGCTAATTTGAGTTTAGGACTG-
CAGGCACCAAGTGCCACACTTGAGCAAGCT GTTAATAGCGCGACTTCTAGAGGCGT-
TCTTGTTGTAGCGGCATCTGGCAATTCAGGTGC AGGCTCAATCAGCTATCCGGCCCGTTAT-
GCGAACGCAATGGCAGTCGGAGCTACTGAC CAAAACAACAACCGCGCCAGCTTTTCA-
CAGTATGGCGCAGGGCTTGACATTGTCGCAC CAG-GTGTAAACGTGCAGAGCACATACCCAG-
GTTCAACGTATGCCAGCTTAAACGGTAC ATCGATGGCTACTCCTCATGTTGCAGGT-
GCAGCAGCCCTTGTTAAACAAAAGAACCCAT CTTGGTCCAATGTACAAATCCGCAAT-
CATCTAAAGAATACGGCAACGAGCTTAGGAAGC ACGAACTTGTATGGAAGCGGACTTGTCAATGCAGAAGCGGCAACACGT (SEQ ID NO:16), which encodes the mature region of protease 17 (P17) AQSVPWGISRVQAPAAHNRGLTGSGVKVAVLDTGISTHPDLNIRGGASFVPGEPSTQDGN GHGTHVAGTIAALNNSIGVLGVAPNAELYAVKVLGASGMGSVSSIAQGLEWAGNNVMHVA NLSLGLQAPSATLEQAVNSATSRGVLVVAASGNSGAGSISYPARYANAMAVGATDQNNNR ASFSQYGAGLDIVAPGVNVQSTYPGSTYASLNGTSMATPHVAGAAALVKQKNPSWSNVQI RNHLKNTATSLGSTNLYGSGLVNAEAATR (SEQ ID NO:17).

Each of the 3 codons in the pro region of SEQ ID NO:7, exemplified by NNG/C, comprised in the full-length protease of SEQ ID NO:63, were mutated to be substituted by the 32 possible nucleotide triplets that encode the 20 naturally occurring amino acids to generate three libraries as follows. An aliquot of plasmid pJH-P17 DNA comprising the sequence encoding the full-length protease was mutated to generate a first library of clones encoding all possible substitutions of glutamic acid (E) at position 6 (E6X) of the pro region (SEQ ID NO:7); a second aliquot was mutated to generate a second library of clones encoding all possible substitutions of glutamic acid (E) at position 30 (E30X) of the pro region (SEQ ID NO:7); and a third aliquot was mutated to generate a third library of clones encoding all possible substitutions of arginine (A) at position 32 (A32X) of the pro region (SEQ ID NO:7). Complementary overlapping primers were designed for mutating the codons of interest with about 18 bases flanking the NNS codon. The polynucleotide sequences of the forward and reverse primers used to mutate the amino acids at positions 6, 30 and 32 are given in Table 1.

The QC reaction, amplification of the plasmid DNA, and transformation of *E. coli* cells were performed as described in Example 1(a). The subsequent transformation of *Bacillus subtilis* competent cells was also performed as described in Example 1(b). Supernatants from *Bacillus* cultures expressing proteases from modified or unmodified precursor were analyzed for protease activity using the AAPF assay as described in Example 1(c).

The results given in Tables 19, 20 and 21 show that most of the amino acid substitutions of amino acids at positions 6, 30 or 32 of the pro region of the P17 precursor protease lead to an enhanced production of the mature form of the protease (SEQ ID NO:17). In addition, site saturation of each of the substituted amino acids showed that each amino acid can be substituted by two or more amino acids at the same position to increase the production of the mature form relative to that obtained from the precursor protease having unmodified pro region.

TABLE 19

Effect of amino acid substitution at position 6 of the pro region on the production of the mature protease of SEQ ID NO: 17

| Mutation (Substitution) at position in pro region | Percent activity relative to activity from the unmodified precursor |
|---|---|
| E6 (control) | 100 |
| E6A | 152 |
| E6R | 231 |
| E6C | 172 |
| E6Q | 229 |
| E6G | 95 |
| E6H | 144 |
| E6I | 106 |
| E6L | 76 |
| E6K | 269 |

TABLE 19-continued

Effect of amino acid substitution at position 6 of the pro region on the production of the mature protease of SEQ ID NO: 17

| Mutation (Substitution) at position in pro region | Percent activity relative to activity from the unmodified precursor |
|---|---|
| E6M | 124 |
| E6F | 55 |
| E6P | 20 |
| E6S | 154 |
| E6T | 34 |
| E6W | 48 |
| E6Y | 114 |
| E6V | 55 |

TABLE 20

Effect of amino acid substitution at position 30 of the pro region on the production of the mature protease of SEQ ID NO: 17

| Mutation (Substitution) at position in pro region | Percent activity relative to activity from the unmodified precursor |
|---|---|
| E30 (control) | 100 |
| E30A | 190 |
| E30R | 152 |
| E30N | 122 |
| E30D | 106 |
| E30C | 89 |
| E30Q | 128 |
| E30G | 223 |
| E30H | 83 |
| E30I | 78 |
| E30L | 112 |
| E30M | 137 |
| E30P | 129 |
| E30S | 159 |
| E30T | 176 |
| E30W | 243 |
| E30Y | 130 |
| E30V | 131 |

TABLE 21

Effect of amino acid substitution at position 32 of the pro region on the production of the mature protease of SEQ ID NO: 17

| Mutation (Substitution) at position in pro region | Percent activity relative to activity from the unmodified precursor |
|---|---|
| A32 (control) | 100 |
| A32R | 142 |
| A32D | 81 |
| A32C | 170 |
| A32Q | 53 |
| A32E | 100 |
| A32G | 139 |
| A32L | 145 |
| A32K | 216 |
| A32F | 137 |
| A32P | 50 |
| A32S | 81 |
| A32T | 154 |
| A32Y | 277 |
| A32V | 146 |

(b) Site-Saturation Mutagenesis: Generation of Combinations of Two Substitutions in the Pro Region.

The plasmid expressing the E30G substitution in the pro region (SEQ ID NO:7) comprised in the full-length protease of SEQ ID NO:63 was subjected to a second round of site-saturation mutagenesis of the codon at position 6 to create a first library of polynucleotides that encode a full-length protease containing a substitution of amino acid 6 in combination with the E30G substitution of the pro region of the protease. The mutation at position 6 was created using the QuikChange® site-directed mutagenesis kit (QC; Stratagene) according to the directions provided by the manufacturer using forward and reverse primers of SEQ ID NOS:26 and 27, respectively. Similarly, a second library of polynucleotides was created to encode a full-length protease containing a substitution of amino acid 32 in combination with the E30G substitution in the pro region of the protease was created. The complementary overlapping forward GAGGCAAATGACG-GCGTCNNSATTCTCTCTGAGGAAGAG (SEQ ID NO:34) and reverse primers CTCTTCCTCA-GAGAGAATSNNGACGCCGTCATTTGCCTC (SEQ ID NO:35), were used for mutating the position 32.

The QC reaction, amplification of the plasmid DNA, and transformation of *E. coli* cells were performed as described in Example 1(a). The subsequent transformation of *Bacillus subtilis* competent cells was also performed as described in Example 1(b). Supernatants from *Bacillus* cultures expressing proteases from modified or unmodified precursor were analyzed for protease activity using the AAPF assay as described in Example 1(c).

Results shown in Tables 22 and 23 indicate that most substitutions of the amino acid at position 6 (Table 22) of the pro region of P17 when in combination with the substitution E30G further enhance the production of the mature form of the protease expressed from a polynucleotide encoding an unmodified pro region or a pro region containing the E30G substitution. Similarly, the results shown in Table 23 show that the combination of the E30G substitution with several substitutions at position 32 also further enhanced the production of the mature form of the protease expressed from a polynucleotide encoding an unmodified pro region or a pro region containing the E30G substitution.

TABLE 22

Effect of the combination of amino acid substitution E30G with substitutions of amino acid at position 6 of the pro region on the production of mature protease of SEQ ID NO: 17

| Mutation (Substitution) at positions in pro region | Percent activity relative to activity from the modified precursor E30G |
|---|---|
| E30G (control) | 100 |
| E6A-E30G | 106 |
| E6R-E30G | 136 |
| E6C-E30G | 157 |
| E6Q-E30G | 107 |
| E6G-E30G | 180 |
| E6H-E30G | 134 |
| E6L-E30G | 50 |
| E6K-E30G | 153 |
| E6M-E30G | 78 |
| E6P-E30G | 74 |
| E6S-E30G | 182 |
| E6T-E30G | 92 |
| E6W-E30G | 148 |
| E6Y-E30G | 33 |
| E6V-E30G | 69 |

TABLE 23

Effect of the combination of amino acid substitution E30G with substitutions of amino acid at position 32 of the pro region on the production of mature protease of SEQ ID NO: 17

| Mutation (Substitution) at positions in pro region | Percent activity relative to activity from the modified precursor E30G-A32 |
|---|---|
| E30G (control) | 100 |
| E30G-A32R | 188 |
| E30G-A32N | 94 |
| E30G-A32D | 69 |
| E30G-A32C | 38 |
| E30G-A32Q | 133 |
| E30G-A32E | 109 |
| E30G-A32G | 105 |
| E30G-A32H | 115 |
| E30G-A32I | 150 |
| E30G-A32L | 38 |
| E30G-A32K | 189 |
| E30G-A32P | 69 |
| E30G-A32S | 122 |
| E30G-A32T | 116 |
| E30G-A32W | 161 |
| E30G-A32Y | 13 |
| E30G-A32V | 110 |

(c) Site-Saturation Mutagenesis: Generation of Combinations of Three Substitutions in the Pro Region.

The plasmid expressing the combination of to substitutions E6G-E30G in the pro region comprised in the full-length protease of SEQ ID NO:63 was subjected to another round of site-saturation mutagenesis of the codon at position 32 to create a library of polynucleotides that encode a full-length protease containing a substitution of amino acid 32 in combination with the E6G-E30G combination of substitutions in the pro region of the protease. The mutation at position 32 was created using the QuikChange® site-directed mutagenesis kit (QC; Stratagene) according to the directions provided by the manufacturer using forward and reverse primers of SEQ ID NOS:34 and 35, respectively.

The QC reaction, amplification of the plasmid DNA, and transformation of *E. coli* cells were performed as described in Example 1(a). The subsequent transformation of *Bacillus subtilis* competent cells was also performed as described in Example 1(b). Supernatants from *Bacillus* cultures expressing proteases from modified or unmodified precursor were analyzed for protease activity using the AAPF assay as described in Example 1(c).

Results shown in Table 24 show that a triple substitution of amino acids at positions 6, 30 and 32 further enhance the production of the mature protease when processed from a pro region containing the two substitutions at positions 6 and 30. In particular, the A32E, A32S, A32T, and A32W when in combination with the E6G-E30G double substitution increase the production of the mature protease (SEQ ID NO:17) by about 73%, 3%, 33%, and 23%, respectively, relative to the level produced by the doubly mutated precursor comprising the E6G-E30G combination of substitutions. Considering that the E6G-E30G combination produces about 80% more mature than the single E30G substitution alone, the triple mutations E6G-E30G-A32E, E6G-E30G-A32S, E6G-E30G-A32T, and E6G-E30G-A32W can be calculated to produce 311%, 185%, 239% and 221%, respectively, of the level processed from the pro region containing the single E30G substitution.

TABLE 24

Effect of the combination of amino acid substitution E6G-E30G with substitution of amino acid at position 32 of the pro region on the production of mature protease of SEQ ID NO: 17

| Mutation (substitution) at positions in pro region | Percent activity E6G-E30G-A32X relative to activity from the modified precursor E6G-E30G |
| --- | --- |
| E6G-E30G (control) | 100 |
| E6G-E30G-A32R | 47 |
| E6G-E30G-A32N | 34 |
| E6G-E30G-A32D | 72 |
| E6G-E30G-A32C | 43 |
| E6G-E30G-A32Q | 87 |
| E6G-E30G-A32E | 173 |
| E6G-E30G-A32G | 58 |
| E6G-E30G-A32H | 88 |
| E6G-E30G-A32I | 21 |
| E6G-E30G-A32L | 34 |
| E6G-E30G-A32K | 69 |
| E6G-E30G-A32M | 88 |
| E6G-E30G-A32F | 90 |
| E6G-E30G-A32P | 100 |
| E6G-E30G-A32S | 102 |
| E6G-E30G-A32T | 133 |
| E6G-E30G-A32W | 123 |
| E6G-E30G-A32Y | 42 |
| E6G-E30G-A32V | 50 |

(d) Effect of Amino Acid Substitution(s) in the Pro Region of the Precursor Protease on the Production of the Mature Protease of SEQ ID NO:17 in Shake Flask Cultures.

To test the effect of amino acid substitutions in the pro region on the production of the mature protease of SEQ ID NO:17 in shake flask cultures, several of the *Bacillus subtilis* strains grown in the microtiter plates as described above and containing a substitution at position 30 in combination with a second substitution at position 6 or 32, and strains containing the combination of three substitutions in the pro region were grown for 48 hours as described in Example 1(e). Supernatant from the shake flask cultures was assayed for AAPF activity as described in Example 1(c).

The results for the activity in strains comprising the combination of two E6-E30G or E30G-A32, and three amino acid substitutions E6G-E30G-A32X are shown in Tables 25, 26 and 27, respectively. The results show that the enhancement of protease production obtained from modified precursor proteases in microtiter cultures is mimicked in shake flask cultures.

TABLE 25

Effect of the combination of amino acid substitution E30G with substitutions of amino acid at position 6 of the pro region of the mature protease of SEQ ID NO: 17 in shake flask cultures

| Mutation (substitution) at positions in pro region | Percent activity relative to activity of the modified precursor E30G |
| --- | --- |
| E6-E30G (control) | 100 |
| E6A-E30G | 115 |
| E6R-E30G | 131 |
| E6C-E30G | 91 |
| E6G-E30G | 142 |
| E6H-E30G | 150 |
| E6K-E30G | 81 |
| E6S-E30G | 111 |
| E6W-E30G | 145 |

TABLE 26

Effect of the combination of amino acid substitution E30G with substitutions of amino acid at position 32 of the pro region of the mature protease of SEQ ID NO: 17 in shake flask cultures

| Mutation (substitution) at positions in pro region | Percent activity relative to activity of the modified precursor E30G |
| --- | --- |
| E30G-A32 (control) | 100 |
| E30G-A32 | 101 |
| E30G-A32 | 121 |
| E30G-A32 | 157 |
| E30G-A32 | 165 |
| E30G-A32 | 158 |
| E30G-A32 | 108 |

TABLE 27

Effect of the combination of amino acid substitution E6G-E30G with substitutions at position 32 of the pro region of the mature protease of SEQ ID NO: 17 in shake flask cultures

| Mutation (substitution) at positions in pro region | Percent protease activity relative to activity from the modified precursor E6G-E30G |
| --- | --- |
| E6G-E30G-A32 (control precursor) | 100 |
| E6G-E30G-A32E | 142 |
| E6G-E30G-A32P | 76 |
| E6G-E30G-A32S | 98 |
| E6G-E30G-A32T | 106 |
| E6G-E30G-A32W | 135 |

EXAMPLE 5

The Effect of Mutations in the Pro Region of SEQ ID NO:7 on the Production of the Mature Alkaline Protease of SEQ ID NO:21

(a) Site-Saturation Mutagenesis of Amino Acids at Positions 6, 30 or 32 of the Pro Region Site-saturation mutagenesis of the pro region on the production of the mature protease of SEQ ID NO:21 was performed using the QuikChange® site-directed mutagenesis kit (QC; Stratagene) according to the directions of the manufacturer. A DNA cassette comprising the AprE promoter, and the polynucleotide that encodes the full-length protease of SEQ ID NO:21 was cloned into the EcoRI and HindIII restriction sites of the pBN3 vector (Babe et al., Appl. Biochem. 27: 117-124 [1998]). pBN3 (FIG. 4B) to generate the pBN3-P21 plasmid. The P21 DNA cassette comprised the *B. subtilis* aprE promoter gaattcctccattttcttctgctat-caaaataacagactcgtgattttc-caaacgagctttcaaaaaagcctctgccccttgcaaatcg gatgcctgtc-tataaaattcccgatattggttaaacagcggcgcaatggcggccgcatctgatgtctt tgcttggcgaatgttcatctt atttcttcctccctctcaataattUt-tcattctatccatttctgtaaagtt-tattttcagaatactttatcatcatgctttgaaaaaatatcac gataatatccattgt-tctcacggaagcacacgcaggtcatttgaacgaattUttcgacaggaatttgccgg gactcaggagcattta acctaaaaaagcatgacatttcagcat-aatgaacatttactcatgtc-tattttcgttcttttctgtatgaaaatagttatttcgagtctctac ggaaatagc-gagagatgatatacctaaatagagataaaatcatctcaaaaaaatgggtctactaaa atattattccatctattaca ataaattcacagaatagtatttaag-taagtctactctgaatttttttaaaaggagagggtaaaga (SEQ ID NO:1), the polynucleotide sequence gtgagaagcaaaaaattgtggatcagct-tgttgtttgcgttaacgttaatcttttacgatggcgttcagcaacatgtctgcgcaggct (SEQ ID NO:2), which encodes the AprE signal peptide VRSKKLWISLLFALTLIFTMAFSNMSAQA (SEQ ID NO:3), the polynucleotide sequence gctgaagaagcaaaa-gaaaaatatttaattggctttaatgag-caggaagctgtcagtgagtttgtagaacaagtagaggcaaat gacgaggtcgc-cattctctctgaggaagaggaagtcgaaattgaattgcttcatgaatttgaaacgattc ctgttttatccgttgagtt aagcccagaagatgtggacgcgct-tgaactcgatccagcgatttcttatattgaagaggatgcagaagtaacgacaatg (SEQ ID NO:6), which encodes the unmodified pro region AEEAKEKYLIGFNEQEAVSEFVEQVEAN-DEVAILSEEEEVEIELLHEFETIPVLSVELSPEDVD ALELDPAISYIEEDAEVTTM (SEQ ID NO:7), and the polynucleotide sequence GCGCAATCAGTGCCATGGG-GAATTAGCCGTGTGCAAGCCCCAGCTGC-CCATAACCGTG GATTGACAGGTTCTGGTG-TAAAAGTTGCTGTCCTCGATACAGGTATTTCCACTC ATCCA GACTTAAATATTCGTGGTG-GCGCTAGCTTTGTACCAGGGGAACCATC-CACTCAAGATGG GAATGGGCATGGCACGCATGTG-GCCGGGACGATTGCTGCTTTAGACAATTCGATTGGC GTTCTTGGCGTAGCGCCGAGAGCGGAAC-TATACGCTGTTAAAGTATTAGGGGCGAGCG GTTCAGGTTCGGTCAGCTCGATTGC-CCAAGGATTGGAATGGGCAGGGAACAATCGTAT GCACGTTGCTAATTTGAGTTTAGGACTG-CAGGCACCAAGTGCCACACTTGAGCAAGCT GTTAATAGCGCGACTTCTAGAGGCGT-TCTTGTTGTAGCGGCATCTGGAAATTCAGGTGC AGGCTCAATCAGCTATCCGGCCCGTTAT-GCGAACGCAATGGCAGTCGGAGCTACTGAC CAAAACAACAACCGCGCCAGCTTTTCA-CAGTATGGCGCAGGGCTTGACATTGTCGCAC CAG-GTGTAAACGTGCAGAGCACATACCCAG-GTTCAACGTATGCCAGCTTAAACGGTAC ATCGATGGCTACTCCTCATGTTGCAGGT-GCAGCAGCCCTTGTTAAACAAAAGAACCCAT CTTGGTCCAATGTACAAATCCGCAAT-CATCTAAAGAATACGGCAACGAGCTTAGGAAGC ACGAACTTGTATGGAAGCGGACTTGT-CAATGCAGAAGCTGCAACTCGT (SEQ ID NO:20), which encodes the mature region of protease 21 (P21). AQS-VPWGISRVQAPAAHNRGLTGSGVKVAV-LDTGISTHPDLNIRGGASFVPGEPSTQDGN GHGTH-VAGTIAALDNSIGVLGVAPRAELYAVKVLGASGSGSV SSIAQGLEWAGNNRMHVA NLSLGLQAPS-ATLEQAVNSATSRGVLVVAASGNSGAG-SISYPARYANAMAVGATDQNNNR ASFSQYG-AGLDIVAPGVNVQSTYPGSTYASLNGTSMATPHVAG AAALVKQKNPSWSNVQI RNHLKNTATSLGST-NLYGSGLVNAEAATR (SEQ ID NO:21).

Each of the 3 codons in the pro region of SEQ ID NO:7, exemplified by NNG/C, comprised in the full-length protease of SEQ ID NO:65, were mutated to be substituted by the 32 possible nucleotide triplets that encode the 20 naturally occurring amino acids to generate three libraries as follows. An aliquot of plasmid pJH-P21 DNA comprising the sequence encoding the full-length protease was mutated to generate a first library of clones encoding all possible substitutions of glutamic acid (E) at position 6 (E6X) of the pro region (SEQ ID NO:7); a second aliquot was mutated to generate a second library of clones encoding all possible substitutions of glutamic acid (E) at position 30 (E30X) of the pro region (SEQ ID NO:7); and a third aliquot was mutated to generate a third library of clones encoding all possible substitutions of arginine (A) at position 32 (A32X) of the pro region (SEQ ID NO:7). Complementary overlapping primers were designed for mutating the codons of interest with about 18 bases flanking the NNS codon. The polynucleotide sequences of the forward and reverse primers used to mutate the amino acids at positions 6, 30 and 32 are given in Table 1.

The QC reaction, amplification of the plasmid DNA, and transformation of E. coli cells were performed as described in Example 1(a). The subsequent transformation of Bacillus subtilis competent cells was also performed as described in Example 1(b). Supernatants from Bacillus cultures expressing proteases from modified or unmodified precursor were analyzed for protease activity using the AAPF assay as described in Example 1(c).

The results given in Tables 28, 29, and 30 showed that all but one of the amino acid substitutions of amino acids at positions 6 of the pro region of the precursor protease lead to an enhanced production of the mature form of the protease of SEQ ID NO:21, whereas all but one of the amino acid substitutions at positions 30 or 32 showed similar or diminished protease production when compared to the production of the mature protease when processed from an unmodified pro region. In addition, site saturation of each of the substituted amino acids showed that each amino acid can be substituted by two or more amino acids at the same position to increase the production of the mature form relative to that obtained from the precursor protease having unmodified pro region.

TABLE 28

Effect of amino acid substitution at position 6 of the pro region on the production of the mature protease of SEQ ID NO: 21

| Mutation (Substitution) at position in pro region | Percent activity relative to activity from the unmodified precursor |
|---|---|
| E6 (control) | 100 |
| E6A | 84 |
| E6R | 85 |
| E6D | 57 |
| E6C | 90 |
| E6Q | 93 |
| E6G | 96 |
| E6H | 86 |
| E6I | 76 |
| E6L | 85 |
| E6K | 84 |
| E6M | 73 |
| E6P | 63 |
| E6S | 93 |
| E6T | 94 |
| E6W | 40 |
| E6Y | 74 |
| E6V | 94 |

TABLE 29

Effect of amino acid substitution at position 30 of the pro region on the production of the mature protease of SEQ ID NO: 21

| Mutation (Substitution) at position in pro region | Percent activity relative to activity from the unmodified precursor |
|---|---|
| E30 (control) | 100 |
| E30A | 110 |
| E30R | 102 |
| E30N | 129 |
| E30D | 115 |
| E30C | 108 |
| E30Q | 87 |
| E30G | 130 |
| E30H | 123 |
| E30I | 47 |
| E30L | 83 |
| E30M | 129 |
| E30F | 116 |
| E30P | 50 |
| E30S | 134 |

TABLE 29-continued

Effect of amino acid substitution at position 30 of the pro region on the production of the mature protease of SEQ ID NO: 21

| Mutation (Substitution) at position in pro region | Percent activity relative to activity from the unmodified precursor |
|---|---|
| E30T | 94 |
| E30W | 125 |
| E30V | 74 |

TABLE 30

Effect of amino acid substitution at position 32 of the pro region on the production of the mature protease of SEQ ID NO: 21

| Mutation (Substitution) at positions in pro region | Percent activity relative to activity from the unmodified precursor |
|---|---|
| A32 (unmodified pro; control) | 100 |
| A32R | 95 |
| A32N | 70 |
| A32D | 63 |
| A32C | 85 |
| A32Q | 67 |
| A32G | 70 |
| A32H | 76 |
| A32L | 116 |
| A32M | 97 |
| A32F | 125 |
| A32P | 64 |
| A32S | 68 |
| A32T | 61 |
| A32V | 116 |

Site-Saturation Mutagenesis: Generation of Combinations of Substitutions in the Pro Region of SEQ ID NO:21.

The plasmid expressing the E30S substitution in the pro region (SEQ ID NO:7) second round of site-saturation mutagenesis of the codon at position 6 to create a first library of polynucleotides that encode a full-length protease containing a substitution of amino acid 6 in combination with the E30S substitution of the pro region of the protease. The mutation at position 6 was created using the QuikChange® site-directed mutagenesis kit (QC; Stratagene) according to the directions provided by the manufacturer using forward and reverse primers of SEQ ID NOS:26 and 27, respectively (Table 1). Similarly, a second library of polynucleotides was created to encode a full-length protease containing a substitution of amino acid 32 in combination with the E30S substitution in the pro region of the protease was created. The complementary overlapping forward primers used to create the library of mutated polynucleotides comprising the A32X mutation in combination with the E30S substitution, were the complementary forward GAGGCAAATGACTCG-GTCNNSATTCTCTCTGAGGAAGAG:SEQ ID NO:36, and reverse primer CTCTTCCTCAGAGAGAATSNNGAC-CGAGTCATTTGCCTC SEQ ID NO:37.

The QC reaction, amplification of the plasmid DNA, and transformation of E. coli cells were performed as described in Example 1(a). The subsequent transformation of Bacillus subtilis competent cells was also performed as described in Example 1(b). Supernatants from Bacillus cultures expressing proteases from modified or unmodified precursor were analyzed for protease activity using the AAPF assay as described in Example 1(c).

Results shown in Tables 31 and 32 indicate that most substitutions of the amino acid at position 6 (Table 31) of the pro region when in combination with the substitution E30S further enhance the production of the mature form of the protease expressed from a polynucleotide encoding an unmodified pro region or a pro region containing the single E30S substitution. Similarly, most substitutions of amino acid at position 32 of the pro region when in combination with the substitution E30S at site 30, also lead to a further enhancement of production of the mature form of the protease.

TABLE 31

Effect of the combination of amino acid substitution E30S with substitutions of amino acid at position 6 of the pro region on the production of mature protease of SEQ ID NO: 21

| Mutation (Substitution) at positions in pro region | Percent activity relative to activity from the modified precursor E6-E30S |
|---|---|
| E6-E30S (control, modified) | 100 |
| E6A-E30S | 116 |
| E6N-E30S | 64 |
| E6Q-E30S | 82 |
| E6G-E30S | 119 |
| E6H-E30S | 86 |
| E6I-E30S | 88 |
| E6L-E30S | 162 |
| E6K-E30S | 107 |
| E6F-E30S | 156 |
| E6P-E30S | 150 |
| E6S-E30S | 99 |
| E6T-E30S | 74 |
| E6W-E30S | 88 |
| E6Y-E30S | 162 |
| E6V-E30S | 101 |

TABLE 32

Effect of the combination of amino acid substitution E30S with substitutions of amino acid at position 32 of the pro region on the production of mature protease of SEQ ID NO: 21

| Mutation (substitution) at positions in pro region | Percent activity relative to activity from the modified precursor E30S-A32 |
|---|---|
| E30S, A32 (control, modified) | 100 |
| E30S-A32R | 113 |
| E30S-A32N | 177 |
| E30S-A32D | 229 |
| E30S-A32C | 112 |
| E30S-A32Q | 195 |
| E30S-A32E | 148 |
| E30S-A32G | 194 |
| E30S-A32H | 204 |
| E30S-A32L | 223 |
| E30S-A32K | 180 |
| E30S-A32M | 181 |
| E30S-A32F | 171 |
| E30S-A32P | 250 |
| E30S-A32S | 205 |
| E30S-A32T | 166 |
| E30S-A32W | 202 |
| E30S-A32Y | 116 |
| E30S-A32V | 141 |

We claim:

1. An isolated modified polynucleotide encoding a modified protease, said isolated modified polynucleotide comprising a first polynucleotide encoding a signal peptide, said first polynucleotide being operably linked to a second polynucleotide encoding the pro region set forth in SEQ ID NO:7, wherein said pro region comprises a substitution selected from the group consisting of: E6A, E6C, E6F, E6L, E6P, E6T, E6W, E6Y, E30A, E30I, E30L, E30P, E30T, E30V, E30Y, A32C, A32E, A32G, A32K, A32Q, A32S, and A32T, said second polynucleotide being operably linked to a third polynucleotide encoding the mature region of a protease that is at least 90% identical to the mature protease of SEQ ID NO: 9, wherein said substitutions enhance the production of said mature protease by a Bacillus sp. host cell.

2. The isolated modified polynucleotide of claim 1, wherein said mature protease is a wild-type or variant alkaline serine protease derived from Bacillus clausii or Bacillus lentus.

3. The isolated polynucleotide of claim 1, wherein said signal peptide has an amino acid sequence chosen from SEQ ID NOS:3 and 5.

4. An expression vector comprising the isolated modified polynucleotide of claim 1.

5. A Bacillus sp. host cell comprising the expression vector of claim 4.

6. The host cell of claim 5, wherein said host cell is a B. subtilis host cell.

7. A method for producing a mature protease in a Bacillus sp. host cell, said method comprising:
a) providing the expression vector of claim 4;
b) transforming a Bacillus sp. host cell with said expression vector; and
c) culturing said host cell under suitable conditions such that said protease is produced by said host cell.

8. The method of claim 7, wherein said Bacillus sp. host cell is a Bacillus subtilis host cell.

9. The method of claim 7, wherein said mature protease is a wild-type Bacillus clausii or a Bacillus lentus alkaline serine protease, variant or homolog thereof.

10. The method of claim 7, wherein said signal peptide has the amino acid sequence of SEQ ID NO:3, wherein said pro region comprises a substitution chosen from E6A, E6C, E6F, E6P, E6T, E6W, A32K, and A32T, and wherein said mature protease comprises SEQ ID NO:9.

11. The method of claim 7, wherein said signal peptide has the amino acid sequence of SEQ ID NO:3, wherein said pro region comprises a substitution of an amino acid chosen from E6A, E6C, E6Y, E30A, E30L, E30P, E30T, E30Y, E30V, A32C, A32E, A32G, A32K, and, and wherein said mature protease comprises SEQ ID NO:17.

12. The method of claim 7, wherein said signal peptide has the amino acid sequence of SEQ ID NO:3, wherein said pro region comprises a substitution of an amino acid chosen from E6A, E30A, E30L, E30T and E30V, and wherein said mature protease comprises SEQ ID NO:19.

13. The method of claim 7, wherein said signal peptide has the amino acid sequence of SEQ ID NO:3, wherein said pro region comprises an E30A substitution, and wherein said mature protease comprises SEQ ID NO:21.

14. The isolated polynucleotide of claim 1, wherein said first polynucleotide encodes the signal peptide of SEQ ID NO:3, wherein said pro region comprises a substitution of an amino acid chosen from E6A, E6C, E6Y, E30A, E30L, E30P, E30T, E30Y, E30V, A32C, A32E, A32G, A32K, and A32T, and wherein said mature protease comprises SEQ ID NO:17.

15. The isolated polynucleotide of claim 1, wherein said first polynucleotide encodes the signal peptide of SEQ ID NO:3, wherein said pro region comprises a substitution of an amino acid chosen from E6A, E6C, E6F, E6P, E6T, E6W, A32K, and A32T, and wherein said mature protease comprises SEQ ID NO:9.

16. The isolated polynucleotide of claim 1, wherein said first polynucleotide encodes the signal peptide of SEQ ID NO:3, wherein said pro region comprises a substitution of an amino acid chosen from E6A, E30A, E30L, E30T and E30V, and wherein said mature protease comprises SEQ ID NO:19.

17. The isolated polynucleotide of claim 1, wherein said first polynucleotide encodes the signal peptide of SEQ ID NO:3, wherein said pro region comprises a substitution of an amino acid chosen from E6A, E6L, E6F, E6T, E30I, E30L, E30P, E30T, E30Y, E30V, A32Q, A32S and A32T, and wherein said mature protease comprises SEQ ID NO:11.

18. The isolated polynucleotide of claim 1, wherein said first polynucleotide encodes the signal peptide of SEQ ID NO:3, wherein said pro region comprises the amino acid substitution E30A, and wherein said mature protease comprises SEQ ID NO:21.

19. The method of claim 7, wherein said signal peptide has the amino acid sequence of SEQ ID NO:3, wherein said pro region comprises a substitution of an amino acid chosen from E6A, E6L, E6F, E6T, E30I, E30L, E30P, E30T, E30Y, E30V, A32Q, A32S and A32T, and wherein said mature protease comprises SEQ ID NO:11.

* * * * *

SEQUENCE LISTING

<160> NUMBER OF SEQ ID NOS: 68

<210> SEQ ID NO 1
<211> LENGTH: 609
<212> TYPE: DNA
<213> ORGANISM: Bacillus subtilis

<400> SEQUENCE: 1

```
gaattcctcc attttcttct gctatcaaaa taacagactc gtgattttcc aaacgagctt      60
tcaaaaaagc ctctgcccct tgcaaatcgg atgcctgtct ataaaattcc cgatattggt     120
taaacagcgg cgcaatggcg gccgcatctg atgtctttgc ttggcgaatg ttcatcttat     180
ttcttcctcc ctctcaataa ttttttcatt ctatcccttt tctgtaaagt ttattttttca    240
gaatactttt atcatcatgc tttgaaaaaa tatcacgata atatccattg ttctcacgga     300
agcacacgca ggtcatttga acgaattttt tcgacaggaa tttgccggga ctcaggagca     360
tttaacctaa aaaagcatga catttcagca taatgaacat ttactcatgt ctattttcgt     420
tcttttctgt atgaaaatag ttatttcgag tctctacgga aatagcgaga gatgatatac     480
ctaaatagag ataaaatcat ctcaaaaaaa tgggtctact aaaatattat tccatctatt     540
acaataaatt cacagaatag tcttttaagt aagtctactc tgaattttt taaaaggaga     600
gggtaaaga                                                              609
```

<210> SEQ ID NO 2
<211> LENGTH: 87
<212> TYPE: DNA
<213> ORGANISM: Bacillus subtilis

<400> SEQUENCE: 2

```
gtgagaagca aaaaattgtg gatcagcttg ttgtttgcgt taacgttaat ctttacgatg      60
gcgttcagca acatgtctgc gcaggct                                           87
```

<210> SEQ ID NO 3
<211> LENGTH: 29
<212> TYPE: PRT
<213> ORGANISM: Bacillus subtilis

<400> SEQUENCE: 3

Val Arg Ser Lys Lys Leu Trp Ile Ser Leu Leu Phe Ala Leu Thr Leu
1               5                   10                  15

Ile Phe Thr Met Ala Phe Ser Asn Met Ser Ala Gln Ala
            20                  25

<210> SEQ ID NO 4
<211> LENGTH: 81
<212> TYPE: DNA
<213> ORGANISM: Artificial
<220> FEATURE:
<223> OTHER INFORMATION: synthetic sequence encoding fusion signal
      peptide

<400> SEQUENCE: 4

```
gtgagaagca aaaaattgtg gatcgtcgcg tcgaccgcac tactcatttc tgttgctttt      60
agttcatcga tcgcatcggc t                                                 81
```

<210> SEQ ID NO 5
<211> LENGTH: 27
<212> TYPE: PRT
<213> ORGANISM: Artificial
<220> FEATURE:

<223> OTHER INFORMATION: synthetic fusion signal peptide

<400> SEQUENCE: 5

Val Arg Ser Lys Lys Leu Trp Ile Val Ala Ser Thr Ala Leu Leu Ile
1               5                   10                  15

Ser Val Ala Phe Ser Ser Ser Ile Ala Ser Ala
            20                  25

<210> SEQ ID NO 6
<211> LENGTH: 252
<212> TYPE: DNA
<213> ORGANISM: Bacillus clausii

<400> SEQUENCE: 6
gctgaagaag caaaagaaaa atatttaatt ggctttaatg agcaggaagc tgtcagtgag      60
tttgtagaac aagtagaggc aaatgacgag gtcgccattc tctctgagga agaggaagtc    120
gaaattgaat tgcttcatga atttgaaacg attcctgttt tatccgttga gttaagccca    180
gaagatgtgg acgcgcttga actcgatcca gcgatttctt atattgaaga ggatgcagaa    240
gtaacgacaa tg                                                        252

<210> SEQ ID NO 7
<211> LENGTH: 84
<212> TYPE: PRT
<213> ORGANISM: Bacillus clausii

<400> SEQUENCE: 7

Ala Glu Glu Ala Lys Glu Lys Tyr Leu Ile Gly Phe Asn Glu Gln Glu
1               5                   10                  15

Ala Val Ser Glu Phe Val Glu Gln Val Glu Ala Asn Asp Glu Val Ala
            20                  25                  30

Ile Leu Ser Glu Glu Glu Val Glu Ile Glu Leu Leu His Glu Phe
        35                  40                  45

Glu Thr Ile Pro Val Leu Ser Val Glu Leu Ser Pro Glu Asp Val Asp
    50                  55                  60

Ala Leu Glu Leu Asp Pro Ala Ile Ser Tyr Ile Glu Glu Asp Ala Glu
65                  70                  75                  80

Val Thr Thr Met

<210> SEQ ID NO 8
<211> LENGTH: 807
<212> TYPE: DNA
<213> ORGANISM: Bacillus lentus

<400> SEQUENCE: 8
gcgcaatcag tgccatgggg aattagccgt gtgcaagccc agctgcccaa taaccgtgga     60
ttgacaggtt ctggtgtaaa agttgctgtc ctcgatacag gtatttccac tcatccagac   120
ttaaatattc gtggtggcgc tagctttgta ccagggggaac catccactca agatgggaat   180
gggcatggca cgcatgtggc cgggacgatt gctgctttaa caattcgat tggcgttctt    240
ggcgtagcgc cgagcgcgga actatacgct gttaaagtat taggggcgag cggttcaggt   300
tcggtcagct cgattgccca aggattggaa tgggcaggga caatggcat gcacgttgct    360
aatttgagtt taggaagccc ttcgccaagt gccacacttg agcaagctgt taatagcgcg   420
acttctagag gcgttcttgt tgtagcggca tctggaaatt caggtgcagg ctcaatcagc   480
tatccggccc gttatgcgaa cgcaatggca gtcggagcta ctgaccaaaa caacaaccgc    540

```
gccagctttt cacagtatgg cgcagggctt gacattgtcg caccaggtgt aaacgtgcag    600
agcacatacc caggttcaac gtatgccagc ttaaacggta catcgatggc tactcctcat    660
gttgcaggtg cagcagccct tgttaaacaa aagaacccat cttggtccaa tgtacaaatc    720
cgcaatcatc taaagaatac ggcaacgagc ttaggaagca cgaacttgta tggaagcgga    780
cttgtcaatg cagaagctgc aactcgt                                       807
```

<210> SEQ ID NO 9
<211> LENGTH: 269
<212> TYPE: PRT
<213> ORGANISM: Bacillus lentus

<400> SEQUENCE: 9

```
Ala Gln Ser Val Pro Trp Gly Ile Ser Arg Val Gln Ala Pro Ala Ala
1               5                   10                  15

```
gcgcaatcag tgccatgggg aattagccgt gtgcaagccc cagctgccca taaccgtgga        60
ttgacaggtt ctggtgtaaa agttgctgtc ctcgatacag gtatttccac tcatccagac       120
ttaaatattc gtggtggcgc tagctttgta ccaggggaac catccactca agatgggaat       180
gggcatggca cgcatgtggc cgggacgatt gctgctctag acaattcgat tggcgttctt       240
ggcgtagcgc cgagcgcgga actatacgct gttaaagtat taggggcgag cggttcaggc       300
gccatcagct cgattgccca aggattggaa tgggcaggga caatggcat gcacgttgct        360
aatttgagtt taggaagccc ttcgccaagt gccacacttg agcaagctgt aatagcgcg        420
acttctagag gcgttcttgt tgtagcggca tctggaaatt caggtgcagg ctcaatcagc       480
tatccggccc gttatgcgaa cgcaatggca gtcggagcta ctgaccaaaa caacaaccgc       540
gccagctttt cacagtatgg cgcagggctt gacattgtcg caccaggtgt aaacgtgcag       600
agcacatacc caggttcaac gtatgccagc ttaaacggta catcgatggc tactcctcat       660
gttgcaggtg cagcagccct tgttaaacaa aagaacccat cttggtccaa tgtacaaatc       720
cgcaatcatc taaagaatac ggcaacgagc ttaggaagca cgaacttgta tggaagcgga       780
cttgtcaatg cagaagctgc aactcgt                                           807

<210> SEQ ID NO 11
<211> LENGTH: 269
<212> TYPE: PRT
<213> ORGANISM: Artificial
<220> FEATURE:
<223> OTHER INFORMATION: synthetic Bacillus lentus variant

<400

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
            245                 250                 255

Tyr Gly Ser Gly Leu Val Asn Ala Glu Ala Ala Thr Arg
            260                 265

<210> SEQ ID NO 12
<211> LENGTH: 807
<212> TYPE: DNA
<213> ORGANISM: Bacillus clausii

<400> SEQUENCE: 12

| | | | | | |
|---|---|---|---|---|---|
| gcgcaatcag | tgccatgggg | aattagccgt | gtgcaagccc | cagctgccca | taaccgtgga | 60 |
| ttgacaggtt | ctggtgtaaa | agttgctgtc | ctcgatacag | gtatttccac | tcatccagac | 120 |
| ttaaatattc | gtggtggcgc | tagctttgta | ccagggaaac | catccactca | agatgggaat | 180 |
| gggcatggca | cgcatgtggc | tgggacgatt | gctgctttaa | acaattcgat | tggcgttctt | 240 |
| ggcgtagcac | cgaacgcgga | actatacgct | gttaaagtat | taggggcgag | cggttcaggt | 300 |
| tcggtcagct | cgattgccca | aggattggaa | tgggcaggga | acaatggcat | gcacgttgct | 360 |
| aatttgagtt | taggaagccc | ttcgccaagt | gccacacttg | agcaagctgt | taatagcgcg | 420 |
| acttctagag | gcgttcttgt | tgtagcggca | tctgggaatt | caggtgcagg | ctcaatcagc | 480 |
| tatccggccc | gttatgcgaa | cgcaatggca | gtcggagcta | ctgaccaaaa | caacaaccgc | 540 |
| gccagctttt | cacagtatgg | cgcagggctt | gacattgtcg | caccaggtgt | aaacgtgcag | 600 |
| agcacatacc | caggttcaac | gtatgccagc | ttaaacggta | tcgatggc | tactcctcat | 660 |
| gttgcaggtg | cagcagccct | tgttaaacaa | aagaacccat | cttggtccaa | tgtacaaatc | 720 |
| cgcaatcatc | taaagaatac | ggcaacgagc | ttaggaagca | cgaacttgta | tggaagcgga | 780 |
| cttgtcaatg | cagaagcggc | aacacgc | | | | 807 |

<210> SEQ ID NO 13
<211> LENGTH: 269
<212> TYPE: PRT
<213> ORGANISM: Bacillus clausii

<400> SEQUENCE: 13

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Asn Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

<210> SEQ ID NO 14
<211> LENGTH: 807
<212> TYPE: DNA
<213> ORGANISM: Artificial
<220> FEATURE:
<223> OTHER INFORMATION: synthetic sequence encoding Bacillus clausii
      variant

<400> SEQUENCE: 14
gcgcaatcgg taccatgggg aattagccgt gtgcaagccc cagctgccca taaccgtgga      60
ttgacaggtt ctggtgtaaa agttgctgtc ctcgatacag gtatttccac tcatccagac     120
ttaaatattc gtggtggcgc tagctttgta ccaggggaac catccactca agatgggaat     180
gggcatggca cgcatgtggc tgggacgatt gctgctttaa caattcgat ggcgttctt      240
ggcgtagcac cgaacgcgga actatacgct gttaaagtat taggggcgag cggttcaggt     300
tcggtcagct cgattgccca aggattggaa tgggcaggga caatgttat gcacgttgct      360
aatttgagtt taggactgca ggcaccaagt gccacacttg agcaagctgt aatagcgcg      420
acttctagag gcgttcttgt tgtagcggca tctgggaatt caggtgcagg ctcaatcagc     480
tatccggccc gttatgcgaa cgcaatggca gtcggagcta ctgaccaaaa caacaaccgc     540
gccagctttt cacagtatgg cgcagggctt gacattgtcg caccaggtgt aaacgtgcag     600
agcacatacc caggttcaac gtatgccagc ttaaacggta tcgatggc tactcctcat      660
gttgcaggtg cagcagccct tgttaaacaa aagaacccat cttggtccaa tgtacaaatc     720
cgcaatcatc taaagaatac ggcaacgagc ttaggaagca cgaacttgta tggaagcgga     780
cttgtcaatg cagaagcggc aacacgt                                        807

<210> SEQ ID NO 15
<211> LENGTH: 269
<212> TYPE: PRT
<213> ORGANISM: Artificial
<220> FEATURE:
<223> OTHER INFORMATION: synthetic Bacillus clausii variant

<400> SEQUENCE: 15

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
         20                  25                  30

Thr Gly Ile Ser Thr His Pro Asp Leu Asn Ile Arg Gly Gly Ala Ser
         35                  40                  45

Phe Val Pro Gly Glu Pro Ser Thr Gln Asp Gly Asn Gly His Gly Thr
 50                  55                  60

His Val Ala Gly Thr Ile Ala Ala Leu Asn Asn Ser Ile Gly Val Leu
65                  70                  75                  80

Gly Val Ala Pro Asn Ala Glu Leu Tyr Ala Val Lys Val Leu Gly Ala
                 85                  90                  95

Ser Gly Ser Gly Ser Val Ser Ser Ile Ala Gln Gly Leu Glu Trp Ala
             100                 105                 110

Gly Asn Asn Val Met His Val Ala Asn Leu Ser Leu Gly Leu Gln Ala
         115                 120                 125

Pro Ser Ala Thr Leu Glu Gln Ala Val Asn Ser Ala Thr Ser Arg Gly
130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                 165                 170                 175

Asn Asn Asn Arg Ala Ser Phe Ser Gln Tyr Gly Ala Gly Leu Asp Ile
             180                 185                 190

Val Ala Pro Gly Val Asn Val Gln Ser Thr Tyr Pro Gly Ser Thr Tyr
         195                 200                 205

Ala Ser Leu Asn Gly Thr Ser Met Ala Thr Pro His Val Ala Gly Ala
210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                 245                 250                 255

Tyr Gly Ser Gly Leu Val Asn Ala Glu Ala Ala Thr Arg
             260                 265

<210> SEQ ID NO 16
<211> LENGTH: 807
<212> TYPE: DNA
<213> ORGANISM: Artificial
<220> FEATURE:
<223> OTHER INFORMATION: synthetic sequence encoding Bacillus clausii
      variant

<400> SEQUENCE: 16
gcgcaatcgg taccatgggg aattagccgt gtgcaagccc cagctgccca taaccgtgga     60
ttgacaggtt ctggtgtaaa agttgctgtc ctcgatacag gtatttccac tcatccagac    120
ttaaatattc gtggtggcgc tagctttgta ccaggggaac catccactca agatgggaat    180
gggcatggca cgcatgtggc tgggacgatt gctgctttaa acaattcgat tggcgttctt    240
ggcgtagcac cgaacgcgga actatacgct gttaaagtat taggggcgag cggtatgggt    300
tcggtcagct cgattgccca aggattggaa tgggcaggga caatgttat gcacgttgct    360 aatttgagtt taggactgca ggcaccaagt gccacacttg agcaagctgt taatagcgcg    420
acttctagag gcgttcttgt tgtagcggca tctggcaatt caggtgcagg ctcaatcagc    480
tatccggccc gttatgcgaa cgcaatggca gtcggagcta ctgaccaaaa caacaaccgc    540
gccagctttt cacagtatgg cgcagggctt gacattgtcg caccaggtgt aaacgtgcag    600
agcacatacc caggttcaac gtatgccagc ttaaacggta catcgatggc tactcctcat     660
gttgcaggtg cagcagccct tgttaaacaa aagaacccat cttggtccaa tgtacaaatc     720
cgcaatcatc taaagaatac ggcaacgagc ttaggaagca cgaacttgta tggaagcgga     780
cttgtcaatg cagaagcggc aacacgt                                          807

<210> SEQ ID NO 17
<211> LENGTH: 269
<212> TYPE: PRT
<213> ORGANISM: Artificial
<220> FEATURE:
<223> OTHER INFORMATION: synthetic Bacillus clausii variant

<400> SEQUENCE: 17

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
        50                  55                  60

His Val Ala Gly Thr Ile Ala Ala Leu Asn Asn Ser Ile Gly Val Leu
65                  70                  75                  80

Gly Val Ala Pro Asn Ala Glu Leu Tyr Ala Val Lys Val Leu Gly Ala
                85                  90                  95

Ser Gly Met Gly Ser Val Ser Ser Ile Ala Gln Gly Leu Glu Trp Ala
            100                 105                 110

Gly Asn Asn Val Met His Val Ala Asn Leu Ser Leu Gly Leu Gln Ala
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

<210> SEQ ID NO 18
<211> LENGTH: 807
<212> TYPE: DNA
<213> ORGANISM: Artificial
<220> FEATURE:
<223> OTHER INFORMATION: synthetic sequence encoding Bacillus clausii
      variant

<400> SEQUENCE: 18

```
gcgcaatcgg taccatgggg aattagccgt gtgcaagccc cagctgccca taaccgtgga    60
ttgacaggtt ctggtgtaaa agttgctgtc ctcgatacag gtatttccac tcatccagac   120
ttaaatattc gtggtggcgc tagttttgta ccaggggaac catccactca agatgggaat   180
gggcatggca cgcatgtggc tgggacgatt gctgctttaa acaattcgat tggcgttctt   240
ggcgtagcac cgaacgcgga actatacgct gttaaagtat taggggcgag cggtggcggt   300
tcgaacagct cgattgccca aggattggaa tgggcaggga acaatggcat gcacgttgct   360
aatttgagtt taggaagccc ttcgccaagt gccacacttg agcaagctgt aatagcgcg    420
acttctagag gcgttcttgt tgtagcggca tctggcaatt caggtgcagg ctcaatcagc   480
tatccggccc gttatgcgaa cgcaatggca gtcggagcta ctgaccaaaa caacaaccgc   540
gccagctttt cacagtatgg cgcagggctt gacattgtcg caccaggtgt aaacgtgcag   600
agcacatacc caggttcaac gtatgccagc ttaaacggta catcgatggc tactcctcat   660
gttgcaggtg cagcagccct tgttaaacaa aagaacccat cttggtccaa tgtacaaatc   720
cgcaatcatc taaagaatac ggcaacgagc ttaggaagca cgaacttgta tggaagcgga   780
cttgtcaatg cagaagcggc aacacgt                                       807
```

<210> SEQ ID NO 19
<211> LENGTH: 269
<212> TYPE: PRT
<213> ORGANISM: Artificial
<220> FEATURE:
<223> OTHER INFORMATION: synthetic Bacillus clausii variant

<400> SEQUENCE: 19

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Asn Ala Glu Leu Tyr Ala Val Lys Val Leu Gly Ala
                85                  90                  95

Ser Gly Gly Gly Ser Asn Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
```

```
Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

```
<210> SEQ ID NO 20
<211> LENGTH: 807
<212> TYPE: DNA
<213> ORGANISM: Artificial
<220> FEATURE:
<223> OTHER INFORMATION: synthetic sequence encoding Bacillus clausii
      variant

<400> SEQUENCE: 20
gcgcaatcag tgccatgggg aattagccgt gtgcaagccc cagctgccca taaccgtgga    60
ttgacaggtt ctggtgtaaa agttgctgtc ctcgatacag gtatttccac tcatccagac   120
ttaaatattc gtggtggcgc tagctttgta ccaggggaac catccactca agatgggaat   180
gggcatggca cgcatgtggc cgggacgatt gctgctttag acaattcgat tggcgttctt   240
ggcgtagcgc cgagagcgga actatacgct gttaaagtat taggggcgag cggttcaggt   300
tcggtcagct cgattgccca aggattggaa tgggcaggga caatcgtat gcacgttgct   360 aatttgagtt taggactgca ggcaccaagt gccacacttg agcaagctgt taatagcgcg   420
acttctagag gcgttcttgt tgtagcggca tctggaaatt caggtgcagg ctcaatcagc   480
tatccggccc gttatgcgaa cgcaatggca gtcggagcta ctgaccaaaa caacaaccgc   540
gccagctttt cacagtatgg cgcagggctt gacattgtcg caccaggtgt aaacgtgcag   600
agcacatacc caggttcaac gtatgccagc ttaaacggta catcgatggc tactcctcat   660
gttgcaggtg cagcagccct tgttaaacaa aagaacccat cttggtccaa tgtacaaatc   720
cgcaatcatc taaagaatac ggcaacgagc ttaggaagca cgaacttgta tggaagcgga   780
cttgtcaatg cagaagctgc aactcgt                                       807
```

```
<210> SEQ ID NO 21
<211> LENGTH: 269
<212> TYPE: PRT
<213> ORGANISM: Artificial
<220> FEATURE:
<223> OTHER INFORMATION: synthetic Bacillus clausii variant

<400> SEQUENCE: 21

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
        50                  55                  60

His Val Ala Gly Thr Ile Ala Ala Leu Asp Asn Ser Ile Gly Val Leu
65                  70                  75                  80

Gly Val Ala Pro Arg Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
```

```
                          100                 105                 110
        Gly Asn Asn Arg Met His Val Ala Asn Leu Ser Leu Gly Leu Gln Ala
                    115                 120                 125

Pro Ser Ala Thr Leu Glu Gln Ala Val Asn Ser Ala Thr Ser Arg Gly
                130                 135                 140

Val Leu Val Val Ala Ala Ser Gly Asn Ser Gly Ala Gly Ser Ile Ser
        145                 150                 155                 160

Tyr Pro Ala Arg Tyr Ala Asn Ala Met Ala Val Gly Ala Thr Asp Gln
                        165                 170                 175

Asn Asn Asn Arg Ala Ser Phe Ser Gln Tyr Gly Ala Gly Leu Asp Ile
                        180                 185                 190

Val Ala Pro Gly Val Asn Val Gln Ser Thr Tyr Pro Gly Ser Thr Tyr
                    195                 200                 205

Ala Ser Leu Asn Gly Thr Ser Met Ala Thr Pro His Val Ala Gly Ala
                    210                 215                 220

Ala Ala Leu Val Lys Gln Lys Asn Pro Ser Trp Ser Asn Val Gln Ile
        225                 230                 235                 240

Arg Asn His Leu Lys Asn Thr Ala Thr Ser Leu Gly Ser Thr Asn Leu
                        245                 250                 255

Tyr Gly Ser Gly Leu Val Asn Ala Glu Ala Ala Thr Arg
                    260                 265

<210> SEQ ID NO 22
<211> LENGTH: 807
<212> TYPE: DNA
<213> ORGANISM: Artificial
<220> FEATURE:
<223> OTHER INFORMATION: synthetic sequence encoding Bacillus clausii
      variant

<400> SEQUENCE: 22
gcgcaatcag tgccatgggg aattagccgt gtgcaagccc cagctgccca taaccgtgga    60
ttgacaggtt ctggtgtaaa agttgctgtc ctcgatacag gtatttccac tcatccagac   120
ttaaatattc gtggtggcgc tagctttgta ccaggggaac catccactca agatggaat    180 gggcatggca cgcatgtggc cgggacgatt gctgctttag acaattcgat tggcgttctt   240
ggcgtagcgc cgagagcgga actatacgct gttaaagtat taggggcgag cggttcaggt   300
tcggtcagct cgattgccca aggattggaa tgggcaggga caatcgtat gcacgttgct   360 aatttgagtt taggactgca ggcaccaagt gccacacttg agcaagctgt taatagcgcg   420
acttctagag gcgttcttgt tgtagcggca tctggaaatt caggtgcagg ctcaatcagc   480
tatccggccc gttatgcgaa cgcaatggca gtcggagcta ctgaccaaaa caacaaccgc   540
gccgattttt cacagtatgg cgcagggctt gacattgtcg caccaggtgt aaacgtgcag   600
agcacatacc caggttcaac gtatgccagc ttaaacggta tcgatggc tactcctcat   660 gttgcaggtg cagcagccct tgttaaacaa aagaacccat cttggtccaa tcgtcaaatc   720
cgcaatcatc taaagaatac ggcaacgagc ttaggaagca cgaacttgta tggaagcgga   780
cttgtcaatg cagaagctgc aactcgt                                       807

<210> SEQ ID NO 23
<211> LENGTH: 269
<212> TYPE: PRT
<213> ORGANISM: Artificial
<220> FEATURE:
<223> OTHER INFORMATION: synthetic Bacillus clausii variant
```

<400> SEQUENCE: 23

```
Ala Gln Ser Val Pro Trp Gly Ile Ser Arg Val Gln Ala Pro Ala Ala
1               5                   10                  15
His Asn Arg Gly Leu Thr Gly Ser Gly Val Lys Val Ala Val Leu Asp
            20                  25                  30
Thr Gly Ile Ser Thr His Pro Asp Leu Asn Ile Arg Gly Gly Ala Ser
        35                  40                  45
Phe Val Pro Gly Glu Pro Ser Thr Gln Asp Gly Asn Gly His Gly Thr
    50                  55                  60
His Val Ala Gly Thr Ile Ala Ala Leu Asp Asn Ser Ile Gly Val Leu
65                  70                  75                  80
Gly Val Ala Pro Arg Ala Glu Leu Tyr Ala Val Lys Val Leu Gly Ala
                85                  90                  95
Ser Gly Ser Gly Ser Val Ser Ser Ile Ala Gln Gly Leu Glu Trp Ala
            100                 105                 110
Gly Asn Asn Arg Met His Val Ala Asn Leu Ser Leu Gly Leu Gln Ala
        115                 120                 125
Pro Ser Ala Thr Leu Glu Gln Ala Val Asn Ser Ala Thr Ser Arg Gly
    130                 135                 140
Val Leu Val Val Ala Ala Ser Gly Asn Ser Gly Ala Gly Ser Ile Ser
145                 150                 155                 160
Tyr Pro Ala Arg Tyr Ala Asn Ala Met Ala Val Gly Ala Thr Asp Gln
                165                 170                 175
Asn Asn Asn Arg Ala Asp Phe Ser Gln Tyr Gly Ala Gly Leu Asp Ile
            180                 185                 190
Val Ala Pro Gly Val Asn Val Gln Ser Thr Tyr Pro Gly Ser Thr Tyr
        195                 200                 205
Ala Ser Leu Asn Gly Thr Ser Met Ala Thr Pro His Val Ala Gly Ala
    210                 215                 220
Ala Ala Leu Val Lys Gln Lys Asn Pro Ser Trp Ser Asn Arg Gln Ile
225                 230                 235                 240
Arg Asn His Leu Lys Asn Thr Ala Thr Ser Leu Gly Ser Thr Asn Leu
                245                 250                 255
Tyr Gly Ser Gly Leu Val Asn Ala Glu Ala Ala Thr Arg
            260                 265
```

<210> SEQ ID NO 24
<211> LENGTH: 807
<212> TYPE: DNA
<213> ORGANISM: Artificial
<220> FEATURE:
<223> OTHER INFORMATION: synthetic sequence encoding Bacillus clausii variant

<400> SEQUENCE: 24

```
gcgcaatcag tgccatgggg aattagccgt gtgcaagccc cagctgccca taaccgtgga      60
ttgacaggtt ctggtgtaaa agttgctgtc ctcgatacag gtatttccac tcatccagac    120
ttaaatattc gtggtggcgc tagctttgta ccaggggaac catccactca agatgggaat    180
gggcatggca cgcatgtggc cgggacgatt gctgctttag acaattcgat tggcgttctt    240
ggcgtagcgc cgagagcgga actatacgct gttaaagtat taggggcgag cggttcaggt    300
tcggtcagct cgattgccca aggattggaa tgggcaggga caatcgtat gcacgttgct    360
aatttgagtt taggactgca ggcaccaagt gccacacttg agcaagctgt taatagcgcg    420
acttctagag gcgttcttgt tgtagcggca tctggaaatt caggtgcagg ctcaatcagc    480
```

```
tatccggccc gttatgcgaa cgcaatggca gtcggagcta ctgaccaaaa caacaaccgc      540
gccgattttt cacagtatgg cgcagggctt gacattgtcg caccaggtgt aaacgtgcag      600
agcacatacc caggttcaac gtatgccagc ttaaacggta catcgatggc tactcctcat      660
gttgcaggtg cagcagccct tgttaaacaa aagaacccat cttggtccaa tgtacaaatc      720
cgcagacatc taaagaatac ggcaacgagc ttaggaagca cgaacttgta tggaagcgga      780
cttgtcaatg cagaagctgc aactcgt                                         807
```

<210> SEQ ID NO 25
<211> LENGTH: 269
<212> TYPE: PRT
<213> ORGANISM: Artificial
<220> FEATURE:
<223> OTHER INFORMATION: synthetic Bacillus clausii variant

<400> SEQUENCE: 25

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asp Asn Ser Ile Gly Val Leu
65                  70                  75                  80

Gly Val Ala Pro Arg Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Leu Gln Ala
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Asp Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Arg His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

<210> SEQ ID NO 26
<211> LENGTH: 43
<212> TYPE: DNA
<213> ORGANISM: Artificial

```
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 26
gctgctgaag aagcaaaann saaatattta attggcttta atg          43

<210> SEQ ID NO 27
<211> LENGTH: 43
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (24)..(25)
<223> OTHER INFORMATION: n is a, c, g, or t

<400> SEQUENCE: 27
cattaaagcc aattaaatat ttsnnttttg cttcttcagc agc          43

<210> SEQ ID NO 28
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 28
caagtagagg caaatgacnn sgtcgccatt ctctctgag              39

<210> SEQ ID NO 29
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 29
ctcagagaga atggcgacsn ngtcatttgc ctctacttg              39

<210> SEQ ID NO 30
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 30
gaggcaaatg acgaggtcnn sattctctct gaggaagag              39

<210> SEQ ID NO 31
<211> LENGTH: 39
<212> TYPE: DNA
```

```
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 31
ctcttcctca gagagaatsn ngacctcgtc atttgcctc                              39

<210> SEQ ID NO 32
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 32
caagtagagg caaatgacnn sgtcaaaatt ctctctgag                              39

<210> SEQ ID NO 33
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 33
ctcagagaga attttgacsn ngtcatttgc ctctacttg                              39

<210> SEQ ID NO 34
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 34
gaggcaaatg acggcgtcnn sattctctct gaggaagag                              39

<210> SEQ ID NO 35
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 35
ctcttcctca gagagaatsn ngacgccgtc atttgcctc                              39

<210> SEQ ID NO 36
<211> LENGTH: 39
```

<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 36
gaggcaaatg actcggtcnn sattctctct gaggaagag                39

<210> SEQ ID NO 37
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 37
ctcttcctca gagagaatsn ngaccgagtc atttgcctc                39

<210> SEQ ID NO 38
<211> LENGTH: 353
<212> TYPE: PRT
<213> ORGANISM: Artificial
<220> FEATURE:
<223> OTHER INFORMATION: synthetic peptide

<400> SEQUENCE: 38

Ala Glu Glu Ala Lys Glu Lys Tyr Leu Ile Gly Phe Asn Glu Gln Glu
1               5                   10                  15

Ala Val Ser Glu Phe Val Glu Gln Val Glu Ala Asn Asp Glu Val Ala
                20                  25                  30

Ile Leu Ser Glu Glu Glu Val Glu Ile Glu Leu Leu His Glu Phe
            35                  40                  45

Glu Thr Ile Pro Val Leu Ser Val Glu Leu Ser Pro Glu Asp Val Asp
50                  55                  60

Ala Leu Glu Leu Asp Pro Ala Ile Ser Tyr Ile Glu Glu Asp Ala Glu
65                  70                  75                  80

Val Thr Thr Met Ala Gln Ser Val Pro Trp Gly Ile Ser Arg Val Gln
                85                  90                  95

Ala Pro Ala Ala His Asn Arg Gly Leu Thr Gly Ser Gly Val Lys Val
                100                 105                 110

Ala Val Leu Asp Thr Gly Ile Ser Thr His Pro Asp Leu Asn Ile Arg
            115                 120                 125

Gly Gly Ala Ser Phe Val Pro Gly Glu Pro Ser Thr Gln Asp Gly Asn
        130                 135                 140

Gly His Gly Thr His Val Ala Gly Thr Ile Ala Ala Leu Asn Asn Ser
145                 150                 155                 160

Ile Gly Val Leu Gly Val Ala Pro Ser Ala Glu Leu Tyr Ala Val Lys
                165                 170                 175

Val Leu Gly Ala Ser Gly Ser Gly Ser Val Ser Ser Ile Ala Gln Gly
                180                 185                 190

Leu Glu Trp Ala Gly Asn Asn Gly Met His Val Ala Asn Leu Ser Leu
            195                 200                 205

Gly Ser Pro Ser Pro Ser Ala Thr Leu Glu Gln Ala Val Asn Ser Ala

```
                210                 215                 220
Thr Ser Arg Gly Val Leu Val Ala Ala Ser Gly Asn Ser Gly Ala
225                 230                 235                 240

Gly Ser Ile Ser Tyr Pro Ala Arg Tyr Ala Asn Ala Met Ala Val Gly
                245                 250                 255

Ala Thr Asp Gln Asn Asn Arg Ala Ser Phe Ser Gln Tyr Gly Ala
                260                 265                 270

Gly Leu Asp Ile Val Ala Pro Gly Val Asn Val Gln Ser Thr Tyr Pro
                275                 280                 285

Gly Ser Thr Tyr Ala Ser Leu Asn Gly Thr Ser Met Ala Thr Pro His
                290                 295                 300

Val Ala Gly Ala Ala Leu Val Lys Gln Lys Asn Pro Ser Trp Ser
305                 310                 315                 320

Asn Val Gln Ile Arg Asn His Leu Lys Asn Thr Ala Thr Ser Leu Gly
                325                 330                 335

Ser Thr Asn Leu Tyr Gly Ser Gly Leu Val Asn Ala Glu Ala Ala Thr
                340                 345                 350

Arg

<210> SEQ ID NO 39
<211> LENGTH: 353
<212> TYPE: PRT
<213> ORGANISM: Artificial
<220> FEATURE:
<223> OTHER INFORMATION: synthetic peptide

<400> SEQUENCE: 39

Ala Glu Glu Ala Lys Glu Lys Tyr Leu Ile Gly Phe Asn Glu Gln Glu
1               5                   10                  15

Ala Val Ser Glu Phe Val Glu Gln Val Glu Ala Asn Asp Glu Val Ala
                20                  25                  30

Ile Leu Ser Glu Glu Glu Val Gly Ile Glu Leu Leu His Glu Phe
                35                  40                  45

Glu Thr Ile Pro Val Leu Ser Val Glu Leu Ser Pro Glu Asp Val Asp
50                  55                  60

Ala Leu Glu Leu Asp Pro Ala Ile Ser Tyr Ile Glu Glu Asp Ala Glu
65                  70                  75                  80

Val Thr Thr Met Ala Gln Ser Val Pro Trp Gly Ile Ser Arg Val Gln
                85                  90                  95

Ala Pro Ala Ala His Asn Arg Gly Leu Thr Gly Ser Gly Val Lys Val
                100                 105                 110

Ala Val Leu Asp Thr Gly Ile Ser Thr His Pro Asp Leu Asn Ile Arg
                115                 120                 125

Gly Gly Ala Ser Phe Val Pro Gly Glu Pro Ser Thr Gln Asp Gly Asn
                130                 135                 140

Gly His Gly Thr His Val Ala Gly Thr Ile Ala Ala Leu Asp Asn Ser
145                 150                 155                 160

Ile Gly Val Leu Gly Val Ala Pro Ser Ala Glu Leu Tyr Ala Val Lys
                165                 170                 175

Val Leu Gly Ala Ser Gly Ser Gly Ala Ile Ser Ser Ile Ala Gln Gly
                180                 185                 190

Leu Glu Trp Ala Gly Asn Asn Gly Met His Val Ala Asn Leu Ser Leu
                195                 200                 205

Gly Ser Pro Ser Pro Ser Ala Thr Leu Glu Gln Ala Val Asn Ser Ala
                210                 215                 220
```

```
Thr Ser Arg Gly Val Leu Val Ala Ala Ser Gly Asn Ser Gly Ala
225                 230                 235                 240

Gly Ser Ile Ser Tyr Pro Ala Arg Tyr Ala Asn Ala Met Ala Val Gly
                245                 250                 255

Ala Thr Asp Gln Asn Asn Asn Arg Ala Ser Phe Ser Gln Tyr Gly Ala
                260                 265                 270

Gly Leu Asp Ile Val Ala Pro Gly Val Asn Val Gln Ser Thr Tyr Pro
                275                 280                 285

Gly Ser Thr Tyr Ala Ser Leu Asn Gly Thr Ser Met Ala Thr Pro His
                290                 295                 300

Val Ala Gly Ala Ala Ala Leu Val Lys Gln Lys Asn Pro Ser Trp Ser
305                 310                 315                 320

Asn Val Gln Ile Arg Asn His Leu Lys Asn Thr Ala Thr Ser Leu Gly
                325                 330                 335

Ser Thr Asn Leu Tyr Gly Ser Gly Leu Val Asn Ala Glu Ala Ala Thr
                340                 345                 350

Arg

<210> SEQ ID NO 40
<211> LENGTH: 353
<212> TYPE: PRT
<213> ORGANISM: Artificial
<220> FEATURE:
<223> OTHER INFORMATION: synthetic peptide

<400> SEQUENCE: 40

Ala Glu Glu Ala Lys Glu Lys Tyr Leu Ile Gly Phe Asn Glu Gln Glu
1               5                   10                  15

Ala Val Ser Glu Phe Val Glu Gln Val Glu Ala Asn Asp Glu Val Ala
                20                  25                  30

Ile Leu Ser Glu Glu Glu Val Glu Ile Glu Leu Leu His Glu Phe
                35                  40                  45

Glu Thr Ile Pro Val Leu Ser Val Glu Leu Ser Pro Glu Asp Val Asp
50                  55                  60

Ala Leu Glu Leu Asp Pro Ala Ile Ser Tyr Ile Glu Gly Asp Ala Glu
65                  70                  75                  80

Val Thr Thr Met Ala Gln Ser Val Pro Trp Gly Ile Ser Arg Val Gln
                85                  90                  95

Ala Pro Ala Ala His Asn Arg Gly Leu Thr Gly Ser Gly Val Lys Val
                100                 105                 110

Ala Val Leu Asp Thr Gly Ile Ser Thr His Pro Asp Leu Asn Ile Arg
                115                 120                 125

Gly Gly Ala Ser Phe Val Pro Gly Glu Pro Ser Thr Gln Asp Gly Asn
                130                 135                 140

Gly His Gly Thr His Val Ala Gly Thr Ile Ala Ala Leu Asn Asn Ser
145                 150                 155                 160

Ile Gly Val Leu Gly Val Ala Pro Asn Ala Glu Leu Tyr Ala Val Lys
                165                 170                 175

Val Leu Gly Ala Ser Gly Ser Gly Ser Val Ser Ser Ile Ala Gln Gly
                180                 185                 190

Leu Glu Trp Ala Gly Asn Asn Gly Met His Val Ala Asn Leu Ser Leu
                195                 200                 205

Gly Ser Pro Ser Pro Ser Ala Thr Leu Glu Gln Ala Val Asn Ser Ala
                210                 215                 220
```

```
Thr Ser Arg Gly Val Leu Val Val Ala Ala Ser Gly Asn Ser Gly Ala
225                 230                 235                 240

Gly Ser Ile Ser Tyr Pro Ala Arg Tyr Ala Asn Ala Met Ala Val Gly
                245                 250                 255

Ala Thr Asp Gln Asn Asn Arg Ala Ser Phe Ser Gln Tyr Gly Ala
            260                 265                 270

Gly Leu Asp Ile Val Ala Pro Gly Val Asn Val Gln Ser Thr Tyr Pro
            275                 280                 285

Gly Ser Thr Tyr Ala Ser Leu Asn Gly Thr Ser Met Ala Thr Pro His
            290                 295                 300

Val Ala Gly Ala Ala Ala Leu Val Lys Gln Lys Asn Pro Ser Trp Ser
305                 310                 315                 320

Asn Val Gln Ile Arg Asn His Leu Lys Asn Thr Ala Thr Ser Leu Gly
                325                 330                 335

Ser Thr Asn Leu Tyr Gly Ser Gly Leu Val Asn Ala Glu Ala Ala Thr
            340                 345                 350

Arg
```

<210> SEQ ID NO 41
<211> LENGTH: 353
<212> TYPE: PRT
<213> ORGANISM: Artificial
<220> FEATURE:
<223> OTHER INFORMATION: synthetic peptide

<400> SEQUENCE: 41

```
Ala Glu Glu Ala Lys Glu Lys Tyr Leu Ile Gly Phe Asn Glu Gln Glu
1               5                   10                  15

Ala Val Ser Glu Phe Val Glu Gln Val Glu Ala Asn Asp Glu Val Ala
                20                  25                  30

Ile Leu Ser Glu Glu Glu Val Glu Ile Glu Leu Leu His Glu Phe
            35                  40                  45

Glu Thr Ile Pro Val Leu Ser Val Glu Leu Ser Pro Glu Asp Val Asp
    50                  55                  60

Ala Leu Glu Leu Asp Pro Ala Ile Ser Tyr Ile Glu Glu Asp Ala Glu
65                  70                  75                  80

Val Thr Thr Met Ala Gln Ser Val Pro Trp Gly Ile Ser Arg Val Gln
                85                  90                  95

Ala Pro Ala Ala His Asn Arg Gly Leu Thr Gly Ser Gly Val Lys Val
                100                 105                 110

Ala Val Leu Asp Thr Gly Ile Ser Thr His Pro Asp Leu Asn Ile Arg
            115                 120                 125

Gly Gly Ala Ser Phe Val Pro Gly Glu Pro Ser Thr Gln Asp Gly Asn
130                 135                 140

Gly His Gly Thr His Val Ala Gly Thr Ile Ala Ala Leu Asn Asn Ser
145                 150                 155                 160

Ile Gly Val Leu Gly Val Ala Pro Asn Ala Glu Leu Tyr Ala Val Lys
                165                 170                 175

Val Leu Gly Ala Ser Gly Ser Gly Ser Val Ser Ser Ile Ala Gln Gly
            180                 185                 190

Leu Glu Trp Ala Gly Asn Asn Val Met His Val Ala Asn Leu Ser Leu
            195                 200                 205

Gly Leu Gln Ala Pro Ser Ala Thr Leu Glu Gln Ala Val Asn Ser Ala
210                 215                 220

Thr Ser Arg Gly Val Leu Val Val Ala Ala Ser Gly Asn Ser Gly Ala
```

```
                225                 230                 235                 240

Gly Ser Ile Ser Tyr Pro Ala Arg Tyr Ala Asn Ala Met Ala Val Gly
                245                 250                 255

Ala Thr Asp Gln Asn Asn Arg Ala Ser Phe Ser Gln Tyr Gly Ala
                260                 265                 270

Gly Leu Asp Ile Val Ala Pro Gly Val Asn Val Gln Ser Thr Tyr Pro
                275                 280                 285

Gly Ser Thr Tyr Ala Ser Leu Asn Gly Thr Ser Met Ala Thr Pro His
            290                 295                 300

Val Ala Gly Ala Ala Ala Leu Val Lys Gln Lys Asn Pro Ser Trp Ser
305                 310                 315                 320

Asn Val Gln Ile Arg Asn His Leu Lys Asn Thr Ala Thr Ser Leu Gly
                325                 330                 335

Ser Thr Asn Leu Tyr Gly Ser Gly Leu Val Asn Ala Glu Ala Ala Thr
                340                 345                 350

Arg

<210> SEQ ID NO 42
<211> LENGTH: 353
<212> TYPE: PRT
<213> ORGANISM: Artificial
<220> FEATURE:
<223> OTHER INFORMATION: synthetic peptide

<400> SEQUENCE: 42

Ala Glu Glu Ala Lys Glu Lys Tyr Leu Ile Gly Phe Asn Glu Gln Glu
1               5                   10                  15

Ala Val Ser Glu Phe Val Glu Gln Val Glu Ala Asn Asp Glu Val Ala
                20                  25                  30

Ile Leu Ser Glu Glu Glu Glu Val Glu Ile Glu Leu Leu His Glu Phe
                35                  40                  45

Glu Thr Ile Pro Val Leu Ser Val Glu Leu Ser Pro Glu Asp Val Asp
            50                  55                  60

Ala Leu Glu Leu Asp Pro Ala Ile Ser Tyr Ile Glu Glu Asp Ala Glu
65                  70                  75                  80

Val Thr Thr Met Ala Gln Ser Val Pro Trp Gly Ile Ser Arg Val Gln
                85                  90                  95

Ala Pro Ala Ala His Asn Arg Gly Leu Thr Gly Ser Gly Val Lys Val
                100                 105                 110

Ala Val Leu Asp Thr Gly Ile Ser Thr His Pro Asp Leu Asn Ile Arg
                115                 120                 125

Gly Gly Ala Ser Phe Val Pro Gly Glu Pro Ser Thr Gln Asp Gly Asn
            130                 135                 140

Gly His Gly Thr His Val Ala Gly Thr Ile Ala Ala Leu Asn Asn Ser
145                 150                 155                 160

Ile Gly Val Leu Gly Val Ala Pro Asn Ala Glu Leu Tyr Ala Val Lys
                165                 170                 175

Val Leu Gly Ala Ser Gly Met Gly Ser Val Ser Ser Ile Ala Gln Gly
                180                 185                 190

Leu Glu Trp Ala Gly Asn Asn Val Met His Val Ala Asn Leu Ser Leu
                195                 200                 205

Gly Leu Gln Ala Pro Ser Ala Thr Leu Glu Gln Ala Val Asn Ser Ala
            210                 215                 220

Thr Ser Arg Gly Val Leu Val Val Ala Ala Ser Gly Asn Ser Gly Ala
225                 230                 235                 240
```

```
Gly Ser Ile Ser Tyr Pro Ala Arg Tyr Ala Asn Ala Met Ala Val Gly
                245                 250                 255

Ala Thr Asp Gln Asn Asn Arg Ala Ser Phe Ser Gln Tyr Gly Ala
            260                 265                 270

Gly Leu Asp Ile Val Ala Pro Gly Val Asn Val Gln Ser Thr Tyr Pro
            275                 280                 285

Gly Ser Thr Tyr Ala Ser Leu Asn Gly Thr Ser Met Ala Thr Pro His
            290                 295                 300

Val Ala Gly Ala Ala Ala Leu Val Lys Gln Lys Asn Pro Ser Trp Ser
305                 310                 315                 320

Asn Val Gln Ile Arg Asn His Leu Lys Asn Thr Ala Thr Ser Leu Gly
                325                 330                 335

Ser Thr Asn Leu Tyr Gly Ser Gly Leu Val Asn Ala Glu Ala Ala Thr
                340                 345                 350

Arg
```

<210> SEQ ID NO 43
<211> LENGTH: 353
<212> TYPE: PRT
<213> ORGANISM: Artificial
<220> FEATURE:
<223> OTHER INFORMATION: synthetic primer

<400> SEQUENCE: 43

```
Ala Glu Glu Ala Lys Glu Lys Tyr Leu Ile Gly Phe Asn Glu Gln Glu
1               5                   10                  15

Ala Val Ser Glu Phe Val Glu Gln Val Ala Asn Asp Glu Val Ala
                20                  25                  30

Ile Leu Ser Glu Glu Glu Val Glu Ile Glu Leu Leu His Glu Phe
            35                  40                  45

Glu Thr Ile Pro Val Leu Ser Val Glu Leu Ser Pro Glu Asp Val Asp
50                  55                  60

Ala Leu Glu Leu Asp Pro Ala Ile Ser Tyr Ile Glu Glu Asp Ala Glu
65                  70                  75                  80

Val Thr Thr Met Ala Gln Ser Val Pro Trp Gly Ile Ser Arg Val Gln
                85                  90                  95

Ala Pro Ala Ala His Asn Arg Gly Leu Thr Gly Ser Gly Val Lys Val
            100                 105                 110

Ala Val Leu Asp Thr Gly Ile Ser Thr His Pro Asp Leu Asn Ile Arg
            115                 120                 125

Gly Gly Ala Ser Phe Val Pro Gly Glu Pro Ser Thr Gln Asp Gly Asn
130                 135                 140

Gly His Gly Thr His Val Ala Gly Thr Ile Ala Ala Leu Asn Asn Ser
145                 150                 155                 160

Ile Gly Val Leu Gly Val Ala Pro Asn Ala Glu Leu Tyr Ala Val Lys
                165                 170                 175

Val Leu Gly Ala Ser Gly Gly Ser Asn Ser Ser Ile Ala Gln Gly
            180                 185                 190

Leu Glu Trp Ala Gly Asn Asn Gly Met His Val Ala Asn Leu Ser Leu
            195                 200                 205

Gly Ser Pro Ser Pro Ser Ala Thr Leu Glu Gln Ala Val Asn Ser Ala
210                 215                 220

Thr Ser Arg Gly Val Leu Val Val Ala Ala Ser Gly Asn Ser Gly Ala
225                 230                 235                 240
```

Gly Ser Ile Ser Tyr Pro Ala Arg Tyr Ala Asn Ala Met Ala Val Gly
                245                 250                 255

Ala Thr Asp Gln Asn Asn Asn Arg Ala Ser Phe Ser Gln Tyr Gly Ala
            260                 265                 270

Gly Leu Asp Ile Val Ala Pro Gly Val Asn Val Gln Ser Thr Tyr Pro
            275                 280                 285

Gly Ser Thr Tyr Ala Ser Leu Asn Gly Thr Ser Met Ala Thr Pro His
            290                 295                 300

Val Ala Gly Ala Ala Ala Leu Val Lys Gln Lys Asn Pro Ser Trp Ser
305                 310                 315                 320

Asn Val Gln Ile Arg Asn His Leu Lys Asn Thr Ala Thr Ser Leu Gly
                325                 330                 335

Ser Thr Asn Leu Tyr Gly Ser Gly Leu Val Asn Ala Glu Ala Ala Thr
            340                 345                 350

Arg

<210> SEQ ID NO 44
<211> LENGTH: 353
<212> TYPE: PRT
<213> ORGANISM: Artificial
<220> FEATURE:
<223> OTHER INFORMATION: synthetic peptide

<400> SEQUENCE: 44

Ala Glu Glu Ala Lys Glu Lys Tyr Leu Ile Gly Phe Asn Glu Gln Glu
1               5                   10                  15

Ala Val Ser Glu Phe Val Glu Gln Val Glu Ala Asn Asp Glu Val Ala
            20                  25                  30

Ile Leu Ser Glu Glu Glu Val Glu Ile Glu Leu Leu His Glu Phe
            35                  40                  45

Glu Thr Ile Pro Val Leu Ser Val Glu Leu Ser Pro Glu Asp Val Asp
    50                  55                  60

Ala Leu Glu Leu Asp Pro Ala Ile Ser Tyr Ile Glu Glu Asp Ala Glu
65                  70                  75                  80

Val Thr Thr Met Ala Gln Ser Val Pro Trp Gly Ile Ser Arg Val Gln
                85                  90                  95

Ala Pro Ala Ala His Asn Arg Gly Leu Thr Gly Ser Gly Val Lys Val
            100                 105                 110

Ala Val Leu Asp Thr Gly Ile Ser Thr His Pro Asp Leu Asn Ile Arg
            115                 120                 125

Gly Gly Ala Ser Phe Val Pro Gly Glu Pro Ser Thr Gln Asp Gly Asn
            130                 135                 140

Gly His Gly Thr His Val Ala Gly Thr Ile Ala Ala Leu Asp Asn Ser
145                 150                 155                 160

Ile Gly Val Leu Gly Val Ala Pro Arg Ala Glu Leu Tyr Ala Val Lys
                165                 170                 175

Val Leu Gly Ala Ser Gly Ser Gly Ser Val Ser Ser Ile Ala Gln Gly
            180                 185                 190

Leu Glu Trp Ala Gly Asn Asn Arg Met His Val Ala Asn Leu Ser Leu
            195                 200                 205

Gly Leu Gln Ala Pro Ser Ala Thr Leu Glu Gln Ala Val Asn Ser Ala
            210                 215                 220

Thr Ser Arg Gly Val Leu Val Val Ala Ala Ser Gly Asn Ser Gly Ala
225                 230                 235                 240

Gly Ser Ile Ser Tyr Pro Ala Arg Tyr Ala Asn Ala Met Ala Val Gly

```
                245                 250                 255
Ala Thr Asp Gln Asn Asn Arg Ala Ser Phe Ser Gln Tyr Gly Ala
                260                 265                 270

Gly Leu Asp Ile Val Ala Pro Gly Val Asn Val Gln Ser Thr Tyr Pro
                275                 280                 285

Gly Ser Thr Tyr Ala Ser Leu Asn Gly Thr Ser Met Ala Thr Pro His
                290                 295                 300

Val Ala Gly Ala Ala Leu Val Lys Gln Lys Asn Pro Ser Trp Ser
305                 310                 315                 320

Asn Val Gln Ile Arg Asn His Leu Lys Asn Thr Ala Thr Ser Leu Gly
                325                 330                 335

Ser Thr Asn Leu Tyr Gly Ser Gly Leu Val Asn Ala Glu Ala Ala Thr
                340                 345                 350

Arg

<210> SEQ ID NO 45
<211> LENGTH: 353
<212> TYPE: PRT
<213> ORGANISM: Artificial
<220> FEATURE:
<223> OTHER INFORMATION: synthetic peptide

<400> SEQUENCE: 45

Ala Glu Glu Ala Lys Glu Lys Tyr Leu Ile Gly Phe Asn Glu Gln Glu
1               5                   10                  15

Ala Val Ser Glu Phe Val Glu Gln Val Glu Ala Asn Asp Glu Val Ala
                20                  25                  30

Ile Leu Ser Glu Glu Glu Val Glu Ile Glu Leu Leu His Glu Phe
                35                  40                  45

Glu Thr Ile Pro Val Leu Ser Val Glu Leu Ser Pro Glu Asp Val Asp
            50                  55                  60

Ala Leu Glu Leu Asp Pro Ala Ile Ser Tyr Ile Glu Glu Asp Ala Glu
65                  70                  75                  80

Val Thr Thr Met Ala Gln Ser Val Pro Trp Gly Ile Ser Arg Val Gln
                85                  90                  95

Ala Pro Ala Ala His Asn Arg Gly Leu Thr Gly Ser Gly Val Lys Val
                100                 105                 110

Ala Val Leu Asp Thr Gly Ile Ser Thr His Pro Asp Leu Asn Ile Arg
                115                 120                 125

Gly Gly Ala Ser Phe Val Pro Gly Glu Pro Ser Thr Gln Asp Gly Asn
                130                 135                 140

Gly His Gly Thr His Val Ala Gly Thr Ile Ala Ala Leu Asp Asn Ser
145                 150                 155                 160

Ile Gly Val Leu Gly Val Ala Pro Arg Ala Glu Leu Tyr Ala Val Lys
                165                 170                 175

Val Leu Gly Ala Ser Gly Ser Gly Ser Val Ser Ser Ile Ala Gln Gly
                180                 185                 190

Leu Glu Trp Ala Gly Asn Asn Arg Met His Val Ala Asn Leu Ser Leu
                195                 200                 205

Gly Leu Gln Ala Pro Ser Ala Thr Leu Glu Gln Ala Val Asn Ser Ala
                210                 215                 220

Thr Ser Arg Gly Val Leu Val Ala Ala Ser Gly Asn Ser Gly Ala
225                 230                 235                 240

Gly Ser Ile Ser Tyr Pro Ala Arg Tyr Ala Asn Ala Met Ala Val Gly
                245                 250                 255
```

```
Ala Thr Asp Gln Asn Asn Asn Arg Ala Asp Phe Ser Gln Tyr Gly Ala
            260                 265                 270

Gly Leu Asp Ile Val Ala Pro Gly Val Asn Val Gln Ser Thr Tyr Pro
        275                 280                 285

Gly Ser Thr Tyr Ala Ser Leu Asn Gly Thr Ser Met Ala Thr Pro His
    290                 295                 300

Val Ala Gly Ala Ala Leu Val Lys Gln Lys Asn Pro Ser Trp Ser
305                 310                 315                 320

Asn Arg Gln Ile Arg Asn His Leu Lys Asn Thr Ala Thr Ser Leu Gly
                325                 330                 335

Ser Thr Asn Leu Tyr Gly Ser Gly Leu Val Asn Ala Glu Ala Ala Thr
            340                 345                 350

Arg

<210> SEQ ID NO 46
<211> LENGTH: 353
<212> TYPE: PRT
<213> ORGANISM: Artificial
<220> FEATURE:
<223> OTHER INFORMATION: synthetic peptide

<400> SEQUENCE: 46

Ala Glu Glu Ala Lys Glu Lys Tyr Leu Ile Gly Phe Asn Glu Gln Glu
1               5                   10                  15

Ala Val Ser Glu Phe Val Glu Gln Val Glu Ala Asn Asp Glu Val Ala
            20                  25                  30

Ile Leu Ser Glu Glu Glu Glu Val Glu Ile Glu Leu Leu His Glu Phe
        35                  40                  45

Glu Thr Ile Pro Val Leu Ser Val Glu Leu Ser Pro Glu Asp Val Asp
    50                  55                  60

Ala Leu Glu Leu Asp Pro Ala Ile Ser Tyr Ile Glu Glu Asp Ala Glu
65                  70                  75                  80

Val Thr Thr Met Ala Gln Ser Val Pro Trp Gly Ile Ser Arg Val Gln
                85                  90                  95

Ala Pro Ala Ala His Asn Arg Gly Leu Thr Gly Ser Gly Val Lys Val
            100                 105                 110

Ala Val Leu Asp Thr Gly Ile Ser Thr His Pro Asp Leu Asn Ile Arg
        115                 120                 125

Gly Gly Ala Ser Phe Val Pro Gly Glu Pro Ser Thr Gln Asp Gly Asn
    130                 135                 140

Gly His Gly Thr His Val Ala Gly Thr Ile Ala Ala Leu Asp Asn Ser
145                 150                 155                 160

Ile Gly Val Leu Gly Val Ala Pro Arg Ala Glu Leu Tyr Ala Val Lys
                165                 170                 175

Val Leu Gly Ala Ser Gly Ser Gly Ser Val Ser Ser Ile Ala Gln Gly
            180                 185                 190

Leu Glu Trp Ala Gly Asn Asn Gly Met His Val Ala Asn Leu Ser Leu
        195                 200                 205

Gly Leu Gln Ala Pro Ser Ala Thr Leu Glu Gln Ala Val Asn Ser Ala
    210                 215                 220

Thr Ser Arg Gly Val Leu Val Val Ala Ala Ser Gly Asn Ser Gly Ala
225                 230                 235                 240

Gly Ser Ile Ser Tyr Pro Ala Arg Tyr Ala Asn Ala Met Ala Val Gly
                245                 250                 255
```

```
Ala Thr Asp Gln Asn Asn Asn Arg Ala Asp Phe Ser Gln Tyr Gly Ala
            260                 265                 270

Gly Leu Asp Ile Val Ala Pro Gly Val Asn Val Gln Ser Thr Tyr Pro
            275                 280                 285

Gly Ser Thr Tyr Ala Ser Leu Asn Gly Thr Ser Met Ala Thr Pro His
            290                 295                 300

Val Ala Gly Ala Ala Leu Val Lys Gln Lys Asn Pro Ser Trp Ser
305                 310                 315                 320

Asn Val Gln Ile Arg Arg His Leu Lys Asn Thr Ala Thr Ser Leu Gly
                325                 330                 335

Ser Thr Asn Leu Tyr Gly Ser Gly Leu Val Asn Ala Glu Ala Ala Thr
            340                 345                 350

Arg
```

<210> SEQ ID NO 47
<211> LENGTH: 269
<212> TYPE: PRT
<213> ORGANISM: Bacillus alcalophilus

<400> SEQUENCE: 47

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Asn Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
    195                 200                 205

Ala Ser Leu Asn Gly Thr Ser Met Ala Thr Pro His Val Ala Gly Ala
            210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

<210> SEQ ID NO 48
<211> LENGTH: 268
<212> TYPE: PRT
<213> ORGANISM: Bacillus sp.

<400> SEQUENCE: 48

```
Gln Thr Val Pro Trp Gly Ile Asn Arg Val Gln Ala Pro Ile Ala Gln
  1               5                  10                  15

Ser Arg Gly Phe Thr Gly Thr Gly Val Arg Val Ala Val Leu Asp Thr
                 20                  25                  30

Gly Ile Ser Asn His Ala Asp Leu Arg Ile Arg Gly Gly Ala Ser Phe
             35                  40                  45

Val Pro Gly Glu Pro Asn Ile Ser Asp Gly Asn Gly His Gly Thr Gln
 50                  55                  60

Val Ala Gly Thr Ile Ala Ala Leu Asn Asn Ser Ile Gly Val Leu Gly
 65                  70                  75                  80

Val Ala Pro Asn Val Asp Leu Tyr Gly Val Lys Val Leu Gly Ala Ser
                 85                  90                  95

Gly Ser Gly Ser Ile Ser Gly Ile Ala Gln Gly Leu Gln Trp Ala Ala
                100                 105                 110

Asn Asn Gly Met His Ile Ala Asn Met Ser Leu Gly Ser Ser Ala Gly
                115                 120                 125

Ser Ala Thr Met Glu Gln Ala Val Asn Gln Ala Thr Ala Ser Gly Val
            130                 135                 140

Leu Val Val Ala Ala Ser Gly Asn Ser Gly Ala Gly Asn Val Gly Phe
145                 150                 155                 160

Pro Ala Arg Tyr Ala Asn Ala Met Ala Val Gly Ala Thr Asp Gln Asn
                165                 170                 175

Asn Asn Arg Ala Thr Phe Ser Gln Tyr Gly Ala Gly Leu Asp Ile Val
                180                 185                 190

Ala Pro Gly Val Gly Val Gln Ser Thr Val Pro Gly Asn Gly Tyr Ala
            195                 200                 205

Ser Phe Asn Gly Thr Ser Met Ala Thr Pro His Val Ala Gly Val Ala
        210                 215                 220

Ala Leu Val Lys Gln Lys Asn Pro Ser Trp Ser Asn Val Gln Ile Arg
225                 230                 235                 240

Asn His Leu Lys Asn Thr Ala Thr Asn Leu Gly Asn Thr Thr Gln Phe
                245                 250                 255

Gly Ser Gly Leu Val Asn Ala Glu Ala Ala Thr Arg
                260                 265
```

<210> SEQ ID NO 49
<211> LENGTH: 268
<212> TYPE: PRT
<213> ORGANISM: Bacillus sp.

<400> SEQUENCE: 49

```
Gln Thr Val Pro Trp Gly Ile Asn Arg Val Gln Ala Pro Ile Ala Gln
  1               5                  10                  15

Ser Arg Gly Phe Thr Gly Thr Gly Val Arg Val Ala Val Leu Asp Thr
                 20                  25                  30

Gly Ile Ser Asn His Ala Asp Leu Arg Ile Arg Gly Gly Ala Ser Phe
             35                  40                  45

Val Pro Gly Glu Pro Asn Ile Ser Asp Gly Asn Gly His Gly Thr His
 50                  55                  60
```

```
Val Ala Gly Thr Ile Ala Ala Leu Asn Asn Ser Ile Gly Val Leu Gly
 65                  70                  75                  80

Val Ala Pro Asn Val Asp Leu Tyr Gly Val Lys Val Leu Gly Ala Ser
                 85                  90                  95

Gly Ser Gly Ser Ile Ser Gly Ile Ala Gln Gly Leu Gln Trp Ala Ala
            100                 105                 110

Asn Asn Gly Met His Ile Ala Asn Met Ser Leu Gly Ser Ser Ala Gly
            115                 120                 125

Ser Ala Thr Met Glu Gln Ala Val Asn Gln Ala Thr Ala Ser Gly Val
        130                 135                 140

Leu Val Val Ala Ala Ser Gly Asn Ser Gly Ala Gly Asn Val Gly Phe
145                 150                 155                 160

Pro Ala Arg Tyr Ala Asn Ala Met Ala Val Gly Ala Thr Asp Gln Asn
                165                 170                 175

Asn Asn Arg Ala Ser Phe Ser Gln Tyr Gly Ala Gly Leu Asp Ile Val
            180                 185                 190

Ala Pro Gly Val Gly Val Gln Ser Thr Val Pro Gly Asn Gly Tyr Ser
        195                 200                 205

Ser Phe Asn Gly Thr Ser Met Ala Thr Pro His Val Ala Gly Val Ala
210                 215                 220

Ala Leu Val Lys Gln Lys Asn Pro Ser Trp Ser Asn Val Gln Ile Arg
225                 230                 235                 240

Asn His Leu Lys Asn Thr Ala Thr Asn Leu Gly Asn Thr Asn Gln Phe
                245                 250                 255

Gly Ser Gly Leu Val Asn Ala Glu Ala Ala Thr Arg
            260                 265

<210> SEQ ID NO 50
<211> LENGTH: 269
<212> TYPE: PRT
<213> ORGANISM: Bacillus clausii

<400> SEQUENCE: 50

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
        50                  55                  60

His Val Ala Gly Thr Ile Ala Ala Leu Asn Asn Ser Ile Gly Val Leu
 65                  70                  75                  80

Gly Val Ala Pro Ser Ala Glu Leu Tyr Ala Val Lys Val Leu Gly Ala
                 85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
        130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175
```

```
Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Val
        210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Gly Leu Gly Asn Thr Asn Leu
                245                 250                 255

Tyr Gly Ser Gly Leu Val Asn Ala Glu Ala Ala Thr Arg
        260                 265

<210> SEQ ID NO 51
<211> LENGTH: 269
<212> TYPE: PRT
<213> ORGANISM: Bacillus sp.

<400> SEQUENCE: 51

Asn Gln Val Thr Pro Trp Gly Ile Thr Arg Val Gln Ala Pro Thr Ala
1               5                   10                  15

Trp Thr Arg Gly Tyr Thr Gly Thr Gly Val Arg Val Ala Val Leu Asp
            20                  25                  30

Thr Gly Ile Ser Thr His Pro Asp Leu Asn Ile Arg Gly Gly Val Ser
        35                  40                  45

Phe Val Pro Gly Glu Pro Ser Tyr Gln Asp Gly Asn Gly His Gly Thr
    50                  55                  60

His Val Ala Gly Thr Ile Ala Ala Leu Asn Asn Ser Ile Gly Val Val
65                  70                  75                  80

Gly Val Ala Pro Asn Ala Glu Leu Tyr Ala Val Lys Val Leu Gly Ala
                85                  90                  95

Asn Gly Ser Gly Ser Val Ser Ser Ile Ala Gln Gly Leu Gln Trp Thr
            100                 105                 110

Ala Gln Asn Asn Ile His Val Ala Asn Leu Ser Leu Gly Ser Pro Val
        115                 120                 125

Gly Ser Gln Thr Leu Glu Leu Ala Val Asn Gln Ala Thr Asn Ala Gly
    130                 135                 140

Val Leu Val Val Ala Ala Thr Gly Asn Asn Gly Ser Gly Thr Val Ser
145                 150                 155                 160

Tyr Pro Ala Arg Tyr Ala Asn Ala Leu Ala Val Gly Ala Thr Asp Gln
                165                 170                 175

Asn Asn Asn Arg Ala Ser Phe Ser Gln Tyr Gly Thr Gly Leu Asn Ile
            180                 185                 190

Val Ala Pro Gly Val Gly Ile Gln Ser Thr Tyr Pro Gly Asn Arg Tyr
        195                 200                 205

Ala Ser Leu Ser Gly Thr Ser Met Ala Thr Pro His Val Ala Gly Val
    210                 215                 220

Ala Ala Leu Val Lys Gln Lys Asn Pro Ser Trp Ser Asn Thr Gln Ile
225                 230                 235                 240

Arg Gln His Leu Thr Ser Thr Ala Thr Ser Leu Gly Asn Ser Asn Gln
                245                 250                 255

Phe Gly Ser Gly Leu Val Asn Ala Glu Ala Ala Thr Arg
        260                 265
```

```
<210> SEQ ID NO 52
<211> LENGTH: 274
<212> TYPE: PRT
<213> ORGANISM: Alkaliphilus transvaalensis

<400> SEQUENCE: 52

Ala Gln Ser Thr Pro Trp Gly Val Thr Arg Val Gln Ala Pro Asn Val
1               5                   10                  15

Trp Asn Arg Gly Phe Thr Gly Ser Gly Val Arg Val Ala Val Leu Asp
            20                  25                  30

Thr Gly Ile His Ser Ser His Glu Asp Leu Thr Val Ser Gly Gly Tyr
        35                  40                  45

Ser Val Phe Gly Asp Ser Pro Tyr Asn Asp Val Gln Gly His Gly Thr
    50                  55                  60

His Val Ala Gly Thr Ile Ala Ala Arg Asn Asn Ser Val Gly Val Ile
65                  70                  75                  80

Gly Val Ala Tyr Asn Ala Gln Leu Tyr Ala Val Lys Val Leu Asn Asn
                85                  90                  95

Gln Gly Ser Gly Thr Leu Ala Gly Ile Ala Gln Gly Ile Glu Trp Ala
            100                 105                 110

Arg Gln Asn Asn Met His Val Ile Asn Met Ser Leu Gly Gly Thr Ser
        115                 120                 125

Gly Ser Thr Thr Leu Gln Asn Ala Val Asn Ala Ala Tyr Asn Ala Gly
    130                 135                 140

Ile Leu Val Val Ala Ala Gly Asn Ser Gly Asn Ser Ala Gly Thr
145                 150                 155                 160

Gly Asp Asn Val Gly Phe Pro Ala Arg Tyr Pro Asn Ala Met Ala Val
                165                 170                 175

Ala Ala Thr Thr Ser Gly Asn Val Arg Ala Ser Phe Ser Ser Thr Gly
            180                 185                 190

Pro Ala Val Glu Ile Ala Ala Pro Gly Gln Asp Ile Asn Ser Thr Tyr
        195                 200                 205

Pro Thr Asn Thr Tyr Arg Ser Leu Asn Gly Thr Ser Met Ala Ala Pro
    210                 215                 220

His Val Ala Gly Val Ala Ala Leu Leu Lys Ser Ala Arg Pro Ala Val
225                 230                 235                 240

Thr Ala Ala Gly Ile Arg Asn Ala Met Asn Ser Thr Ala Leu Asn Leu
                245                 250                 255

Gly Asn Ser Asn Trp Tyr Gly Asn Gly Leu Val Arg Ala Asn Asn Ala
            260                 265                 270

Leu Asp

<210> SEQ ID NO 53
<211> LENGTH: 84
<212> TYPE: PRT
<213> ORGANISM: Bacillus lentus

<400> SEQUENCE: 53

Ala Glu Glu Ala Lys Glu Lys Tyr Leu Ile Gly Phe Asn Glu Gln Glu
1               5                   10                  15

Ala Val Ser Glu Phe Val Glu Gln Val Glu Ala Asn Asp Glu Val Lys
            20                  25                  30

Ile Leu Ser Glu Glu Glu Val Val Ile Glu Leu Leu His Glu Phe
        35                  40                  45

Glu Thr Ile Pro Val Leu Ser Val Glu Leu Ser Pro Glu Asp Val Asp
    50                  55                  60
```

```
Ala Leu Glu Leu Asp Pro Ala Ile Ser Tyr Ile Glu Glu Asp Ala Glu
 65                  70                  75                  80

Val Thr Thr Met
```

<210> SEQ ID NO 54
<211> LENGTH: 83
<212> TYPE: PRT
<213> ORGANISM: Bacillus sp.

<400> SEQUENCE: 54

```
Ala Glu Glu Ala Lys Glu Lys Tyr Leu Ile Gly Phe Lys Glu Gln Glu
 1               5                  10                  15

Val Met Ser Gln Phe Val Asp Gln Ile Asp Gly Asp Glu Tyr Ser Ile
                20                  25                  30

Ser Ser Gln Ala Glu Asp Val Glu Ile Asp Leu Leu His Glu Phe Asp
             35                  40                  45

Phe Ile Pro Val Leu Ser Val Glu Leu Asp Pro Glu Asp Val Asp Ala
         50                  55                  60

Leu Glu Leu Asp Pro Ala Ile Ala Tyr Ile Glu Glu Asp Ala Glu Val
 65                  70                  75                  80

Thr Thr Met
```

<210> SEQ ID NO 55
<211> LENGTH: 84
<212> TYPE: PRT
<213> ORGANISM: Bacillus sp.

<400> SEQUENCE: 55

```
Ala Glu Glu Ala Lys Glu Lys Tyr Leu Ile Gly Phe Lys Glu Gln Glu
 1               5                  10                  15

Val Met Ser Gln Phe Val Asp Gln Ile Asp Gly Asp Glu Tyr Ser Ile
                20                  25                  30

Ser Ser Ser Gln Val Glu Asp Val Glu Ile Asp Leu Leu His Glu Phe
             35                  40                  45

Asp Phe Ile Pro Val Leu Ser Val Glu Leu Asp Pro Gln Asp Val Glu
         50                  55                  60

Ala Leu Glu Leu Asp Pro Ala Ile Ser Tyr Ile Glu Glu Asp Ala Glu
 65                  70                  75                  80

Val Thr Thr Met
```

<210> SEQ ID NO 56
<211> LENGTH: 84
<212> TYPE: PRT
<213> ORGANISM: Bacillus clausii

<400> SEQUENCE: 56

```
Ala Glu Glu Ala Lys Glu Lys Tyr Leu Ile Gly Phe Asn Glu Gln Glu
 1               5                  10                  15

Ala Val Ser Glu Phe Val Glu Gln Ile Glu Ala Asn Asp Asp Val Ala
                20                  25                  30

Ile Leu Ser Glu Glu Glu Val Glu Ile Glu Leu Leu His Glu Phe
             35                  40                  45

Glu Thr Ile Pro Val Leu Ser Val Glu Leu Ser Pro Glu Asp Val Asp
         50                  55                  60

Ala Leu Glu Leu Asp Pro Thr Ile Ser Tyr Ile Glu Glu Asp Ala Glu
 65                  70                  75                  80
```

Val Thr Thr Met

<210> SEQ ID NO 57
<211> LENGTH: 87
<212> TYPE: PRT
<213> ORGANISM: Bacillus sp.

<400> SEQUENCE: 57

Ala Glu Glu Gln Lys Lys Gln Tyr Leu Ile Gly Phe Glu Asn Gln Leu
1               5                   10                  15

Gln Val Thr Glu Phe Val Glu Ser Ser Asp Lys Gly Gln Ser Glu Met
            20                  25                  30

Ser Leu Phe Ala Glu Val Asn Asp Glu Ser Ile Glu Met Glu Leu Leu
        35                  40                  45

Tyr Glu Phe Glu Asp Ile Pro Val Val Ser Val Glu Leu Ser Pro Glu
    50                  55                  60

Asp Val Lys Asp Leu Glu Lys Asp Pro Ser Ile Thr Tyr Ile Glu Glu
65                  70                  75                  80

Asp Ile Glu Val Thr Ile Thr
                85

<210> SEQ ID NO 58
<211> LENGTH: 71
<212> TYPE: PRT
<213> ORGANISM: Alkaliphilus transvaalensis

<400> SEQUENCE: 58

Ala Glu Asn Glu Lys Gln Glu Tyr Leu Val Gly Phe Asn Gly Lys Ala
1               5                   10                  15

Ser Arg Gly Leu Val Gln Ala Phe Gly Val Gln Asn Glu Ala Ile Leu
            20                  25                  30

His Glu Phe Gln Tyr Ile Asp Thr Val Leu Met Glu Leu Thr Pro Ala
        35                  40                  45

Gln Ala Lys Ala Leu Ala Asn Asn Pro Asn Val Glu Tyr Val Glu Glu
    50                  55                  60

Asn Ala Glu Val His Leu Leu
65                  70

<210> SEQ ID NO 59
<211> LENGTH: 382
<212> TYPE: PRT
<213> ORGANISM: Bacillus clausii

<400> SEQUENCE: 59

Val Arg Ser Lys Lys Leu Trp Ile Ser Leu Leu Phe Ala Leu Thr Leu
1               5                   10                  15

Ile Phe Thr Met Ala Phe Ser Asn Met Ser Ala Gln Ala Ala Glu Glu
            20                  25                  30

Ala Lys Glu Lys Tyr Leu Ile Gly Phe Asn Glu Gln Glu Ala Val Ser
        35                  40                  45

Glu Phe Val Glu Gln Val Glu Ala Asn Asp Glu Val Ala Ile Leu Ser
    50                  55                  60

Glu Glu Glu Glu Val Glu Ile Glu Leu Leu His Glu Phe Glu Thr Ile
65                  70                  75                  80

Pro Val Leu Ser Val Glu Leu Ser Pro Glu Asp Val Asp Ala Leu Glu
            85                  90                  95

Leu Asp Pro Ala Ile Ser Tyr Ile Glu Glu Asp Ala Glu Val Thr Thr
                100                 105                 110

```
Met Ala Gln Ser Val Pro Trp Gly Ile Ser Arg Val Gln Ala Pro Ala
            115                 120                 125

Ala His Asn Arg Gly Leu Thr Gly Ser Gly Val Lys Val Ala Val Leu
        130                 135                 140

Asp Thr Gly Ile Ser Thr His Pro Asp Leu Asn Ile Arg Gly Gly Ala
145                 150                 155                 160

Ser Phe Val Pro Gly Glu Pro Ser Thr Gln Asp Gly Asn Gly His Gly
                165                 170                 175

Thr His Val Ala Gly Thr Ile Ala Ala Leu Asn Asn Ser Ile Gly Val
            180                 185                 190

Leu Gly Val Ala Pro Ser Ala Glu Leu Tyr Ala Val Lys Val Leu Gly
        195                 200                 205

Ala Ser Gly Ser Gly Ser Val Ser Ser Ile Ala Gln Gly Leu Glu Trp
    210                 215                 220

Ala Gly Asn Asn Gly Met His Val Ala Asn Leu Ser Leu Gly Ser Pro
225                 230                 235                 240

Ser Pro Ser Ala Thr Leu Glu Gln Ala Val Asn Ser Ala Thr Ser Arg
                245                 250                 255

Gly Val Leu Val Val Ala Ala Ser Gly Asn Ser Gly Ala Gly Ser Ile
            260                 265                 270

Ser Tyr Pro Ala Arg Tyr Ala Asn Ala Met Ala Val Gly Ala Thr Asp
        275                 280                 285

Gln Asn Asn Asn Arg Ala Ser Phe Ser Gln Tyr Gly Ala Gly Leu Asp
    290                 295                 300

Ile Val Ala Pro Gly Val Asn Val Gln Ser Thr Tyr Pro Gly Ser Thr
305                 310                 315                 320

Tyr Ala Ser Leu Asn Gly Thr Ser Met Ala Thr Pro His Val Ala Gly
                325                 330                 335

Ala Ala Ala Leu Val Lys Gln Lys Asn Pro Ser Trp Ser Asn Val Gln
            340                 345                 350

Ile Arg Asn His Leu Lys Asn Thr Ala Thr Ser Leu Gly Ser Thr Asn
        355                 360                 365

Leu Tyr Gly Ser Gly Leu Val Asn Ala Glu Ala Thr Arg
    370                 375                 380

<210> SEQ ID NO 60
<211> LENGTH: 382
<212> TYPE: PRT
<213> ORGANISM: Artificial
<220> FEATURE:
<223> OTHER INFORMATION: synthetic peptide

<400> SEQUENCE: 60

Val Arg Ser Lys Lys Leu Trp Ile Ser Leu Leu Phe Ala Leu Thr Leu
1               5                   10                  15

Ile Phe Thr Met Ala Phe Ser Asn Met Ser Ala Gln Ala Ala Glu Glu
            20                  25                  30

Ala Lys Glu Lys Tyr Leu Ile Gly Phe Asn Glu Gln Glu Ala Val Ser
        35                  40                  45

Glu Phe Val Glu Gln Val Glu Ala Asn Asp Glu Val Ala Ile Leu Ser
    50                  55                  60

Glu Glu Glu Glu Val Glu Ile Glu Leu Leu His Glu Phe Glu Thr Ile
65                  70                  75                  80

Pro Val Leu Ser Val Glu Leu Ser Pro Glu Asp Val Asp Ala Leu Glu
                85                  90                  95
```

```
Leu Asp Pro Ala Ile Ser Tyr Ile Glu Glu Asp Ala Glu Val Thr Thr
            100                 105                 110

Met Ala Gln Ser Val Pro Trp Gly Ile Ser Arg Val Gln Ala Pro Ala
            115                 120                 125

Ala His Asn Arg Gly Leu Thr Gly Ser Gly Val Lys Val Ala Val Leu
        130                 135                 140

Asp Thr Gly Ile Ser Thr His Pro Asp Leu Asn Ile Arg Gly Gly Ala
145                 150                 155                 160

Ser Phe Val Pro Gly Glu Pro Ser Thr Gln Asp Gly Asn Gly His Gly
                165                 170                 175

Thr His Val Ala Gly Thr Ile Ala Ala Leu Asp Asn Ser Ile Gly Val
            180                 185                 190

Leu Gly Val Ala Pro Ser Ala Glu Leu Tyr Ala Val Lys Val Leu Gly
        195                 200                 205

Ala Ser Gly Ser Gly Ala Ile Ser Ser Ile Ala Gln Gly Leu Glu Trp
    210                 215                 220

Ala Gly Asn Asn Gly Met His Val Ala Asn Leu Ser Leu Gly Ser Pro
225                 230                 235                 240

Ser Pro Ser Ala Thr Leu Glu Gln Ala Val Asn Ser Ala Thr Ser Arg
                245                 250                 255

Gly Val Leu Val Val Ala Ala Ser Gly Asn Ser Gly Ala Gly Ser Ile
            260                 265                 270

Ser Tyr Pro Ala Arg Tyr Ala Asn Ala Met Ala Val Gly Ala Thr Asp
        275                 280                 285

Gln Asn Asn Asn Arg Ala Ser Phe Ser Gln Tyr Gly Ala Gly Leu Asp
    290                 295                 300

Ile Val Ala Pro Gly Val Asn Val Gln Ser Thr Tyr Pro Gly Ser Thr
305                 310                 315                 320

Tyr Ala Ser Leu Asn Gly Thr Ser Met Ala Thr Pro His Val Ala Gly
                325                 330                 335

Ala Ala Ala Leu Val Lys Gln Lys Asn Pro Ser Trp Ser Asn Val Gln
            340                 345                 350

Ile Arg Asn His Leu Lys Asn Thr Ala Thr Ser Leu Gly Ser Thr Asn
        355                 360                 365

Leu Tyr Gly Ser Gly Leu Val Asn Ala Glu Ala Ala Thr Arg
    370                 375                 380

<210> SEQ ID NO 61
<211> LENGTH: 382
<212> TYPE: PRT
<213> ORGANISM: Artificial
<220> FEATURE:
<223> OTHER INFORMATION: synthetic peptide

<400> SEQUENCE: 61

Val Arg Ser Lys Lys Leu Trp Ile Ser Leu Leu Phe Ala Leu Thr Leu
1               5                   10                  15

Ile Phe Thr Met Ala Phe Ser Asn Met Ser Ala Gln Ala Ala Glu Glu
            20                  25                  30

Ala Lys Glu Lys Tyr Leu Ile Gly Phe Asn Glu Gln Glu Ala Val Ser
        35                  40                  45

Glu Phe Val Glu Gln Val Glu Ala Asn Asp Glu Val Ala Ile Leu Ser
    50                  55                  60

Glu Glu Glu Glu Val Glu Ile Glu Leu Leu His Glu Phe Glu Thr Ile
65                  70                  75                  80
```

```
Pro Val Leu Ser Val Glu Leu Ser Pro Glu Asp Val Asp Ala Leu Glu
                85                  90                  95

Leu Asp Pro Ala Ile Ser Tyr Ile Glu Asp Ala Glu Val Thr Thr
            100                 105                 110

Met Ala Gln Ser Val Pro Trp Gly Ile Ser Arg Val Gln Ala Pro Ala
            115                 120                 125

Ala His Asn Arg Gly Leu Thr Gly Ser Gly Val Lys Val Ala Val Leu
130                 135                 140

Asp Thr Gly Ile Ser Thr His Pro Asp Leu Asn Ile Arg Gly Gly Ala
145                 150                 155                 160

Ser Phe Val Pro Gly Glu Pro Ser Thr Gln Asp Gly Asn Gly His Gly
                165                 170                 175

Thr His Val Ala Gly Thr Ile Ala Ala Leu Asn Asn Ser Ile Gly Val
            180                 185                 190

Leu Gly Val Ala Pro Asn Ala Glu Leu Tyr Ala Val Lys Val Leu Gly
            195                 200                 205

Ala Ser Gly Ser Gly Ser Val Ser Ser Ile Ala Gln Gly Leu Glu Trp
210                 215                 220

Ala Gly Asn Asn Gly Met His Val Ala Asn Leu Ser Leu Gly Ser Pro
225                 230                 235                 240

Ser Pro Ser Ala Thr Leu Glu Gln Ala Val Asn Ser Ala Thr Ser Arg
                245                 250                 255

Gly Val Leu Val Val Ala Ala Ser Gly Asn Ser Gly Ala Gly Ser Ile
            260                 265                 270

Ser Tyr Pro Ala Arg Tyr Ala Asn Ala Met Ala Val Gly Ala Thr Asp
            275                 280                 285

Gln Asn Asn Asn Arg Ala Ser Phe Ser Gln Tyr Gly Ala Gly Leu Asp
290                 295                 300

Ile Val Ala Pro Gly Val Asn Val Gln Ser Thr Tyr Pro Gly Ser Thr
305                 310                 315                 320

Tyr Ala Ser Leu Asn Gly Thr Ser Met Ala Thr Pro His Val Ala Gly
                325                 330                 335

Ala Ala Ala Leu Val Lys Gln Lys Asn Pro Ser Trp Ser Asn Val Gln
            340                 345                 350

Ile Arg Asn His Leu Lys Asn Thr Ala Thr Ser Leu Gly Ser Thr Asn
            355                 360                 365

Leu Tyr Gly Ser Gly Leu Val Asn Ala Glu Ala Ala Thr Arg
            370                 375                 380

<210> SEQ ID NO 62
<211> LENGTH: 382
<212> TYPE: PRT
<213> ORGANISM: Artificial
<220> FEATURE:
<223> OTHER INFORMATION: synthetic peptide

<400> SEQUENCE: 62

Val Arg Ser Lys Lys Leu Trp Ile Ser Leu Leu Phe Ala Leu Thr Leu
1               5                   10                  15

Ile Phe Thr Met Ala Phe Ser Asn Met Ser Ala Gln Ala Ala Glu Glu
            20                  25                  30

Ala Lys Glu Lys Tyr Leu Ile Gly Phe Asn Glu Gln Glu Ala Val Ser
        35                  40                  45

Glu Phe Val Glu Gln Val Glu Ala Asn Asp Glu Val Ala Ile Leu Ser
    50                  55                  60
```

-continued

```
Glu Glu Glu Glu Val Glu Ile Glu Leu Leu His Phe Glu Thr Ile
 65                  70                  75                  80

Pro Val Leu Ser Val Glu Leu Ser Pro Glu Asp Val Asp Ala Leu Glu
                 85                  90                  95

Leu Asp Pro Ala Ile Ser Tyr Ile Glu Glu Asp Ala Glu Val Thr Thr
            100                 105                 110

Met Ala Gln Ser Val Pro Trp Gly Ile Ser Arg Val Gln Ala Pro Ala
            115                 120                 125

Ala His Asn Arg Gly Leu Thr Gly Ser Gly Val Lys Val Ala Val Leu
130                 135                 140

Asp Thr Gly Ile Ser Thr His Pro Asp Leu Asn Ile Arg Gly Gly Ala
145                 150                 155                 160

Ser Phe Val Pro Gly Glu Pro Ser Thr Gln Asp Gly Asn Gly His Gly
                165                 170                 175

Thr His Val Ala Gly Thr Ile Ala Ala Leu Asn Asn Ser Ile Gly Val
            180                 185                 190

Leu Gly Val Ala Pro Asn Ala Glu Leu Tyr Ala Val Lys Val Leu Gly
            195                 200                 205

Ala Ser Gly Ser Gly Ser Val Ser Ser Ile Ala Gln Gly Leu Glu Trp
210                 215                 220

Ala Gly Asn Asn Val Met His Val Ala Asn Leu Ser Leu Gly Leu Gln
225                 230                 235                 240

Ala Pro Ser Ala Thr Leu Glu Gln Ala Val Asn Ser Ala Thr Ser Arg
                245                 250                 255

Gly Val Leu Val Val Ala Ala Ser Gly Asn Ser Gly Ala Gly Ser Ile
            260                 265                 270

Ser Tyr Pro Ala Arg Tyr Ala Asn Ala Met Ala Val Gly Ala Thr Asp
            275                 280                 285

Gln Asn Asn Asn Arg Ala Ser Phe Ser Gln Tyr Gly Ala Gly Leu Asp
290                 295                 300

Ile Val Ala Pro Gly Val Asn Val Gln Ser Thr Tyr Pro Gly Ser Thr
305                 310                 315                 320

Tyr Ala Ser Leu Asn Gly Thr Ser Met Ala Thr Pro His Val Ala Gly
                325                 330                 335

Ala Ala Ala Leu Val Lys Gln Lys Asn Pro Ser Trp Ser Asn Val Gln
            340                 345                 350

Ile Arg Asn His Leu Lys Asn Thr Ala Thr Ser Leu Gly Ser Thr Asn
            355                 360                 365

Leu Tyr Gly Ser Gly Leu Val Asn Ala Glu Ala Ala Thr Arg
370                 375                 380
```

<210> SEQ ID NO 63
<211> LENGTH: 382
<212> TYPE: PRT
<213> ORGANISM: Artificial
<220> FEATURE:
<223> OTHER INFORMATION: synthetic peptide

<400> SEQUENCE: 63

```
Val Arg Ser Lys Lys Leu Trp Ile Ser Leu Leu Phe Ala Leu Thr Leu
 1               5                  10                  15

Ile Phe Thr Met Ala Phe Ser Asn Met Ser Ala Gln Ala Ala Glu Glu
                20                  25                  30

Ala Lys Glu Lys Tyr Leu Ile Gly Phe Asn Glu Gln Glu Ala Val Ser
            35                  40                  45
```

Glu Phe Val Glu Gln Val Ala Asn Asp Glu Val Ala Ile Leu Ser
 50                  55                  60

Glu Glu Glu Glu Val Glu Ile Glu Leu Leu His Glu Phe Glu Thr Ile
65                  70                  75                  80

Pro Val Leu Ser Val Glu Leu Ser Pro Glu Asp Val Asp Ala Leu Glu
                 85                  90                  95

Leu Asp Pro Ala Ile Ser Tyr Ile Glu Glu Asp Ala Glu Val Thr Thr
            100                 105                 110

Met Ala Gln Ser Val Pro Trp Gly Ile Ser Arg Val Gln Ala Pro Ala
            115                 120                 125

Ala His Asn Arg Gly Leu Thr Gly Ser Gly Val Lys Val Ala Val Leu
130                 135                 140

Asp Thr Gly Ile Ser Thr His Pro Asp Leu Asn Ile Arg Gly Gly Ala
145                 150                 155                 160

Ser Phe Val Pro Gly Glu Pro Ser Thr Gln Asp Gly Asn Gly His Gly
                165                 170                 175

Thr His Val Ala Gly Thr Ile Ala Ala Leu Asn Asn Ser Ile Gly Val
            180                 185                 190

Leu Gly Val Ala Pro Asn Ala Glu Leu Tyr Ala Val Lys Val Leu Gly
            195                 200                 205

Ala Ser Gly Met Gly Ser Val Ser Ser Ile Ala Gln Gly Leu Glu Trp
210                 215                 220

Ala Gly Asn Asn Val Met His Val Ala Asn Leu Ser Leu Gly Leu Gln
225                 230                 235                 240

Ala Pro Ser Ala Thr Leu Glu Gln Ala Val Asn Ser Ala Thr Ser Arg
                245                 250                 255

Gly Val Leu Val Val Ala Ala Ser Gly Asn Ser Gly Ala Gly Ser Ile
            260                 265                 270

Ser Tyr Pro Ala Arg Tyr Ala Asn Ala Met Ala Val Gly Ala Thr Asp
            275                 280                 285

Gln Asn Asn Asn Arg Ala Ser Phe Ser Gln Tyr Gly Ala Gly Leu Asp
290                 295                 300

Ile Val Ala Pro Gly Val Asn Val Gln Ser Thr Tyr Pro Gly Ser Thr
305                 310                 315                 320

Tyr Ala Ser Leu Asn Gly Thr Ser Met Ala Thr Pro His Val Ala Gly
                325                 330                 335

Ala Ala Ala Leu Val Lys Gln Lys Asn Pro Ser Trp Ser Asn Val Gln
            340                 345                 350

Ile Arg Asn His Leu Lys Asn Thr Ala Thr Ser Leu Gly Ser Thr Asn
            355                 360                 365

Leu Tyr Gly Ser Gly Leu Val Asn Ala Glu Ala Ala Thr Arg
    370                 375                 380

<210> SEQ ID NO 64
<211> LENGTH: 382
<212> TYPE: PRT
<213> ORGANISM: Artificial
<220> FEATURE:
<223> OTHER INFORMATION: synthetic primer

<400> SEQUENCE: 64

Val Arg Ser Lys Lys Leu Trp Ile Ser Leu Leu Phe Ala Leu Thr Leu
1                5                  10                  15

Ile Phe Thr Met Ala Phe Ser Asn Met Ser Ala Gln Ala Ala Glu Glu
                20                  25                  30

Ala Lys Glu Lys Tyr Leu Ile Gly Phe Asn Glu Gln Glu Ala Val Ser
         35                  40                  45

Glu Phe Val Glu Gln Val Ala Asn Asp Glu Val Ala Ile Leu Ser
 50                  55                  60

Glu Glu Glu Glu Val Glu Ile Glu Leu His Glu Phe Glu Thr Ile
 65                  70                  75                  80

Pro Val Leu Ser Val Glu Leu Ser Pro Glu Asp Val Asp Ala Leu Glu
                 85                  90                  95

Leu Asp Pro Ala Ile Ser Tyr Ile Glu Glu Asp Ala Glu Val Thr Thr
                100                 105                 110

Met Ala Gln Ser Val Pro Trp Gly Ile Ser Arg Val Gln Ala Pro Ala
                115                 120                 125

Ala His Asn Arg Gly Leu Thr Gly Ser Gly Val Lys Val Ala Val Leu
130                 135                 140

Asp Thr Gly Ile Ser Thr His Pro Asp Leu Asn Ile Arg Gly Gly Ala
145                 150                 155                 160

Ser Phe Val Pro Gly Glu Pro Ser Thr Gln Asp Gly Asn Gly His Gly
                165                 170                 175

Thr His Val Ala Gly Thr Ile Ala Ala Leu Asn Asn Ser Ile Gly Val
                180                 185                 190

Leu Gly Val Ala Pro Asn Ala Glu Leu Tyr Ala Val Lys Val Leu Gly
                195                 200                 205

Ala Ser Gly Gly Gly Ser Asn Ser Ser Ile Ala Gln Gly Leu Glu Trp
210                 215                 220

Ala Gly Asn Asn Gly Met His Val Ala Asn Leu Ser Leu Gly Ser Pro
225                 230                 235                 240

Ser Pro Ser Ala Thr Leu Glu Gln Ala Val Asn Ser Ala Thr Ser Arg
                245                 250                 255

Gly Val Leu Val Val Ala Ala Ser Gly Asn Ser Gly Ala Gly Ser Ile
                260                 265                 270

Ser Tyr Pro Ala Arg Tyr Ala Asn Ala Met Ala Val Gly Ala Thr Asp
                275                 280                 285

Gln Asn Asn Asn Arg Ala Ser Phe Ser Gln Tyr Gly Ala Gly Leu Asp
                290                 295                 300

Ile Val Ala Pro Gly Val Asn Val Gln Ser Thr Tyr Pro Gly Ser Thr
305                 310                 315                 320

Tyr Ala Ser Leu Asn Gly Thr Ser Met Ala Thr Pro His Val Ala Gly
                325                 330                 335

Ala Ala Ala Leu Val Lys Gln Lys Asn Pro Ser Trp Ser Asn Val Gln
                340                 345                 350

Ile Arg Asn His Leu Lys Asn Thr Ala Thr Ser Leu Gly Ser Thr Asn
                355                 360                 365

Leu Tyr Gly Ser Gly Leu Val Asn Ala Glu Ala Ala Thr Arg
                370                 375                 380

<210> SEQ ID NO 65
<211> LENGTH: 382
<212> TYPE: PRT
<213> ORGANISM: Artificial
<220> FEATURE:
<223> OTHER INFORMATION: synthetic peptide

<400> SEQUENCE: 65

Val Arg Ser Lys Lys Leu Trp Ile Ser Leu Leu Phe Ala Leu Thr Leu
 1               5                  10                  15

```
Ile Phe Thr Met Ala Phe Ser Asn Met Ser Ala Gln Ala Ala Glu Glu
             20                  25                  30

Ala Lys Glu Lys Tyr Leu Ile Gly Phe Asn Glu Gln Glu Ala Val Ser
         35                  40                  45

Glu Phe Val Glu Gln Val Glu Ala Asn Asp Glu Val Ala Ile Leu Ser
 50                  55                  60

Glu Glu Glu Glu Val Glu Ile Glu Leu Leu His Glu Phe Glu Thr Ile
 65                  70                  75                  80

Pro Val Leu Ser Val Glu Leu Ser Pro Glu Asp Val Asp Ala Leu Glu
                 85                  90                  95

Leu Asp Pro Ala Ile Ser Tyr Ile Glu Glu Asp Ala Glu Val Thr Thr
             100                 105                 110

Met Ala Gln Ser Val Pro Trp Gly Ile Ser Arg Val Gln Ala Pro Ala
         115                 120                 125

Ala His Asn Arg Gly Leu Thr Gly Ser Gly Val Lys Val Ala Val Leu
130                 135                 140

Asp Thr Gly Ile Ser Thr His Pro Asp Leu Asn Ile Arg Gly Gly Ala
145                 150                 155                 160

Ser Phe Val Pro Gly Glu Pro Ser Thr Gln Asp Gly Asn Gly His Gly
                 165                 170                 175

Thr His Val Ala Gly Thr Ile Ala Ala Leu Asp Asn Ser Ile Gly Val
             180                 185                 190

Leu Gly Val Ala Pro Arg Ala Glu Leu Tyr Ala Val Lys Val Leu Gly
         195                 200                 205

Ala Ser Gly Ser Gly Ser Val Ser Ser Ile Ala Gln Gly Leu Glu Trp
210                 215                 220

Ala Gly Asn Asn Arg Met His Val Ala Asn Leu Ser Leu Gly Leu Gln
225                 230                 235                 240

Ala Pro Ser Ala Thr Leu Glu Gln Ala Val Asn Ser Ala Thr Ser Arg
                 245                 250                 255

Gly Val Leu Val Val Ala Ala Ser Gly Asn Ser Gly Ala Gly Ser Ile
             260                 265                 270

Ser Tyr Pro Ala Arg Tyr Ala Asn Ala Met Ala Val Gly Ala Thr Asp
         275                 280                 285

Gln Asn Asn Asn Arg Ala Ser Phe Ser Gln Tyr Gly Ala Gly Leu Asp
290                 295                 300

Ile Val Ala Pro Gly Val Asn Val Gln Ser Thr Tyr Pro Gly Ser Thr
305                 310                 315                 320

Tyr Ala Ser Leu Asn Gly Thr Ser Met Ala Thr Pro His Val Ala Gly
                 325                 330                 335

Ala Ala Ala Leu Val Lys Gln Lys Asn Pro Ser Trp Ser Asn Val Gln
             340                 345                 350

Ile Arg Asn His Leu Lys Asn Thr Ala Thr Ser Leu Gly Ser Thr Asn
         355                 360                 365

Leu Tyr Gly Ser Gly Leu Val Asn Ala Glu Ala Ala Thr Arg
370                 375                 380

<210> SEQ ID NO 66
<211> LENGTH: 381
<212> TYPE: PRT
<213> ORGANISM: Artificial
<220> FEATURE:
<223> OTHER INFORMATION: synthetic peptide

<400> SEQUENCE: 66
```

Val Arg Ser Lys Lys Leu Trp Ile Ser Leu Leu Phe Ala Leu Thr Leu
1               5                   10                  15

Ile Phe Thr Met Ala Phe Ser Asn Met Ser Ala Gln Ala Ala Glu Glu
            20                  25                  30

Ala Lys Glu Lys Tyr Leu Ile Gly Phe Asn Glu Gln Glu Ala Val Ser
        35                  40                  45

Glu Phe Val Glu Gln Val Glu Ala Asn Asp Glu Val Ala Ile Leu Ser
50                  55                  60

Glu Glu Glu Glu Val Glu Ile Glu Leu Leu His Glu Phe Glu Thr Ile
65                  70                  75                  80

Pro Val Leu Ser Val Glu Leu Ser Pro Glu Asp Val Asp Ala Leu Glu
                85                  90                  95

Leu Asp Pro Ala Ile Ser Tyr Ile Glu Glu Asp Ala Glu Val Thr Thr
            100                 105                 110

Met Ala Gln Ser Val Pro Trp Gly Ile Ser Arg Val Gln Ala Pro Ala
        115                 120                 125

Ala His Asn Arg Gly Leu Thr Gly Ser Gly Val Lys Val Ala Val Leu
130                 135                 140

Asp Thr Gly Ile Ser Thr His Pro Asp Leu Asn Ile Arg Gly Gly Ala
145                 150                 155                 160

Ser Phe Val Pro Gly Glu Pro Ser Thr Gln Asp Gly Asn Gly His Gly
                165                 170                 175

Thr His Val Ala Gly Thr Ile Ala Ala Leu Asp Asn Ser Ile Gly Val
            180                 185                 190

Leu Gly Val Ala Pro Arg Ala Glu Leu Tyr Ala Val Lys Val Leu Gly
        195                 200                 205

Ala Ser Gly Ser Gly Ser Val Ser Ser Ile Ala Gln Gly Leu Glu Trp
210                 215                 220

Ala Gly Asn Asn Arg Met His Val Ala Asn Leu Ser Leu Gly Leu Gln
225                 230                 235                 240

Ala Pro Ser Ala Thr Leu Glu Gln Ala Val Asn Ser Ala Thr Ser Arg
                245                 250                 255

Gly Val Leu Val Val Ala Ala Ser Gly Asn Ser Gly Ala Gly Ser Ile
            260                 265                 270

Ser Tyr Pro Ala Arg Tyr Ala Asn Ala Met Ala Val Gly Ala Thr Asp
        275                 280                 285

Gln Asn Asn Asn Arg Ala Asp Phe Ser Gln Tyr Gly Ala Gly Leu Asp
290                 295                 300

Ile Val Ala Pro Gly Val Asn Val Gln Ser Thr Tyr Pro Gly Ser Thr
305                 310                 315                 320

Tyr Ala Ser Leu Asn Gly Thr Ser Met Ala Thr Pro His Val Ala Gly
                325                 330                 335

Ala Ala Ala Leu Val Lys Gln Lys Asn Pro Ser Trp Ser Asn Arg Gln
            340                 345                 350

Ile Arg Asn His Leu Lys Asn Thr Ala Thr Ser Leu Gly Ser Thr Asn
        355                 360                 365

Leu Tyr Gly Ser Gly Leu Val Asn Ala Glu Ala Thr
370                 375                 380

<210> SEQ ID NO 67
<211> LENGTH: 382
<212> TYPE: PRT
<213> ORGANISM: Artificial
<220> FEATURE:

<223> OTHER INFORMATION: synthetic peptide

<400> SEQUENCE: 67

| | | | | | | | | | | | | | | |
|---|---|---|---|---|---|---|---|---|---|---|---|---|---|---|
| Val | Arg | Ser | Lys | Lys | Leu | Trp | Ile | Ser | Leu | Leu | Phe | Ala | Leu | Thr | Leu |
| 1 | | | | 5 | | | | | 10 | | | | | 15 | |
| Ile | Phe | Thr | Met | Ala | Phe | Ser | Asn | Met | Ser | Ala | Gln | Ala | Ala | Glu | Glu |
| | | | 20 | | | | | 25 | | | | | 30 | | |
| Ala | Lys | Glu | Lys | Tyr | Leu | Ile | Gly | Phe | Asn | Glu | Gln | Glu | Ala | Val | Ser |
| | | 35 | | | | | 40 | | | | | 45 | | | |
| Glu | Phe | Val | Glu | Gln | Val | Glu | Ala | Asn | Asp | Glu | Val | Ala | Ile | Leu | Ser |
| | 50 | | | | | 55 | | | | | 60 | | | | |
| Glu | Glu | Glu | Val | Glu | Ile | Glu | Leu | Leu | His | Glu | Phe | Glu | Thr | Ile |
| 65 | | | | | 70 | | | | | 75 | | | | 80 |
| Pro | Val | Leu | Ser | Val | Glu | Leu | Ser | Pro | Glu | Asp | Val | Asp | Ala | Leu | Glu |
| | | | | 85 | | | | | 90 | | | | | 95 | |
| Leu | Asp | Pro | Ala | Ile | Ser | Tyr | Ile | Glu | Glu | Asp | Ala | Glu | Val | Thr | Thr |
| | | | 100 | | | | | 105 | | | | | 110 | | |
| Met | Ala | Gln | Ser | Val | Pro | Trp | Gly | Ile | Ser | Arg | Val | Gln | Ala | Pro | Ala |
| | | 115 | | | | | 120 | | | | | 125 | | | |
| Ala | His | Asn | Arg | Gly | Leu | Thr | Gly | Ser | Gly | Val | Lys | Val | Ala | Val | Leu |
| | 130 | | | | | 135 | | | | | 140 | | | | |
| Asp | Thr | Gly | Ile | Ser | Thr | His | Pro | Asp | Leu | Asn | Ile | Arg | Gly | Gly | Ala |
| 145 | | | | | 150 | | | | | 155 | | | | | 160 |
| Ser | Phe | Val | Pro | Gly | Glu | Pro | Ser | Thr | Gln | Asp | Gly | Asn | Gly | His | Gly |
| | | | | 165 | | | | | 170 | | | | | 175 | |
| Thr | His | Val | Ala | Gly | Thr | Ile | Ala | Ala | Leu | Asp | Asn | Ser | Ile | Gly | Val |
| | | | 180 | | | | | 185 | | | | | 190 | | |
| Leu | Gly | Val | Ala | Pro | Arg | Ala | Glu | Leu | Tyr | Ala | Val | Lys | Val | Leu | Gly |
| | | 195 | | | | | 200 | | | | | 205 | | | |
| Ala | Ser | Gly | Ser | Gly | Ser | Val | Ser | Ser | Ile | Ala | Gln | Gly | Leu | Glu | Trp |
| | 210 | | | | | 215 | | | | | 220 | | | | |
| Ala | Gly | Asn | Asn | Gly | Met | His | Val | Ala | Asn | Leu | Ser | Leu | Gly | Leu | Gln |
| 225 | | | | | 230 | | | | | 235 | | | | | 240 |
| Ala | Pro | Ser | Ala | Thr | Leu | Glu | Gln | Ala | Val | Asn | Ser | Ala | Thr | Ser | Arg |
| | | | | 245 | | | | | 250 | | | | | 255 | |
| Gly | Val | Leu | Val | Val | Ala | Ala | Ser | Gly | Asn | Ser | Gly | Ala | Gly | Ser | Ile |
| | | | 260 | | | | | 265 | | | | | 270 | | |
| Ser | Tyr | Pro | Ala | Arg | Tyr | Ala | Asn | Ala | Met | Ala | Val | Gly | Ala | Thr | Asp |
| | | 275 | | | | | 280 | | | | | 285 | | | |
| Gln | Asn | Asn | Arg | Ala | Asp | Phe | Ser | Gln | Tyr | Gly | Ala | Gly | Leu | Asp |
| | 290 | | | | | 295 | | | | | 300 | | | | |
| Ile | Val | Ala | Pro | Gly | Val | Asn | Val | Gln | Ser | Thr | Tyr | Pro | Gly | Ser | Thr |
| 305 | | | | | 310 | | | | | 315 | | | | | 320 |
| Tyr | Ala | Ser | Leu | Asn | Gly | Thr | Ser | Met | Ala | Thr | Pro | His | Val | Ala | Gly |
| | | | | 325 | | | | | 330 | | | | | 335 | |
| Ala | Ala | Ala | Leu | Val | Lys | Gln | Lys | Asn | Pro | Ser | Trp | Ser | Asn | Val | Gln |
| | | | 340 | | | | | 345 | | | | | 350 | | |
| Ile | Arg | Arg | His | Leu | Lys | Asn | Thr | Ala | Thr | Ser | Leu | Gly | Ser | Thr | Asn |
| | | 355 | | | | | 360 | | | | | 365 | | | |
| Leu | Tyr | Gly | Ser | Gly | Leu | Val | Asn | Ala | Glu | Ala | Ala | Thr | Arg |
| | 370 | | | | | 375 | | | | | 380 | | | |

<210> SEQ ID NO 68
<211> LENGTH: 4

```
<212> TYPE: PRT
<213> ORGANISM: Artificial
<220> FEATURE:
<223> OTHER INFORMATION: synthetic reagent

<400> SEQUENCE: 68

Ala Ala Pro Phe
1
```